(12) United States Patent
Marchand et al.

(10) Patent No.: US 10,238,393 B2
(45) Date of Patent: *Mar. 26, 2019

(54) MULTIPLE LAYER FILAMENTARY DEVICES FOR TREATMENT OF VASCULAR DEFECTS

(71) Applicant: SEQUENT MEDICAL INC., Aliso Viejo, CA (US)

(72) Inventors: Philippe Marchand, Lake Forrest, CA (US); Brian J. Cox, Laguna Niguel, CA (US); Robert F. Rosenbluth, Laguna Niguel, CA (US); John Nolting, Poway, CA (US); Tan Q. Dinh, Santa Ana, CA (US)

(73) Assignee: SEQUENT MEDICAL INC., Aliso Viejo, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/094,084

(22) Filed: Apr. 8, 2016

(65) Prior Publication Data

US 2016/0249937 A1 Sep. 1, 2016

Related U.S. Application Data

(63) Continuation of application No. 13/439,754, filed on Apr. 4, 2012, which is a continuation of application No. 12/939,901, filed on Nov. 4, 2010, now abandoned.

(60) Provisional application No. 61/334,130, filed on May 12, 2010, provisional application No. 61/294,760, (Continued)

(51) Int. Cl.
*A61M 29/00* (2006.01)
*A61B 17/12* (2006.01)
*A61B 17/00* (2006.01)
*A61B 17/22* (2006.01)

(52) U.S. Cl.
CPC .. *A61B 17/12113* (2013.01); *A61B 17/12022* (2013.01); *A61B 17/12118* (2013.01); *A61B 17/12172* (2013.01); *A61B 17/12177* (2013.01); *A61B 2017/00526* (2013.01); *A61B 2017/1205* (2013.01); *A61B 2017/22067* (2013.01)

(58) Field of Classification Search
CPC ........ A61B 17/12113; A61B 17/12022; A61B 17/12172; A61B 17/12118; A61B 17/12177; A61B 2017/1205; A61B 2017/22067; A61B 2017/00526
USPC ................................. 606/157, 200
See application file for complete search history.

(56) References Cited

U.S. PATENT DOCUMENTS 5,334,210 A * 8/1994 Gianturco ........ A61B 17/12022
604/907
5,522,822 A * 6/1996 Phelps ............. A61B 17/12022
606/151

(Continued)

FOREIGN PATENT DOCUMENTS

FR 2834199 7/2003
WO 2004045393 6/2004

*Primary Examiner* — Amy R Weisberg
(74) *Attorney, Agent, or Firm* — John L. Rogitz

(57) ABSTRACT

Devices and methods for treatment of a patient's vasculature with some embodiments configured for delivery with a microcatheter for treatment of the cerebral vasculature of a patient. Some embodiments may include a permeable shell and inner structure configured to occlude blood flow therethrough.

16 Claims, 47 Drawing Sheets

Related U.S. Application Data filed on Jan. 13, 2010, provisional application No. 61/258,541, filed on Nov. 5, 2009.

(56) References Cited

U.S. PATENT DOCUMENTS

| | | | | |
|---|---|---|---|---|
| 6,168,622 B1* | 1/2001 | Mazzocchi | A61B 17/0057 | 606/200 |
| 6,346,117 B1* | 2/2002 | Greenhalgh | A61B 17/12022 | 606/200 |
| 6,375,668 B1* | 4/2002 | Gifford | A61B 17/12022 | 606/200 |
| 6,391,037 B1* | 5/2002 | Greenhalgh | A61B 17/12022 | 606/151 |
| 6,994,717 B2* | 2/2006 | Konya | A61B 17/12022 | 606/200 |
| 7,101,390 B2* | 9/2006 | Nelson | A61F 2/07 | 623/1.12 |
| 7,806,919 B2* | 10/2010 | Bloom | A61F 2/2418 | 623/1.15 |
| 8,974,487 B2* | 3/2015 | Connor | A61B 17/12022 | 606/198 |
| 2002/0169473 A1* | 11/2002 | Sepetka | A61B 17/12022 | 606/200 |
| 2003/0028209 A1* | 2/2003 | Teoh | A61B 17/12022 | 606/191 |
| 2004/0260333 A1* | 12/2004 | Dubrul | A61B 17/22 | 606/200 |
| 2006/0009798 A1* | 1/2006 | Callister | A61B 17/12022 | 606/200 |
| 2006/0009799 A1 | 1/2006 | Kleshinski et al. | | |
| 2008/0119886 A1* | 5/2008 | Greenhalgh | A61B 17/0057 | 606/200 |
| 2009/0062841 A1* | 3/2009 | Amplatz | A61B 17/0057 | 606/200 |
| 2009/0112305 A1 | 4/2009 | Goldmann et al. | | |
| 2009/0132024 A1* | 5/2009 | Berkhoff | A61F 2/07 | 623/1.15 |
| 2009/0270974 A1 | 10/2009 | Berez et al. | | |
| 2009/0287291 A1 | 11/2009 | Becking et al. | | |
| 2010/0094409 A1* | 4/2010 | Barker | A61F 2/07 | 623/1.46 |
| 2011/0208227 A1* | 8/2011 | Becking | A61B 17/12022 | 606/191 |
| 2012/0239074 A1 | 9/2012 | Aboytes et al. | | |

* cited by examiner

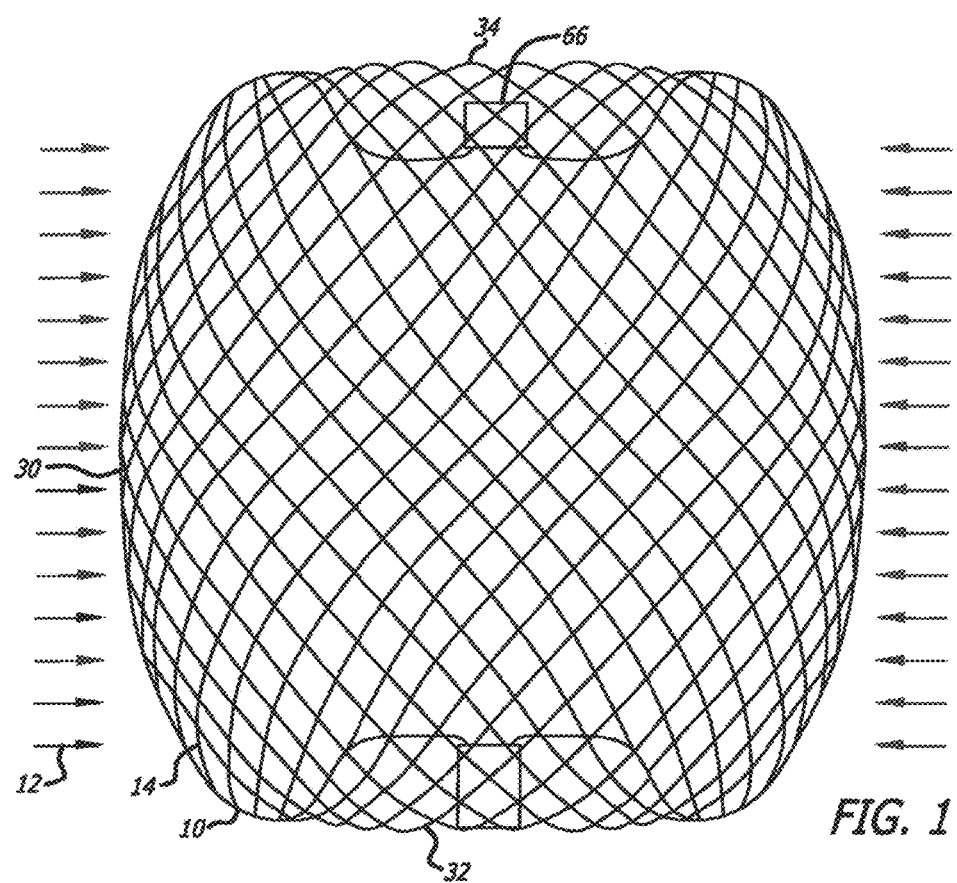
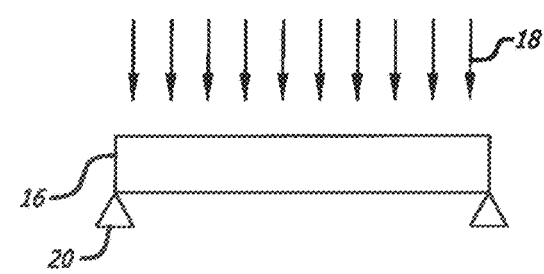

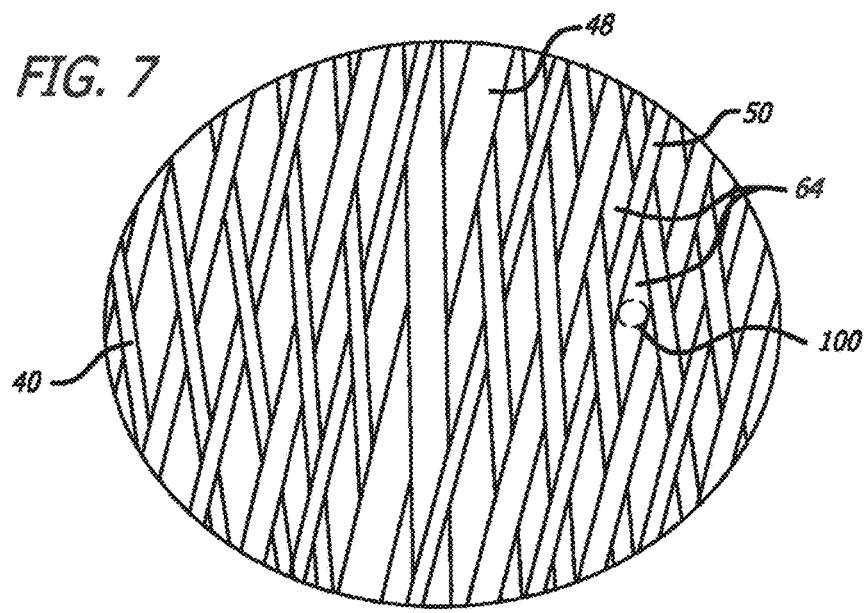
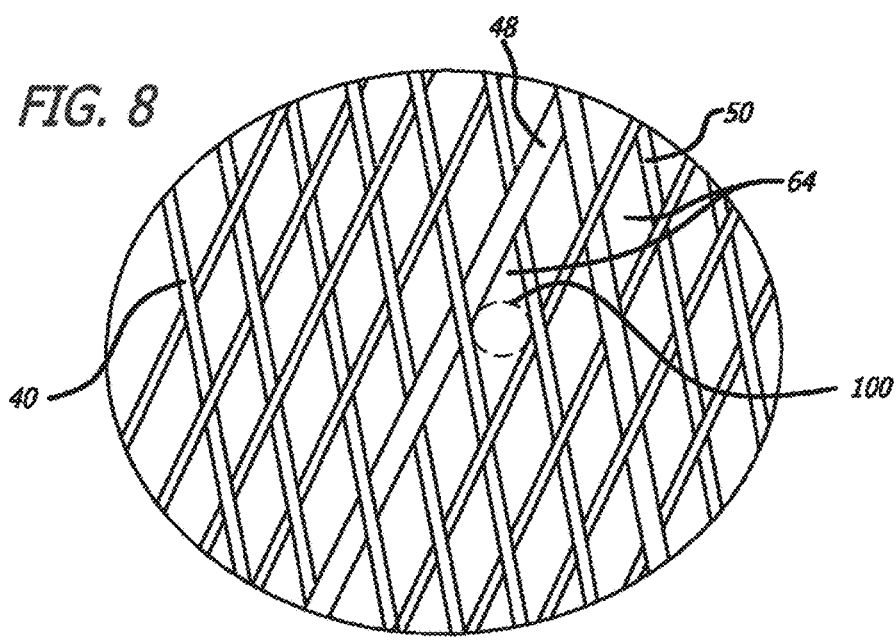

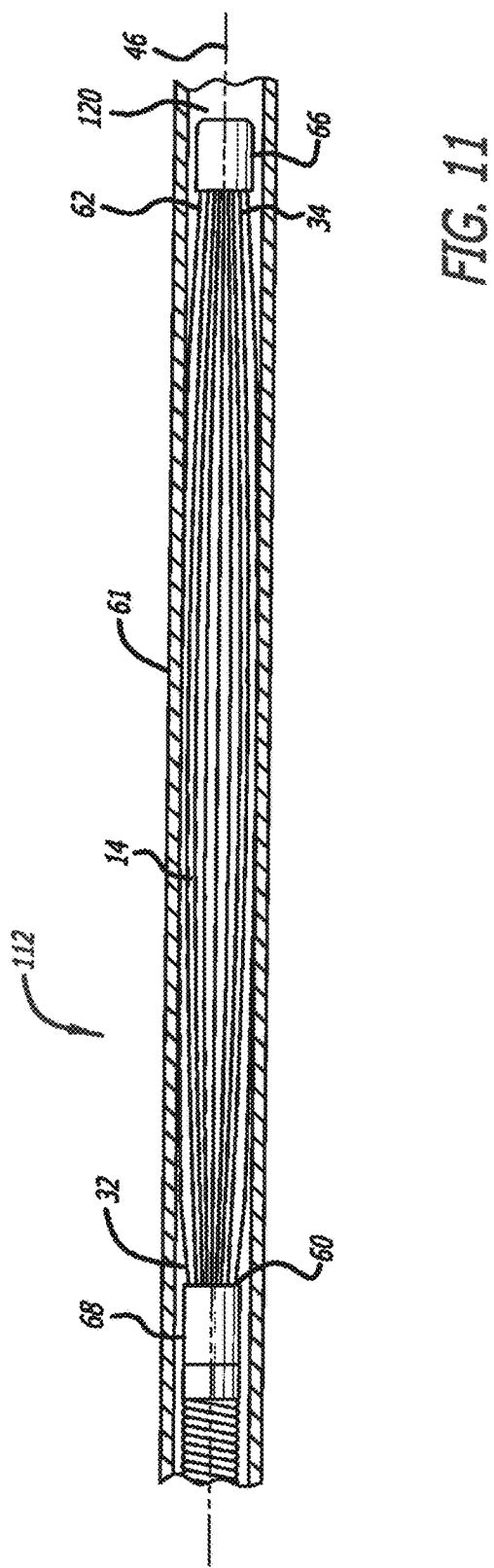

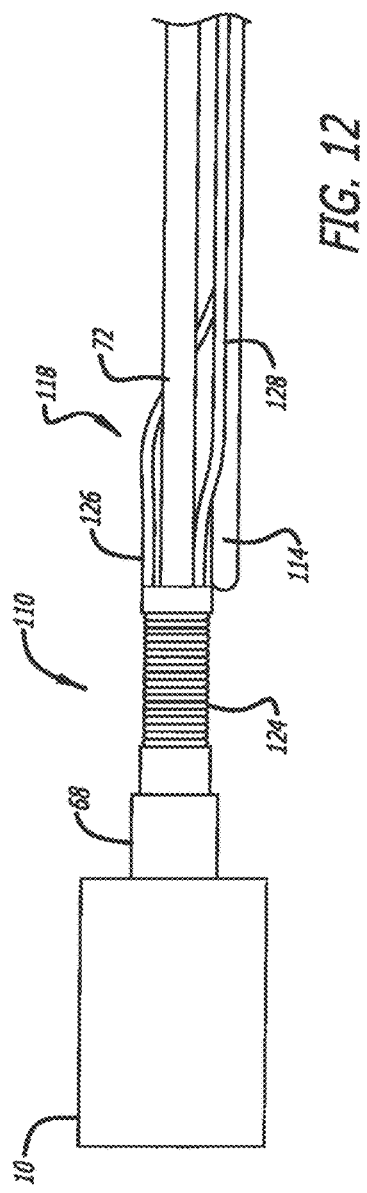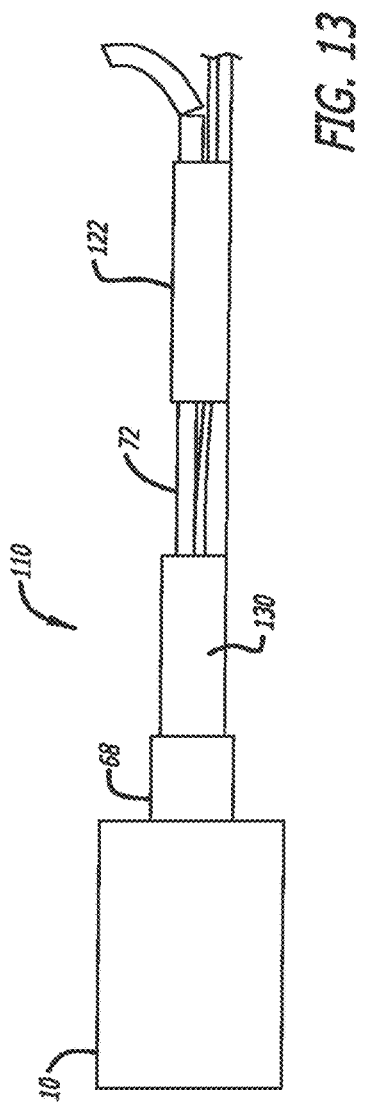

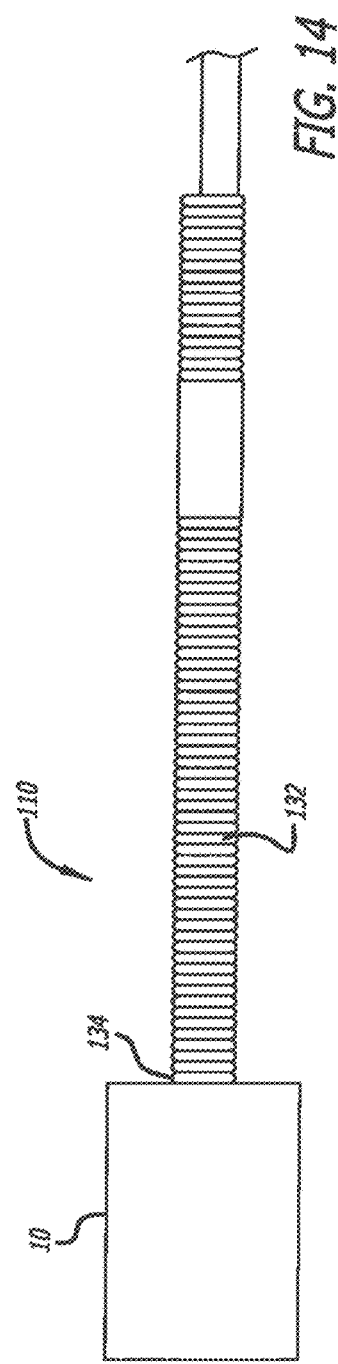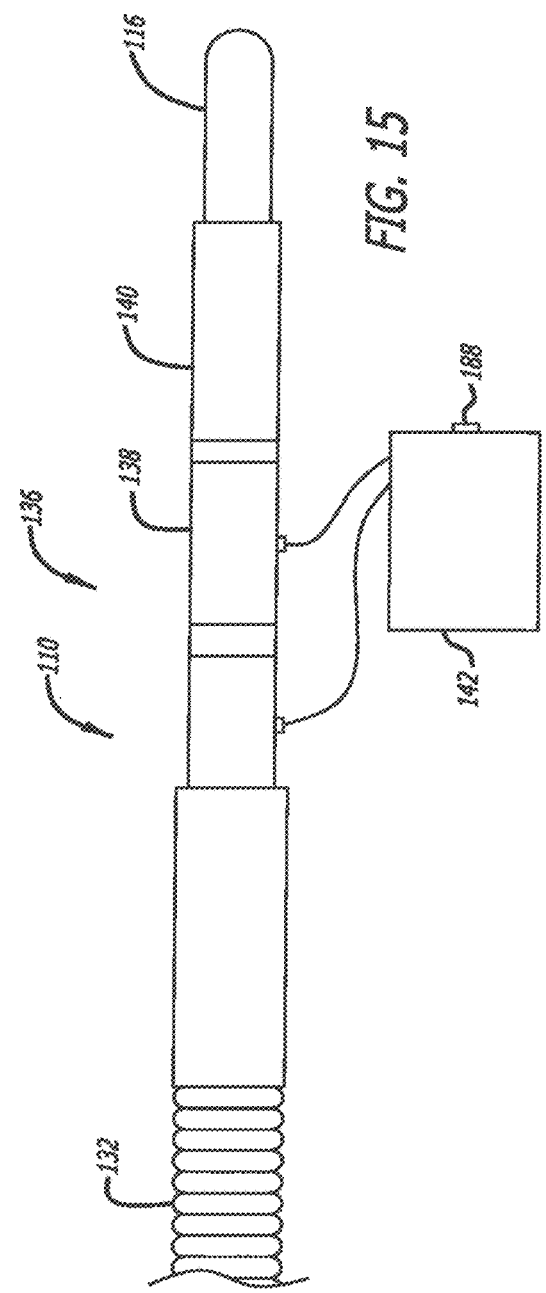

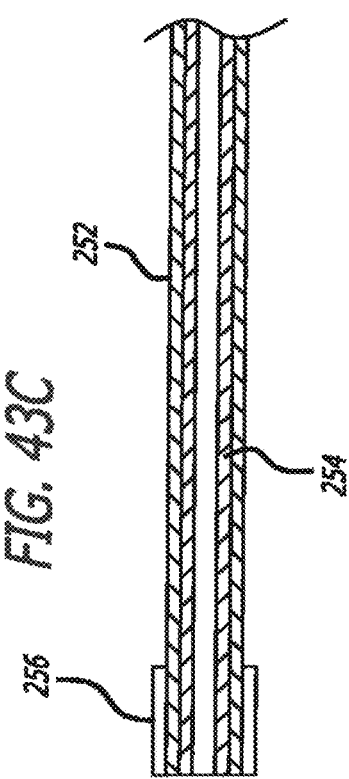
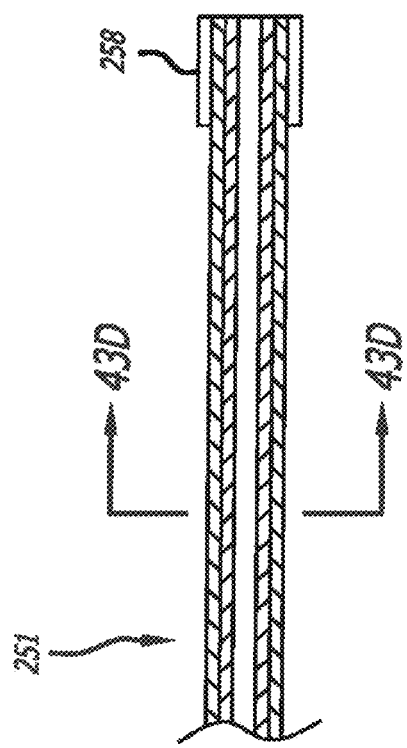
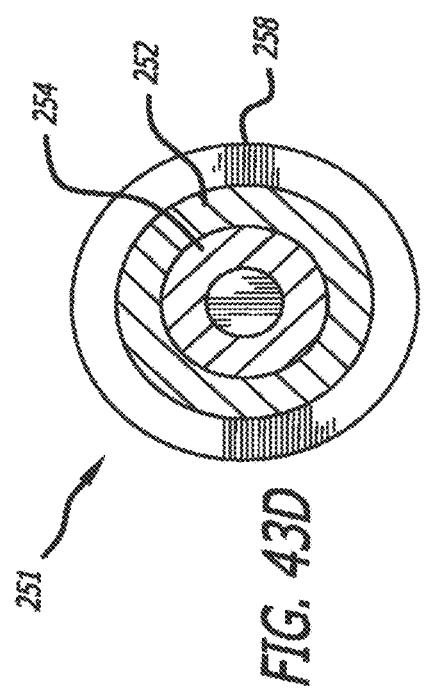

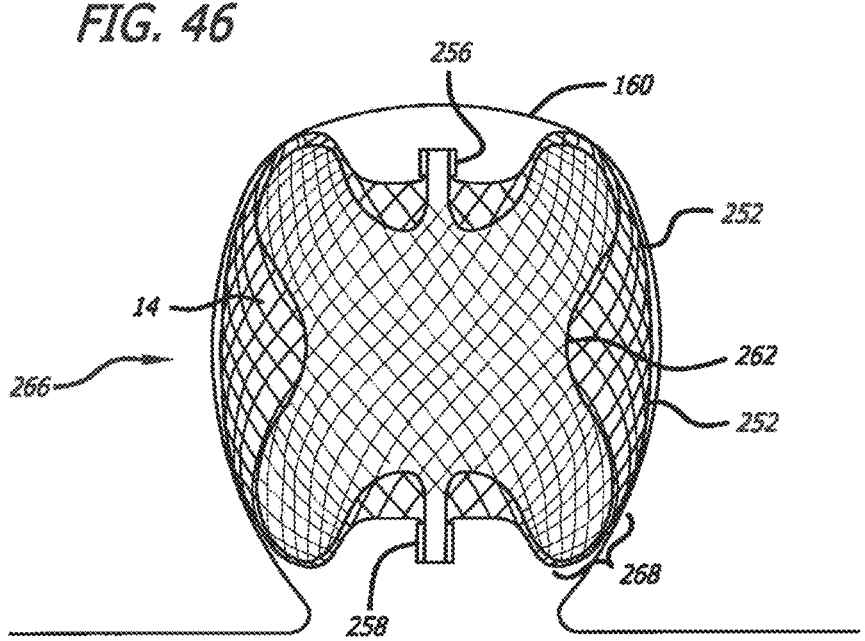

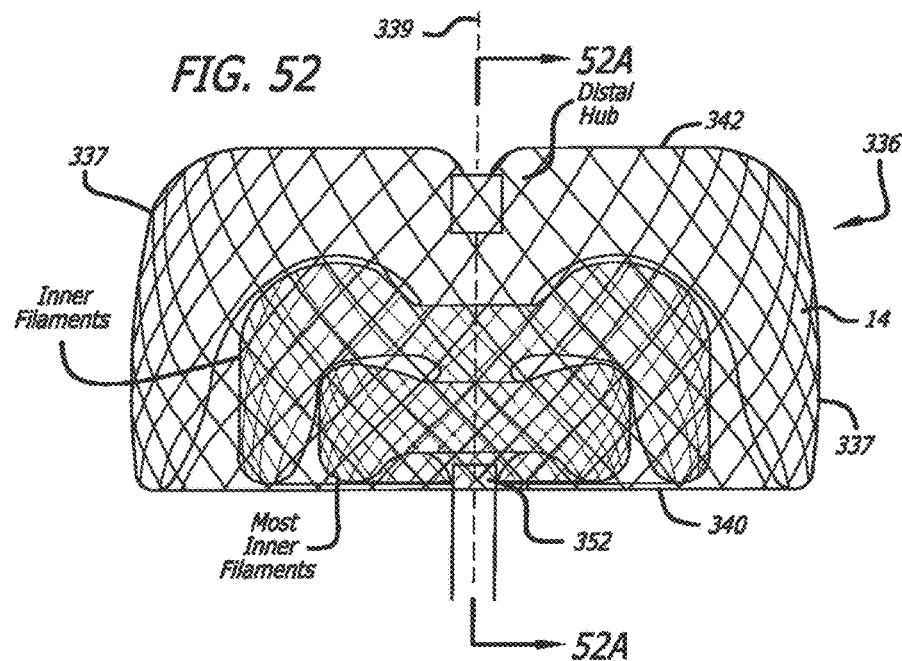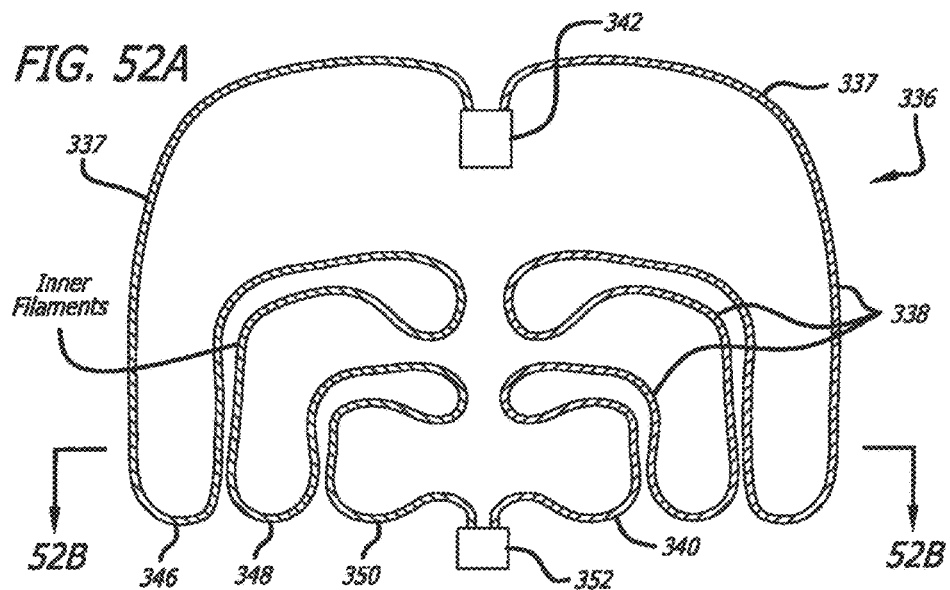

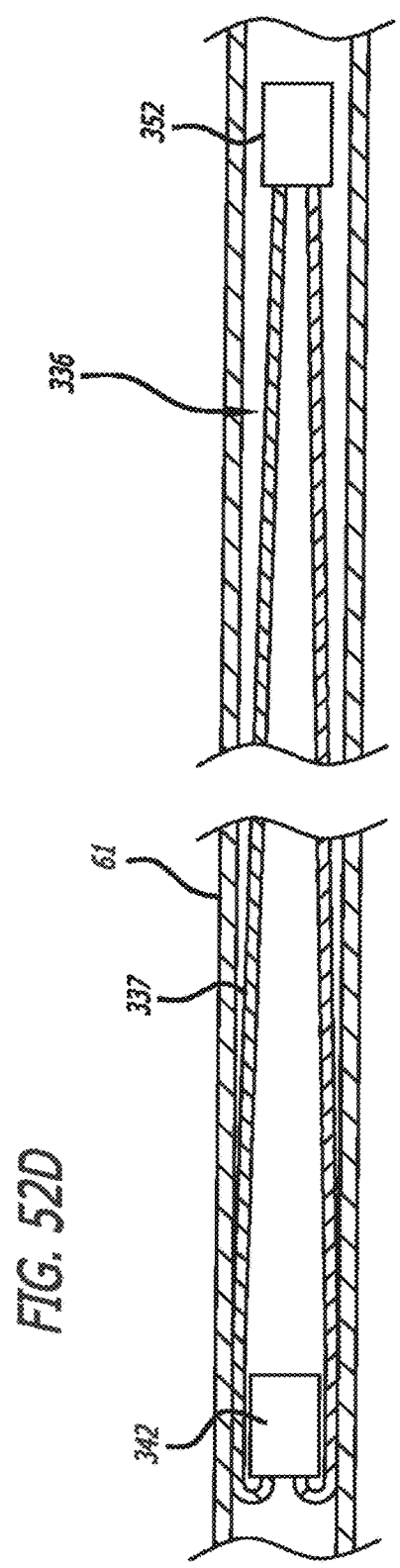

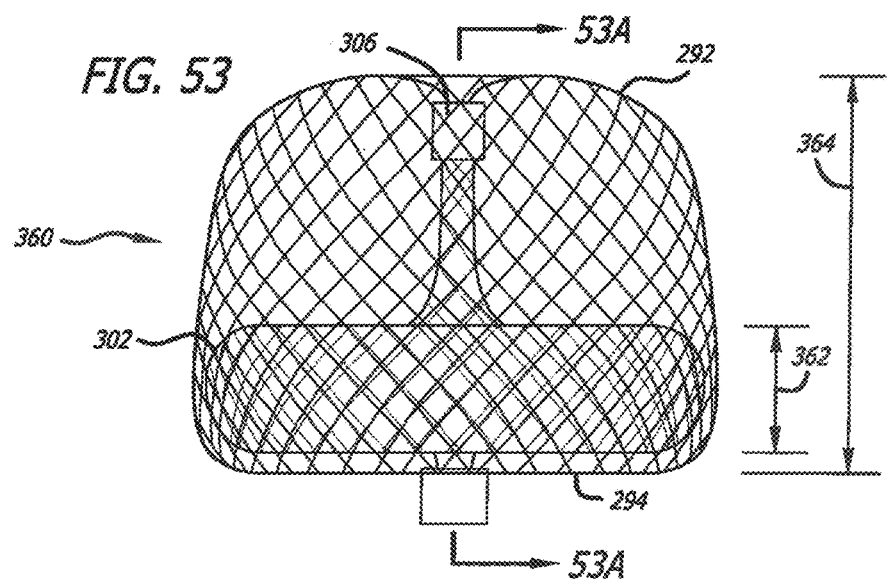
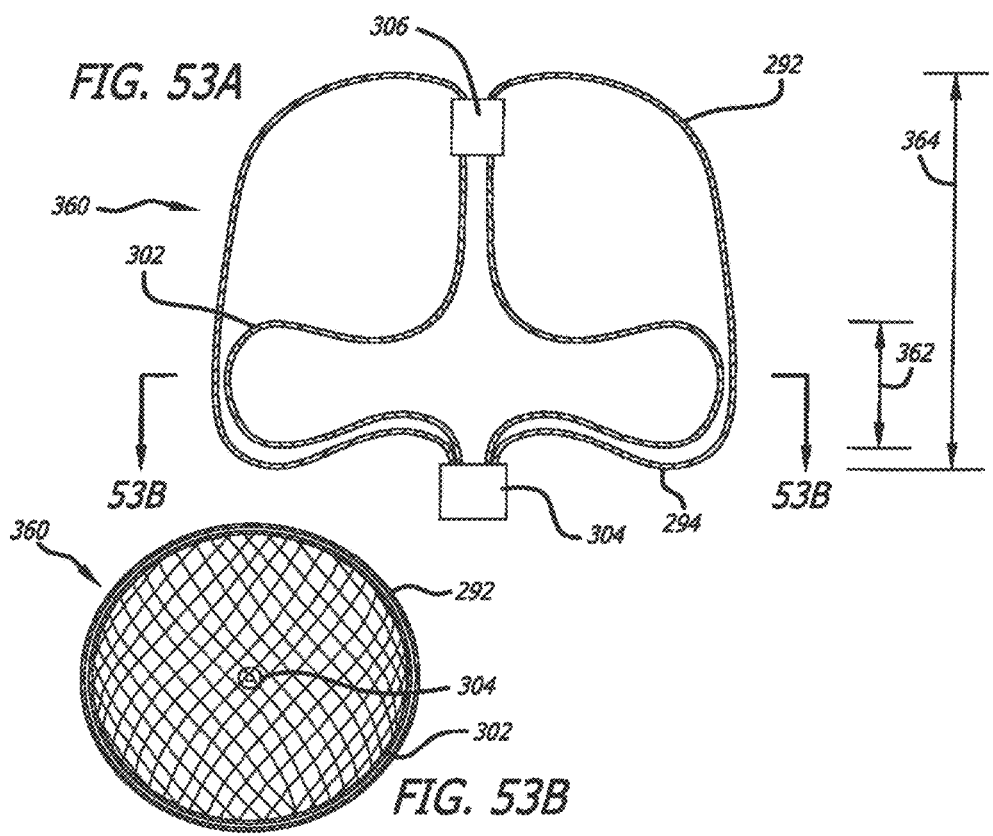

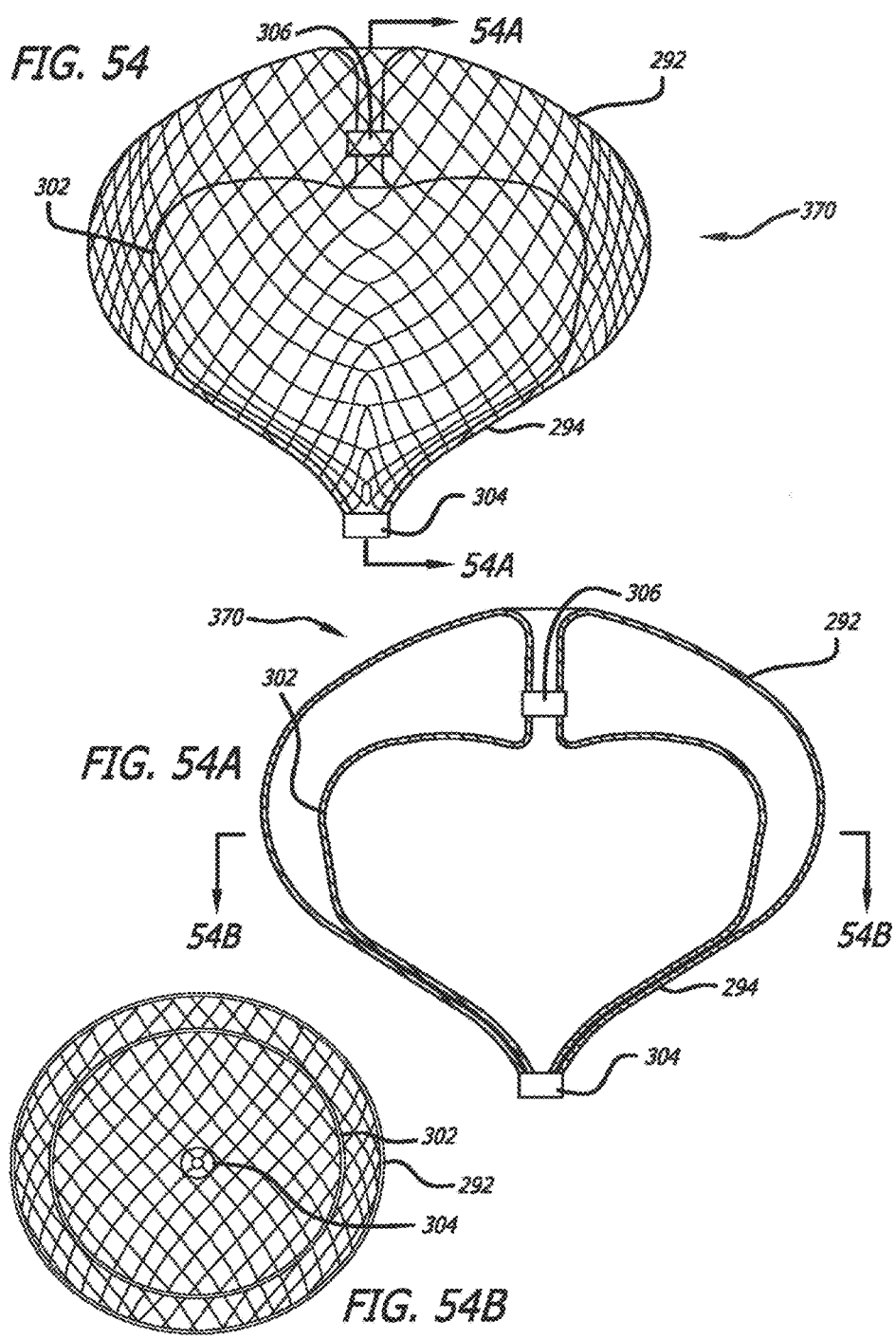

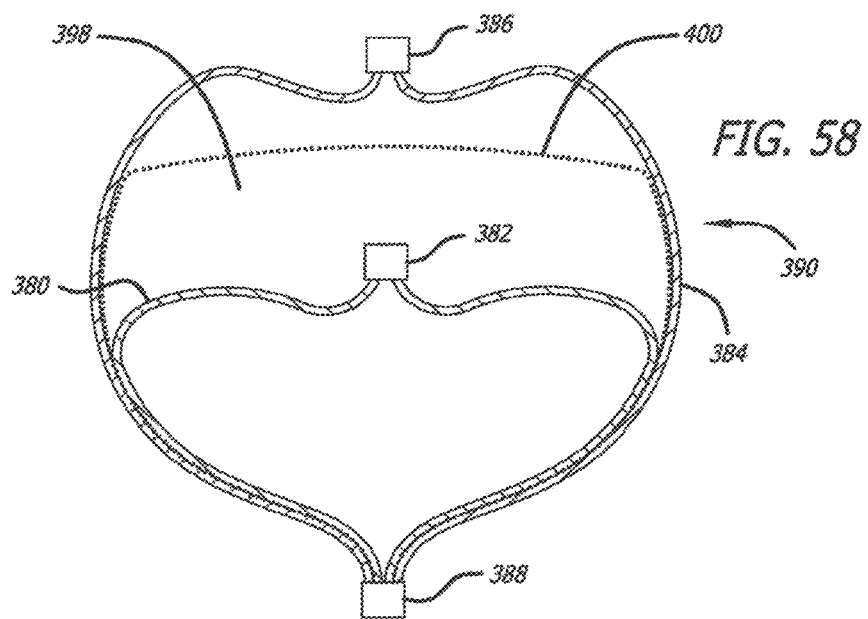
FIG. 58
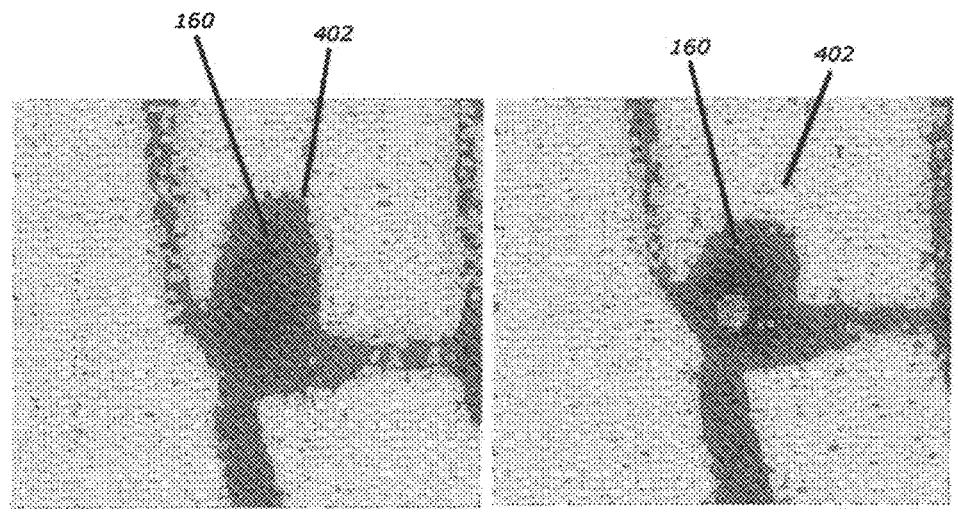
Pre-treatment Angiogram
FIG. 59A
10 minutes Post treatment
FIG. 59B

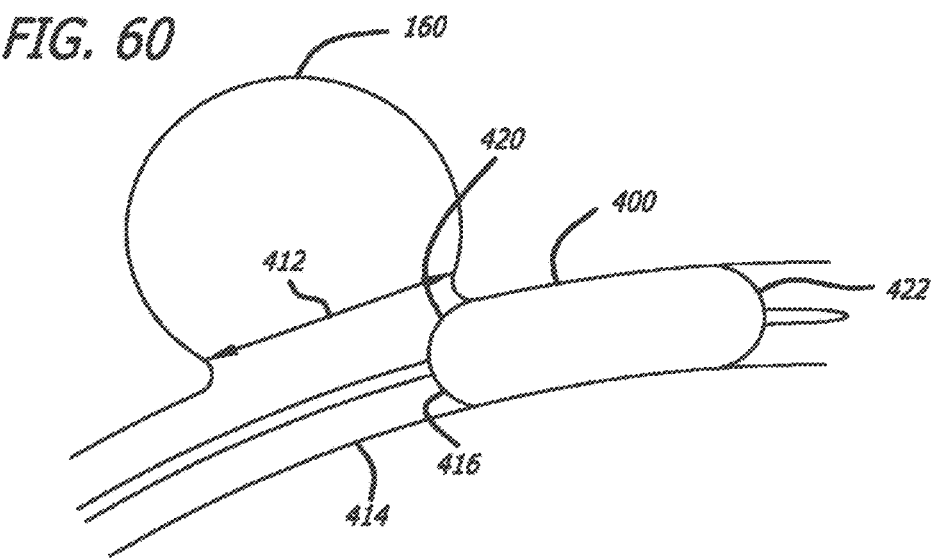
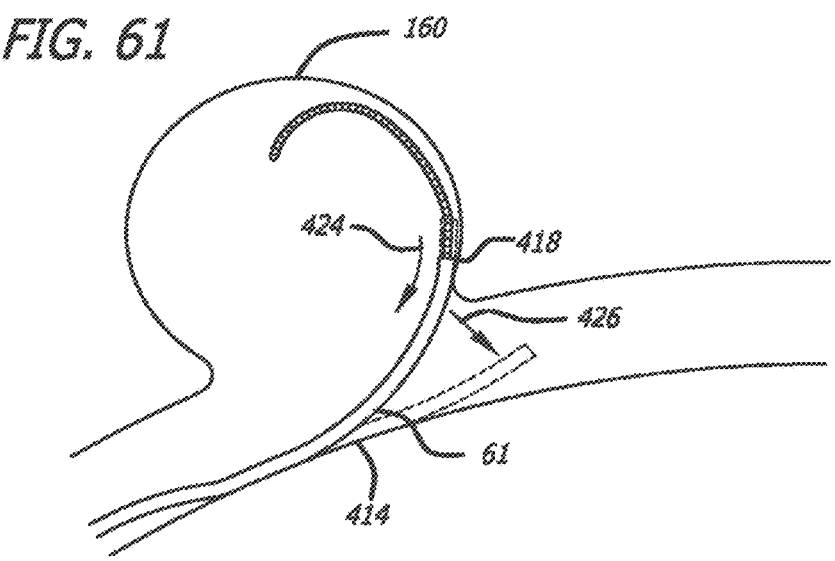

MULTIPLE LAYER FILAMENTARY DEVICES FOR TREATMENT OF VASCULAR DEFECTS

RELATED APPLICATIONS

This application is a continuation of U.S. Utility patent application Ser. No. 12/939,901, filed Nov. 4, 2010, by P. Marchand et al., titled "Multiple Layer Filamentary Devices for Treatment of Vascular Defects", which claims priority under 35 U.S.C. section 119(e) from U.S. Provisional Application No. 61/258,541, filed Nov. 5, 2009, by P. Marchand et al., titled "Multiple Layer Filamentary Devices for Treatment of Vascular Defects", U.S. Provisional Application No. 61/294,760, filed Jan. 13, 2010, by P. Marchand et al., titled "Multiple Layer Filamentary Devices for Treatment of Vascular Defects", and U.S. Provisional Application No. 61/334,130, filed May 12, 2010, by P. Marchand et al., titled "Multiple Layer Filamentary Devices for Treatment of Vascular Defects", each of which is incorporated by reference herein in its entirety. This application is also related to U.S. patent application Ser. No. 12/602,997, filed Jun. 3, 2008, by B. Cox et al., titled "Methods and Devices for Treatment of Vascular Defects", and U.S. patent application Ser. No. 12/434,465, filed May 1, 2009, by P. Marchand et al., titled "Filamentary Devices for Treatment of Vascular Defects", each of which is incorporated by reference herein in its entirety.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e. deliverable through a microcatheter and highly flexible) do not have the necessary rotational positioning capability. Another limitation of many aneurysm bridging devices described in the prior art is the poor flexibility.

Cerebral blood vessels are tortuous and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm. In addition, what has been needed are methods and devices suitable for blocking blood flow in cerebral aneurysms over an extended period of time without a significant risk of deformation, compaction or dislocation.

SUMMARY

Some embodiments of a device for treatment of a patient's vasculature include a self-expanding resilient permeable shell having a proximal end, a distal end, and a longitudinal axis. The permeable shell also includes a plurality of elongate resilient filaments with a woven structure secured relative to each other at proximal ends and distal ends thereof. The permeable shell has a radially constrained elongated state configured for delivery within a microcatheter with the thin woven filaments extending longitudinally from the proximal end to the distal end radially adjacent each other along a length of the filaments. The permeable shell also has an expanded relaxed state with a longitudinally shortened configuration relative to the radially constrained state with the woven filaments forming the self-expanding resilient permeable shell in a smooth path radially expanded from the longitudinal axis between the proximal end and distal end including a plurality of openings in the shell formed between the woven filaments, the largest of said openings being configured to allow blood flow through the openings at a velocity below a thrombotic threshold velocity. Thus, blood flow within the permeable shell may be substantially slowed to below the thrombogenic threshold velocity. For some embodiments, the permeable shell may have a globular shape in the expanded relaxed state. In some embodiments, the shell may have a generally cylindrical shape with either substantially flat or rounded ends. Some of these embodiments may also include an inner structure of filamentary members disposed within the resilient permeable shell. Unless otherwise stated, one or more of the features, dimensions, or materials of the various embodiments may be used in other similar embodiments discussed herein.

Some embodiments of a device for treatment of a patient's vasculature include a self-expanding resilient permeable shell having a proximal end, a distal end, and a longitudinal axis. The permeable shell may also include a plurality of elongate resilient filaments including large filaments and small filaments of at least two different transverse dimensions with a woven structure secured relative to each other at proximal ends and distal ends thereof. The permeable shell may also include a radially constrained elongated state configured for delivery within a microcatheter with the thin woven filaments extending longitudinally from the proximal end to the distal end radially adjacent each other along a length of the filaments. The permeable shell also has an expanded relaxed state with a globular and longitudinally shortened configuration relative to the radially constrained state with the woven filaments forming the self-expanding resilient permeable shell in a smooth path radially expanded from the longitudinal axis between the proximal end and distal end including a plurality of openings in the shell formed between the woven filaments. Some of these embodiments may also include an inner structure of filamentary members disposed within the resilient permeable shell.

Some embodiments of a device for treatment of a patient's vasculature include a self-expanding resilient permeable shell having a proximal end, a distal end, and a longitudinal axis. The permeable shell also includes a plurality of elongate resilient filaments including large filaments and small filaments of different transverse diameters with a woven structure secured relative to each other at proximal ends and distal ends thereof. The permeable shell may also include a radially constrained elongated state configured for delivery within a microcatheter with the woven filaments extending longitudinally from the proximal end to the distal end radially adjacent each other along a length of the filaments. The permeable shell also has an expanded relaxed state with a globular and longitudinally shortened configuration relative to the radially constrained state with a major transverse diameter, the woven filaments forming the self-expanding resilient permeable shell in a smooth path radially expanded from the longitudinal axis between the proximal end and distal end, and including a plurality of openings in the shell formed between the woven filaments. Some of these embodiments may also include an inner structure of filamentary members disposed within the resilient permeable shell. In addition, the permeable shell may have properties such that the diameter of the permeable shell in an expanded state, number and diameter of large filaments and number and diameter of small filaments are configured such that the permeable shell in an expanded state has a radial stiffness of about 0.014 pounds force (lbf) to about 0.284 lbf defined by the expression $(1.2 \times 10^6 \text{ lbf}/D^4)(N_1 d_1^4 + N_s d_s^4)$ where D is a diameter of the permeable shell in the expanded state in inches, $N_1$ is the number of large filaments in the permeable shell, $N_s$ is the number of small filaments in the permeable shell, $d_1$ is the diameter of the large filaments in inches, and $d_s$ is the diameter of the small filaments in inches. The equation above contemplates two wire sizes; however, the equation is also applicable to embodiments having one wire size in which case $d_1$ will be equal to $d_s$. Generally with respect to wire and filament sizes regarding transverse dimension or diameter, it may not be necessary in some cases for all wires or filaments to meet the parameters for the various relationships discussed herein. This may be particularly true where relatively large numbers of filaments are being used. In some cases, a filamentary structure may meet the relationship constraints discussed herein where the predominance of filaments of a permeable shell or inner structure meet a size constraint.

Some embodiments of a device for treatment of a patient's vasculature include a self-expanding resilient permeable shell having a proximal end, a distal end, and a longitudinal axis. The permeable shell also has a plurality of elongate resilient filaments including large filaments and small filaments of different transverse diameters with a woven structure secured relative to each other at proximal ends and distal ends thereof. The permeable shell may also include a radially constrained elongated state configured for delivery within a microcatheter with the thin woven filaments extending longitudinally from the proximal end to the distal end radially adjacent each other along a length of the filaments. The permeable shell has an expanded relaxed state with a globular and longitudinally shortened configuration relative to the radially constrained state with a major transverse diameter, the woven filaments forming the self-expanding resilient permeable shell in a smooth path radially expanded from the longitudinal axis between the proximal end and distal end, and including a plurality of openings in the shell formed between the woven filaments. Some of these embodiments may also include an inner structure of filamentary members disposed within the resilient permeable shell. The permeable shell may also be configured such that at least the distal end has a reverse bend in an everted recessed configuration such that the secured distal ends of the filaments are withdrawn axially within the nominal permeable shell structure in the expanded state. The permeable shell may further have properties such that the diameter of the permeable shell in an expanded state, number of all filaments and diameter of the small filaments are configured such that the maximum opening size of a portion of the permeable shell in an expanded state that spans a vascular defect opening or vascular defect neck is less than about 0.016 inches with the maximum pore or opening size defined by the expression $(1.7/N_T)(\pi D - N_T/2d_w)$ where D is a diameter of the permeable shell in the expanded state in inches, $N_T$ is the total number of filaments in the permeable shell, and $d_w$ is the diameter of the small filaments in inches. The pore size for an opening is defined herein by the largest circular shape that may be disposed within the opening of a braided filament structure.

Some embodiments of a device for treatment of a patient's vasculature include a self-expanding resilient permeable shell having a proximal end, a distal end, and a longitudinal axis. The permeable shell further includes a plurality of elongate resilient filaments including large filaments and small filaments of different transverse diameters with a woven structure secured relative to each other at proximal ends and distal ends thereof. The permeable shell may also have a radially constrained elongated state configured for delivery within a microcatheter with the woven filaments extending longitudinally from the proximal end to the distal end radially adjacent each other along a length of the filaments. The permeable shell also includes an expanded relaxed state with a globular and longitudinally shortened configuration relative to the radially constrained state with a major transverse diameter, the woven filaments forming the self-expanding resilient permeable shell in a smooth path radially expanded from the longitudinal axis between the proximal end and distal end, and including a plurality of openings in the shell formed between the woven filaments. Some of these embodiments may also include an inner structure of filamentary members disposed within the resilient permeable shell. The permeable shell may also be configured such that at least the distal end has a reverse bend in an everted recessed configuration such that the secured distal ends of the filaments are withdrawn axially within the nominal permeable shell structure in the expanded state.

In some embodiments, a distal end of the inner structure may terminate with a connection or hub at the proximal end of the structure. With an internal termination of the inner structure, the potential problem of length matching and buckling may be minimized due to the ability of the inner layer to collapse without affecting, or minimally affecting, the outer layer. In some embodiments, the collapsed length of the inner structure may be less than about 80% of the collapsed length of the outer structure. In some embodiments, the collapsed length of the inner structure may be about 40% to about 90% of the collapsed length of the outer permeable shell.

In some embodiments, the outer structure or shell may have a truncated sphere or generally heart-like cross-sectional shape. The proximal portion may be generally convex, hemispherical or semi-circular in cross section. These features allow the device to be placed into a saccular vascular site such as a cerebral aneurysm at an angled orientation relative to an axis of the aneurysm. The semi-circular or hemispherical proximal surface presents a relatively constant shape to the parent vessel irrespective of the angulation of the aneurysm axis.

In some embodiments, the inner structure may be formed such that at least about 80% of the volume of the inner structure is contained within the lower or more proximal half of the outer structure or shell volume. For some embodiments, the mesh density of the inner structure may be higher than a density of the mesh structure of the outer shell or structure. For some embodiments, the average wire diameter of the inner structure is less than about 75% of the average wire diameter of the outer structure. In some embodiments, the weighted average diameter by number of wires of a structure may be important. The weighted average may be defined by the equation: $N \times D = A_w$. In this equation, N is the number of wires, D is the wire diameter and $A_w$, is the weighted average diameter. Thus, a structure mesh formed of 36 wires with a diameter of 0.00125 inches and 108 wires with a diameter of 0.00075 inches would have a weighted average ($A_w$) of 0.126 inches. For some embodiments, the weighted average diameter of the inner structure may be less than about 75% of the weighted average diameter of the outer structure or permeable shell.

In some embodiments a device for treatment of a patient's vasculature includes a self-expanding resilient permeable structure having a proximal end, a distal end, and a longitudinal axis. The permeable structure has a radially constrained elongated state configured for delivery within a microcatheter. In an expanded relaxed state the permeable structure has a globular and longitudinally shortened configuration relative to the radially constrained state and extends along the longitudinal axis between the proximal end and distal ends. The permeable structure further includes a plurality of elongate resilient filaments secured relative to each other at either or both the proximal ends and distal ends of the structure. The filaments form a resilient permeable shell having proximal and distal ends and defining a cavity and at least one inner structure disposable within the cavity of the shell. The resilient filaments forming the shell and the at least one inner structure are contiguous with one another.

In some embodiments the filaments are woven and the filaments forming the self-expanding resilient permeable shell extend in a smooth path radially expanded from the longitudinal axis between the proximal end and distal end. The filaments form a plurality of openings between the woven filaments with the largest of said openings being configured to allow blood flow through the openings at a velocity below a thrombotic threshold velocity. In some embodiments, the inner structure, in an expanded state, may form a concave or convex outer surface relative to the shell.

In some embodiments, the inner structure passes through a cylindrical member or hub that is attached to the proximal end of the shell. In some embodiments including this feature, the shell and inner structure may be formed from a contiguous flexible elongate member, such as a tubular braid, that is inverted at one or more ends. The distal hub or marker may be placed on the portion of the filaments where they come together just below the inverted portion of the shell within the shell cavity. Various methods of connecting the shell filaments to the cylindrical member may be employed including welding, soldering and the like as described herein. In the embodiment shown, the shell and the inner filaments form different contours.

In some embodiments, the distal hub or marker may be positioned below the top or distal surface of the device at a distance from the most distal surface which is at least about 10% of the device height. In some embodiments, the distal hub or marker may be positioned just below the top or distal surface of the device at a distance which is less than about 10% of the device height. In some embodiments the filaments forming the permeable shell and the at least one inner structure may be inverted at least one of the ends of the structure, e.g., proximal or distal ends.

In some embodiments each of a plurality of inner structures may have an expanded diameter which differs from that of the other inner structures. In this configuration, a plurality of lobes may nest within each other to form the multiple radial layers or lobes in the relaxed state. In some embodiments, the inversion(s) may be at the proximal end. Thus, multiple radial layers may be achieved with a single contiguous structure. In some embodiments, the inner structure may comprise a plurality of inner structures formed integrally with one another. In some embodiments, the number of inversions may range from about 1 to about 5, normally 3. The lobes may be configured in a telescoping manner inside one another such that the lobe with a smaller diameter is disposable within a cavity formed by the lobe of the next highest diameter.

Each of the plurality of inner structures may have an unexpanded diameter which differs from the other inner structures. An inner structure with the smallest diameter may be disposable within a cavity of an inner structure having the next largest diameter with largest diameter inner structure being disposable within the shell cavity.

In any of the embodiments described herein, the inner or inverted structure(s) may provide a high surface area internal flow baffle. The multiple concentric radial layers may be particularly beneficial to slow blood flow in side-wall aneurysms. Blood that circulates in the aneurysm must flow through multiple layers of mesh to complete one circular flow path. Baffling of the circular flow provides flow disruption leading to rapid hemostasis and thrombosis.

In some embodiments, the total surface area of the inner or inverted structure(s) may be greater than about 100 mm$^2$. In some embodiments, the total surface area of the inner or inverted structure(s) may be between about 100 mm$^2$ and 500 mm$^2$ for each centimeter of the device's largest dimension. For example, with a 1.5 cm (diameter or length) device, the surface area of the inner or inverted structure(s) may be between about 150 mm$^2$ and 750 mm$^2$. Conversely, with a 0.5 cm (diameter or length) device, the surface area of the inner or inverted structure(s) may be between about 50 mm$^2$ and 250 mm$^2$.

In some embodiments, with the device for treatment of a patient's vasculature being under tension and in unexpanded configuration, the at least one inner structure and the shell extend along a common longitudinal axis and may be longitudinally spaced apart. In embodiments with a plurality of inner structures, with the device for treatment of a patient's vasculature being under tension and in unexpanded configuration, each of the plurality of the inner structures and the shell extend along a common longitudinal axis and are longitudinally spaced apart, with the smallest diameter inner structure being longitudinally the farthest away from the shell. In some cases, this configuration may allow for a telescoping configuration once the device is in an expanded state with each of the inner structures nesting within each other with the largest diameter inner structure nesting within and being closest to the shell or being disposable against the inner periphery of the shell as described above.

In any of the embodiments described herein, the optional inner or inverted structure(s), if present, may be substantially or completely within the lower portion of the permeable shell. In some embodiments, the height of the inner or inverted structure(s) may be less than about 30% of the shell height. In some embodiments, the height of the inner structure may be between about 30% and 90% of the height of the outer permeable shell. In any of the device embodiments described herein, the proximal surface of the permeable shell of the device for treatment of a patient's vasculature may be configured to be concave, convex, or conical in shape. In some instances, the conical type of proximal surface may provide a more natural diversion or branching of blood flow particularly for terminal aneurysms.

In some embodiments, the distal end of inner structure embodiments may terminate with a connection or hub. Thus, the inner structure may define a closed volume within the shell that is connected to the shell near the inner proximal surface of the shell. In some embodiments, the inner structure may not have an actual connection or hub but the inner structure filaments coalesce to form a substantially closed volume or shape. With an internal termination of the inner structure, a potential problem of length matching and buckling may be minimized due to the ability of the inner layer to collapse without affecting, or minimally affecting, the outer layer. In some embodiments, the inner structure forms a separate lobe from the shell. In some embodiments, the collapsed length of the inner structure may be less than about 80% of the collapsed length of the outer structure.

In some embodiments, the outer structure may have a truncated sphere or generally heart-like vertical cross-sectional shape. The proximal portion may be generally convex or semi-circular. These features may allow the device to be placed into a saccular vascular site such as a cerebral aneurysm at an angled orientation relative to an axis of the aneurysm. The semi-circular proximal surface presents a relatively constant shape to the parent vessel irrespective of the angulation of the device axis.

In some embodiments, the inner structure may be formed such that at least about 80% of the volume of the inner structure is contained within the lower or more proximal half of the outer structure or shell volume. In some embodiments, at least about 80% of the volume of the inner structure may be contained within a lower or more proximal 80% of the volume of the outer structure or shell. For some embodiments, the mesh density of the inner structure may be higher than a density of the mesh structure of the outer shell or structure. In some embodiments, the inner structure may be substantially or entirely within the proximal or lower 80% of the outer shell volume.

In some cases, and inner structure, occupying the lower portion of an interior volume of the outer shell may provide rapid progression of thrombosis particularly in the distal portion of an aneurysm. In some instances, this configuration may provide protection of the distal "dome" portion of an aneurysm where it is generally thought to be the weakest and most prone to rupture. Thus, embodiments with proximal inner structures may provide a method of rapidly occluding a distal portion of an aneurysm which may be visible under angiography.

Inner structure embodiments may be formed in some cases by braiding, weaving, or other filament interlacing techniques described herein similar to that used for formation of the permeable shell or any other suitable techniques used for medical textiles and intravascular implants. Alternatively, a filament may be merely twisted or allowed to form a random mesh of filaments. It may be heat set as described herein and by methods similar to that used to form the shell or it may not be heat treated beyond any heat setting done when the filaments are formed. Inner structure filament embodiments may be made from metals, polymers or composites thereof. In some embodiments, the filaments are formed of materials that can withstand heat treatment of at least about 450° C. In some embodiments, some of the filaments may be formed of an aramide fiber such as poly paraphenylene terephthalamide available under the trade name Kevlar. In some embodiments, the inner structure filamentary members may be wires with a diameter between about 10 microns (0.0004 inches) and about 30 microns (0.0012 inches). Any of the inner structure embodiments discussed herein may include materials, coatings that release elements or chemicals that promote thrombosis and thrombus formation. Any of the inner structure embodiments discussed herein may also be impregnated with particles or molecules that release elements or chemicals that promote thrombosis and thrombus formation.

Some permeable shell embodiments may also have properties such that the diameter of the permeable shell in an expanded state, number and diameter of large filaments and number and diameter of small filaments are configured such that the permeable shell in a constrained state has an outer transverse diameter of less than about 0.04 inches defined by the expression $1.48\ ((N_1 d_1^2 + N_s d_s^2))^{1/2}$ where $N_1$ is the number of large filaments in the permeable shell, $N_s$ is the number of small filaments in the permeable shell, $d_1$ is the diameter of the large filaments in inches, and $d_s$ is the diameter of the small filaments in inches.

The various components and or elements of some of the embodiments discussed herein may have same or similar dimensions, materials, and/or configurations of those of the other embodiments.

BRIEF DESCRIPTION OF THE DRAWINGS

FIG. 1 is an elevation view of an embodiment of a device for treatment of a patient's vasculature and a plurality of arrows indicating inward radial force.

FIG. 2 is an elevation view of a beam supported by two simple supports and a plurality of arrows indicating force against the beam.

FIG. 7 is an enlarged view of the woven filament structure taken from the encircled portion 7 shown in FIG. 5.

FIG. 8 is an enlarged view of the woven filament structure taken from the encircled portion 8 shown in FIG. 6.

FIG. 11 is an elevation view in partial section of a distal end of a delivery catheter with the device for treatment of a patient's vasculature of FIG. 3 disposed therein in a collapsed constrained state.

FIG. 12 is an elevation view of a distal portion of a delivery device or actuator showing some internal structure of the device.

FIG. 13 is an elevation view of the delivery device of FIG. 12 with the addition of some tubular elements over the internal structures.

FIG. 14 is an elevation view of the distal portion of the delivery device of FIG. 13 with an outer coil and marker in place.

FIG. 15 is an elevation view of a proximal portion of the delivery device.

FIG. 43C is a sectional view of the device of FIG. 43A in an elongated constrained state illustrating the substantially equal longitudinal length of the permeable shell and inner structure in the elongated constrained state.

FIG. 43D is a transverse sectional view of the device of FIG. 43C taken along lines 43D-43D of FIG. 43C.

FIG. 46 is an elevation view in section that illustrates an embodiment of a device for treatment of a patient's vasculature disposed within an aneurysm.

FIG. 52 is an elevation view of an embodiment of a device for treatment of a patient's vasculature.

FIG. 52A shows the embodiment of the device for treatment of a patient's vasculature shown in FIG. 52 in partial section and in a relaxed expanded state.

FIG. 52D illustrates the device of FIG. 52 in a longitudinally extended state.

FIG. 53 is an elevation view of an embodiment of a device for treatment of a patient's vasculature.

FIG. 53A shows the device of FIG. 53 in partial section.

FIG. 53B is a cross-sectional view of the embodiment of FIG. 53A taken along lines 53B-53B of FIG. 53A.

FIG. 54 is an elevation view of an embodiment of a device for treatment of a patient's vasculature.

FIG. 54A shows the device embodiment of FIG. 54 in partial section.

FIG. 54B is a cross-sectional view of the embodiment of FIG. 54A taken along lines 54B-54B of FIG. 54A.

FIG. 58 is an elevation view in partial section of an embodiment of a device for treatment of a patient's vasculature.

FIG. 59A represents the image of an angiogram depicting an aneurysm prior to treatment.

FIG. 59B is depicts the aneurysm of FIG. 59A ten (10) minutes post-treatment.

FIG. 60 illustrates an aneurysm in section with a deflection device embodiment disposed in the native vessel adjacent the aneurysm in an inflated expanded state.

FIG. 61 shows the aneurysm of FIG. 60 with a distal end of a microcatheter and a distal end of a guidewire disposed within an interior volume of the aneurysm.

DETAILED DESCRIPTION

Figure 3:
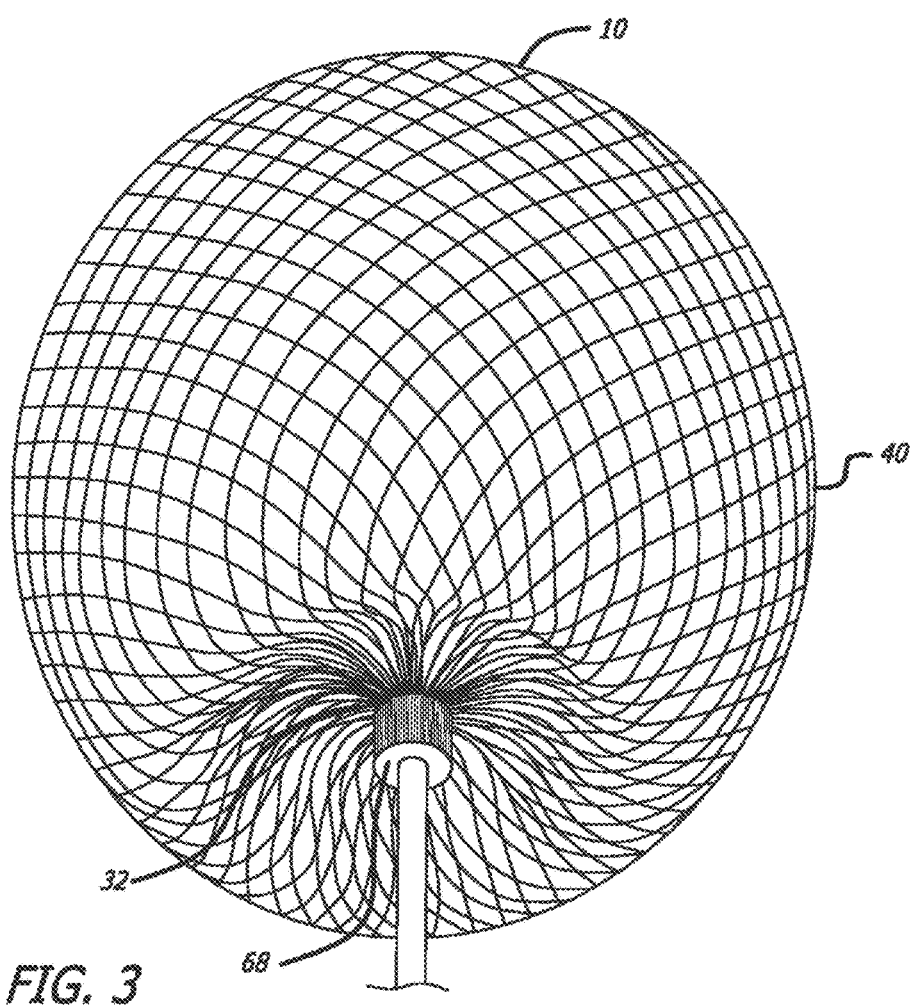
FIG. 3 is a bottom perspective view of an embodiment of a device for treatment of a patient's vasculature.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician. Unless otherwise stated, one or more of the features, dimensions, or materials of the various embodiments may be used in other similar embodiments discussed herein.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, a permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation. In addition, a portion of the permeable shell that is initially permeable or semi-permeable to blood flow may become substantially non-permeable or completely non-permeable due to thrombus formation on the filaments of the device. In some cases, thrombus formation on filaments of the permeable shell or any other portion of the device may serve to decrease the pore size between the filaments or close off the pores of the permeable shell completely.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile which is small enough to allow insertion through an inner lumen of a microcatheter. A device with a radial stiffness below a certain threshold may be unstable and may be at higher risk of undesired movement and embolization of the wrong region of the vasculature in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed.

For some embodiments, it may be desirable to use filaments having two or more different diameters or transverse dimensions to form a permeable shell in order to produce a desired configuration as discussed in more detail below. The radial stiffness of a two-filament (two different diameters) woven device may be expressed as a function of the number of filaments and their diameters, as follows:

$$S_{radial} = (1.2 \times 10^6 \text{ lbf}/D^4)(N_1 d_1^4 + N_s d_s^4)$$

where $S_{radial}$ is the radial stiffness in pounds force (lbf),
D is the Device diameter (transverse dimension),
$N_1$ is the number of large filaments,
$N_s$ is the number of small filaments,
$d_1$ is the diameter of the large filaments in inches, and
$d_s$ is the diameter of the small filaments in inches.

Using this expression, the radial stiffness, $S_{radial}$ may be between about 0.014 and 0.284 lbf force for some embodiments of particular clinical value.

The maximum pore size in a portion of a device that spans a neck or opening of a vascular defect desirable for some useful embodiments of a woven wire device for treatment of a patient's vasculature may be expressed as a function of the total number of all filaments, filament diameter and the device diameter. The difference between filament sizes where two or more filament diameters or transverse dimensions are used, may be ignored in some cases for devices where the filament size(s) are very small compared to the device dimensions. For a two-filament device, i.e., a device made from filaments of two different sizes, the smallest filament diameter may be used for the calculation. Thus, the maximum pore size for such embodiments may be expressed as follows:

$$P_{max} = (1.7/N_T)(\pi D - (N_T d_w/2))$$

where $P_{max}$ is the average pore size,
D is the Device diameter (transverse dimension),
$N_T$ is the total number of all filaments, and
$d_w$ is the diameter of the filaments (smallest) in inches.

Using this expression, the maximum pore size, $P_{max}$, of a portion of a device that spans an opening of a vascular defect or neck, or any other suitable portion of a device, may be less than about 0.016 inches or about 400 microns for some embodiments. In some embodiments the maximum pore size for a defect spanning portion or any other suitable portion of a device may be less than about 0.012 inches or about 300 microns.

The collapsed profile of a two-filament (profile having two different filament diameters) woven filament device may be expressed as the function:

$$P_c = 1.48((N_1 d_1^2 + N_s d_s^2))^{1/2}$$

where $P_c$ is the collapsed profile of the device,
$N_1$ is the number of large filaments,
$N_s$ is the number of small filaments,
$d_1$ is the diameter of the large filaments in inches, and
$d_s$ is the diameter of the small filaments in inches.

Using this expression, the collapsed profile $P_c$ may be less than about 1.0 mm for some embodiments of particular clinical value. In some embodiments of particular clinical value, the device may be constructed so as to have all three factors ($S_{radial}$, $P_{max}$ and $P_c$) above within the ranges discussed above; $S_{radial}$ between about 0.014 lbf and 0.284 lbf, P. less than about 300 microns and $P_c$ less than about 1.0 mm, simultaneously. In some such embodiments, the device may be made to include about 70 filaments to about 300 filaments. In some cases, the filaments may have an outer transverse dimension or diameter of about 0.0004 inches to about 0.002 inches.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments become correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as shown by the arrows 18 in the figure. It can be seen from the equation below for the deflection of a beam with two simple supports 20 and a distributed load that the deflection is a function of the length, L to the $4^{th}$ power:

$$\text{Deflection of Beam} = 5FL^4/384EI$$

where F=force,
L=length of beam,
E=Young's Modulus, and
I=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile which is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$$I = \pi d^4/64$$

where d is the diameter of the wire or filament.

Since the moment of inertia is a function of filament diameter to the fourth power, a small change in the diameter greatly increases the moment of inertia. Thus, a small change in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. Some structures may use filaments having a transverse dimension of up to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches. As discussed generally above, it may not always be necessary for all wires or filaments to meet the parameters for the various relationships discussed herein. This may be particularly true where relatively large numbers of filaments are being used for a distinct structure. In some cases, a filamentary structure may meet the relationship constraints discussed herein where the predominance of filaments of a permeable shell or inner structure meet a size constraint.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three dimensional shapes such as discussed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7 and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIGS. 11-15.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
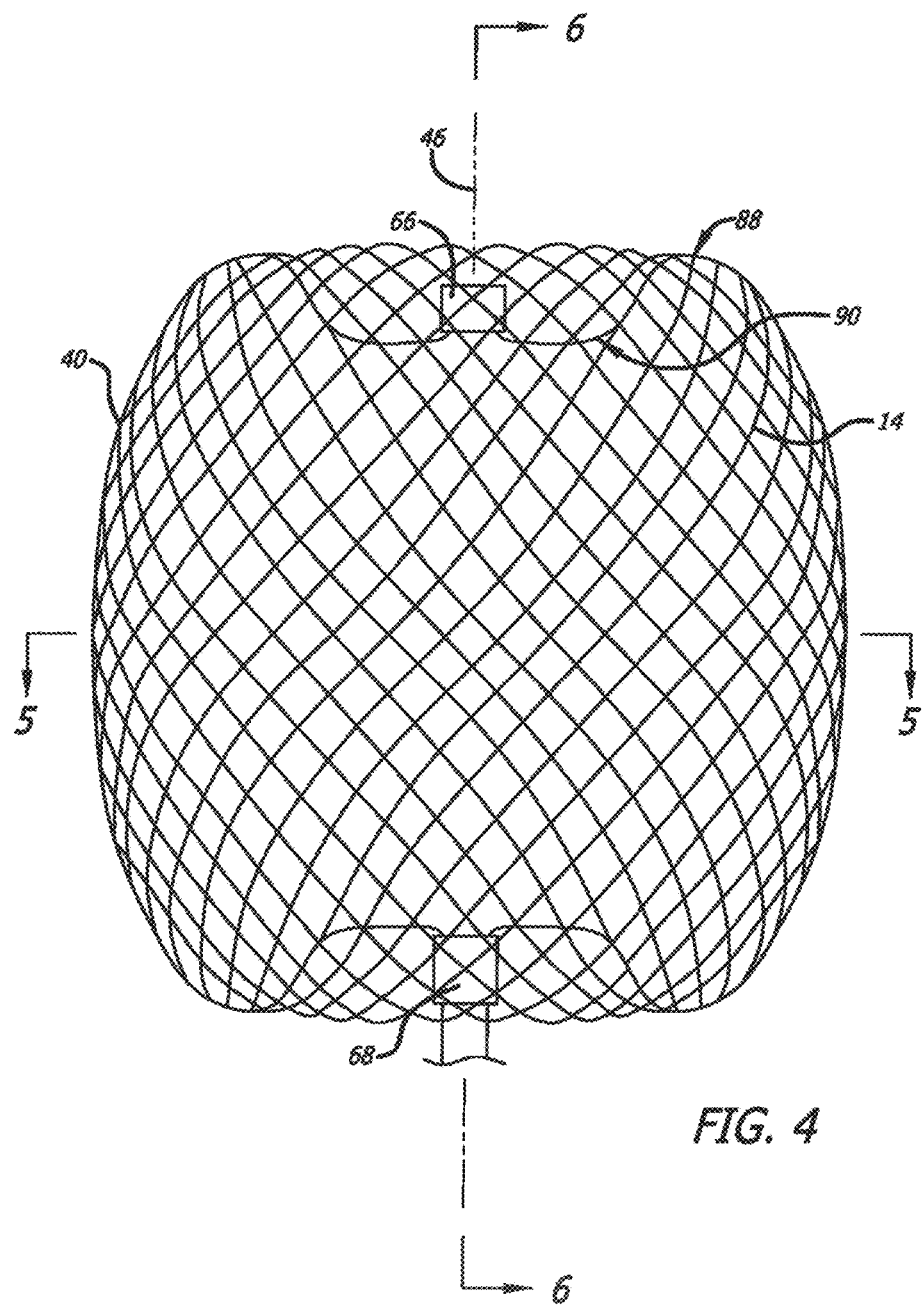
FIG. 4 is an elevation view of the device for treatment of a patient's vasculature of FIG. 3.
Figure 5:
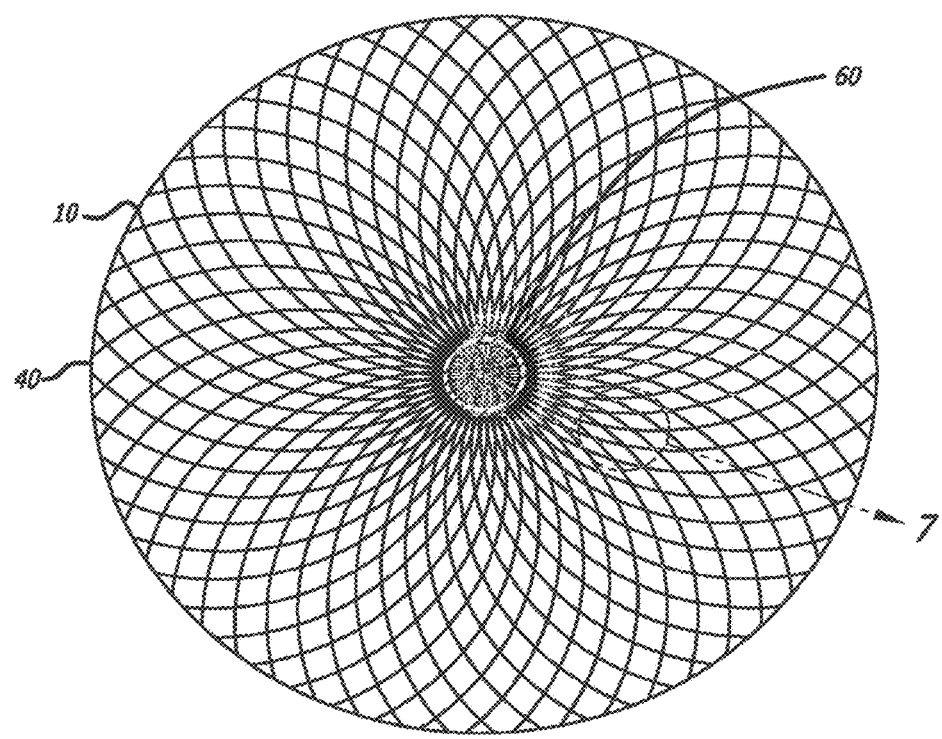
FIG. 5 is a transverse cross sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 110 of a delivery system 112 disposed at the proximal hub 68 of the device 10.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
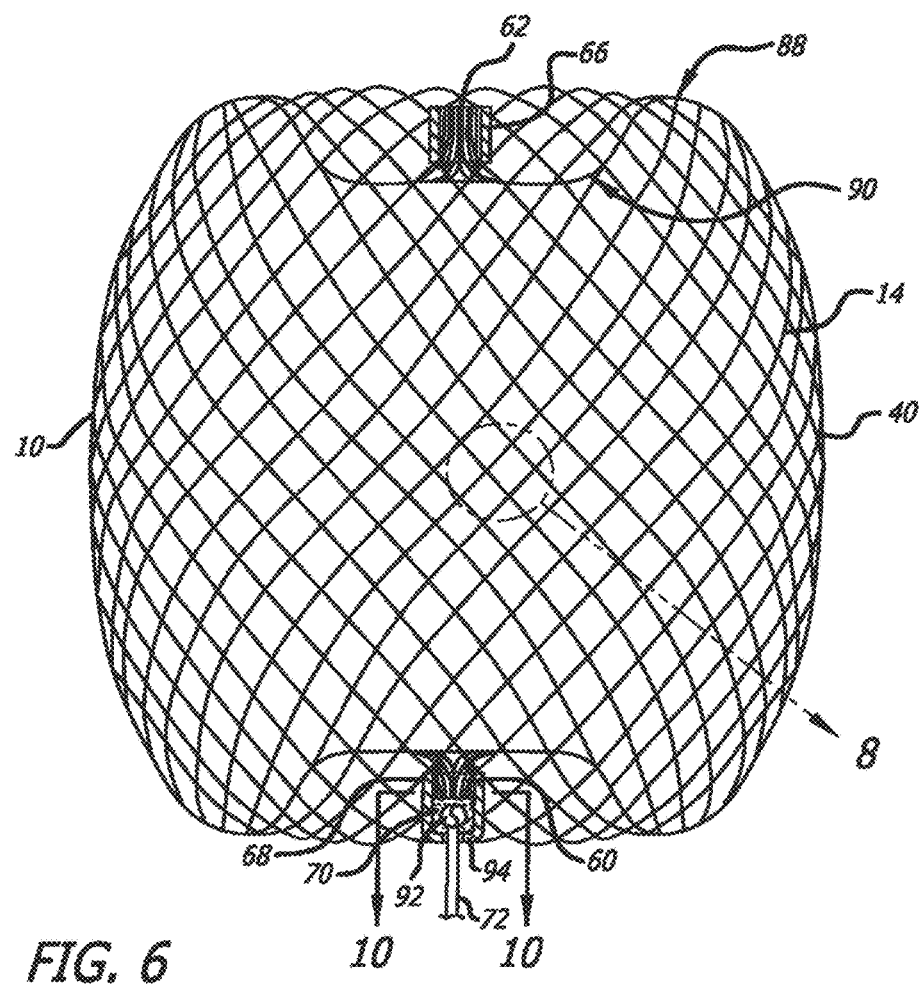
FIG. 6 shows the device of FIG. 4 in longitudinal section taken along lines 6-6 in FIG. 4.
Figure 9:
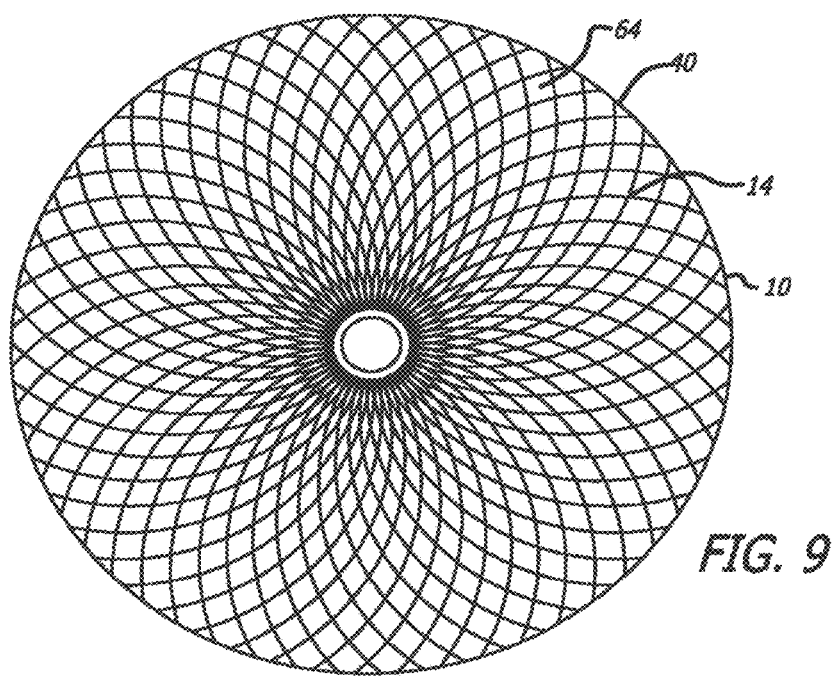
FIG. 9 is a proximal end view of the device of FIG. 3.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
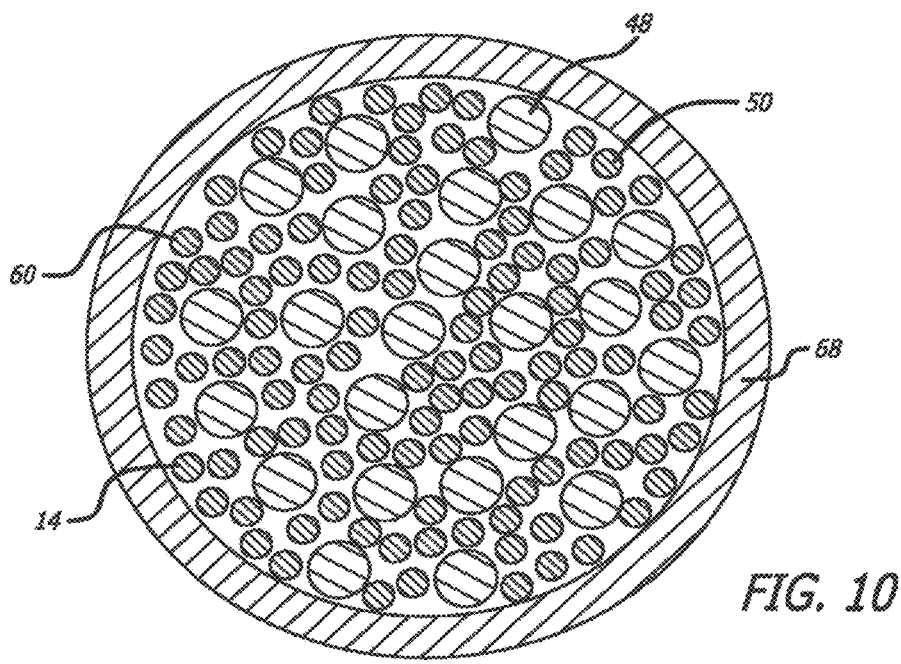
FIG. 10 is a transverse sectional view of a proximal hub portion of the device in FIG. 6 indicated by lines 10-10 in FIG. 6.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 110 used to deploy the device 10 as shown in FIG. 11 and FIGS. 23-26. FIG. 10 also shows the large filaments 48 and small filaments 50 disposed within and constrained by the proximal hub 68 which may be configured to secure the large and small filaments 48 and 50 in place relative to each other within the outer ring of the proximal hub 68.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Referring to FIGS. 12-15, a delivery apparatus embodiment 110 of the delivery system 112 of FIG. 11 is shown in more detail. The apparatus 110 includes an elongate core wire 114 that extends from a proximal end 116 of the apparatus 110 to a distal section 118 of the apparatus 110 as shown in FIG. 12. The core wire 114 is configured to provide sufficient column strength to push a constrained device 10 for treatment of a patient's vasculature through an inner lumen 120 of the microcatheter 61 of the delivery system 112 as shown in FIG. 11. The core wire 114 also has sufficient tensile strength to withdraw or proximally retract the device 10 from a position outside the microcatheter 61 and axially within the inner lumen 120 of the microcatheter 61. The tether 72 that extends proximally from the proximal hub 68 is secured to the distal end of the core wire 114 with a length of shrinkable tubing 122 that is disposed over a portion of the tether 72 and a distal section of the core wire 114 and shrunk over both as shown in FIG. 13, although any other suitable means of securement may be used.

A heater coil 124 electrically coupled to a first conductor 126 and a second conductor 128 is disposed over a distal most portion of the tether 72. The heater coil 124 may also be covered with a length of polymer tubing 130 disposed over the heater coil 124 distal of the heat shrink tubing 122 that serves to act as a heat shield and minimizes the leakage of heat from the heater coil 124 into the environment, such as the patient's blood stream, around the delivery apparatus 110. Once the heat shrink tubing 122 and insulating polymer tubing 130 have been secured to the distal section 118 of the apparatus 110, the proximal portion of the tether 72 disposed proximal of the heat shrink tubing 122 may be trimmed as shown in FIG. 13. An over coil 132 that extends from a distal end 134 of the delivery apparatus 110 to a proximal section 136 of the apparatus 110 may then be disposed over the heater coil 124, core wire 114, tether 72, first conductor 126 and second conductor 128 to hold these elements together, produce a low friction outer surface and maintain a desired flexibility of the delivery apparatus 110. The proximal section 136 of the apparatus 110 includes the proximal terminus of the over coil 132 which is disposed distal of a first contact 138 and second contact 140 which are circumferentially disposed about the proximal section 136 of the core wire 114, insulated therefrom, and electrically coupled to the first conductor 126 and second conductor 128, respectively as shown in FIG. 15.

The heater coil 124 may be configured to receive electric current supplied through the first conductor 126 and second conductor 128 from an electrical energy source 142 coupled to the first contact 138 and second contact 140 at the proximal section 136 of the apparatus 110. The electrical current passed through the heater coil 124 heats the heater coil to a temperature above the melting point of the tether material 72 so as to melt the tether 72 and sever it upon deployment of the device 10.

Embodiments of the delivery apparatus 110 may generally have a length greater than the overall length of a microcatheter 61 to be used for the delivery system 112. This relationship allows the delivery apparatus 110 to extend, along with the device 10 secured to the distal end thereof, from the distal port of the inner lumen 120 of the microcatheter 61 while having sufficient length extending from a proximal end 150 of the microcatheter 61, shown in FIG. 17 discussed below, to enable manipulation thereof by a physician. For some embodiments, the length of the delivery apparatus 110 may be about 170 cm to about 200 cm. The core wire 114 may be made from any suitable high strength material such as stainless steel, NiTi alloy, or the like. Embodiments of the core wire 114 may have an outer diameter or transverse dimension of about 0.010 inch to about 0.015 inch. The over coil 132 may have an outer diameter or transverse dimension of about 0.018 inch to about 0.03 inch. Although the apparatus embodiment 110 shown in FIGS. 12-15 is activated by electrical energy passed through a conductor pair, a similar configuration that utilizes light energy passed through a fiber optic or any other suitable arrangement could be used to remotely heat a distal heating member or element such as the heater coil 124 to sever the distal portion of the tether 72. In addition, other delivery apparatus embodiments are discussed and incorporated herein that may also be used for any of the device embodiments 10 for treatment of a patient's vasculature discussed herein.

Other delivery and positioning system embodiments may provide for the ability to rotate a device for treatment of a patient's vasculature in-vivo without translating torque along the entire length of the delivery apparatus. Some embodiments for delivery and positioning of devices 10 are described in co-owned International PCT Patent Application No. PCT/US2008/065694 incorporated above. The delivery and positioning apparatus may include a distal rotating member that allows rotational positioning of the device. The delivery and positioning apparatus may include a distal rotating member which rotates an implant in-vivo without the transmission of torque along the entire length of the apparatus. Optionally, delivery system may also rotate the implant without the transmission of torque in the intermediate portion between the proximal end and the distal rotatable end. The delivery and positioning apparatus may be releasably secured to any suitable portion of the device for treatment of a patient's vasculature.

Device embodiments discussed herein may be releasable from any suitable flexible, elongate delivery apparatus or actuator such as a guidewire or guidewire-like structure. The release of device embodiments from such a delivery apparatus may be activated by a thermal mechanism, as discussed above, electrolytic mechanism, hydraulic mechanism, shape memory material mechanism, or any other mechanism known in the art of endovascular implant deployment.

Embodiments for deployment and release of therapeutic devices, such as deployment of embolic devices or stents within the vasculature of a patient, may include connecting such a device via a releasable connection to a distal portion of a pusher or other delivery apparatus member. The therapeutic device 10 may be detachably mounted to the distal portion of the apparatus by a filamentary tether 72, string, thread, wire, suture, fiber, or the like, which may be referred to above as the tether. The tether 72 may be in the form of a monofilament, rod, ribbon, hollow tube, or the like. Some embodiments of the tether may have a diameter or maximum thickness of between about 0.05 mm and 0.2 mm. The tether 72 may be configured to be able to withstand a maximum tensile load of between about 0.5 kg and 5 kg. For some embodiments, due to the mass of the device 10 being deployed which may be substantially greater than some embolic devices, some known detachment devices may lack sufficient tensile strength to be used for some embodiments discussed herein. As such, it may be desirable to use small very high strength fibers for some tether embodiments having a "load at break" greater than about 15 Newtons. For some embodiments, a tether made from a material known as Dyneema Purity available from Royal DSM, Heerlen, Netherlands may be used.

The tether 72 may be severed by the input of energy such as electric current to a heating element causing release of the therapeutic device. For some embodiments, the heating element may be a coil of wire with high electrical resistivity such as a platinum-tungsten alloy. The tether member may pass through or be positioned adjacent the heater element. The heater may be contained substantially within the distal portion of the delivery apparatus to provide thermal insulation to reduce the potential for thermal damage to the surrounding tissues during detachment. In another embodiment, current may pass through the tether which also acts as a heating element.

Many materials may be used to make tether embodiments 72 including polymers, metals and composites thereof. One class of materials that may be useful for tethers includes polymers such as polyolefin, polyolefin elastomer such as polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials that may be used for tether embodiment may include metals such as nickel titanium alloy (Nitinol), gold, platinum, tantalum and steel. Other materials that may be useful for tether construction includes wholly aromatic polyester polymers which are liquid crystal polymers (LCP) that may provide high performance properties and are highly inert. A commercially available LCP polymer is Vectran, which is produced by Kuraray Co. (Tokyo, Japan). The selection of the material may depend on the melting or softening temperature, the power used for detachment, and the body treatment site. The tether may be joined to the implant and/or the pusher by crimping, welding, knot tying, soldering, adhesive bonding, or other means known in the art.

Figure 16:
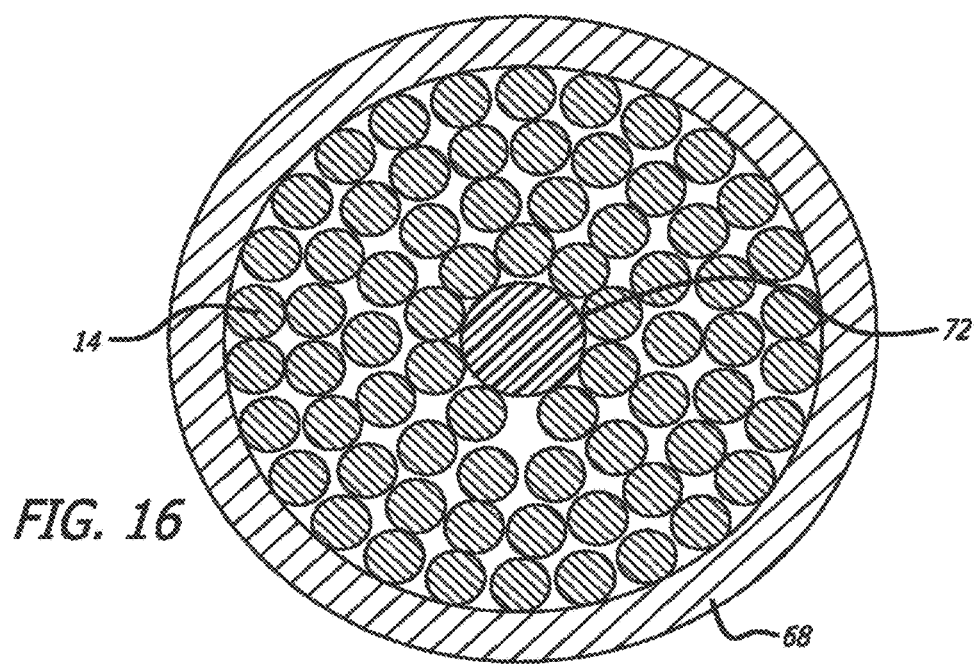
FIG. 16 illustrates an embodiment of a filament configuration for a device for treatment of a patient's vasculature.

It should be noted also that many variations of filament and proximal hub construction such as is detailed above with regard to FIG. 10 may be used for useful embodiments of a device for treatment of a patient's vasculature 10. FIG. 16 shows an enlarged view in transverse cross section of a proximal hub configuration. For the embodiment shown, the filaments 14 are disposed within a proximal hub 68 or end portion of the device 10 with the filaments 14 constrained and tightly packed by an outer ring of the proximal hub 68. A tether member 72 may be disposed within a middle portion of the filaments 14 or within a cavity of the proximal hub 68 proximal of the proximal ends 60 of the filaments 14. Such a tether 72 may be a dissolvable, severable or releasable tether that may be part of a release apparatus as discussed above used to deploy the device.

FIG. 16 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

For some embodiments, the permeable shell 40 or portions thereof may be porous and may be highly permeable to liquids. In contrast to most vascular prosthesis fabrics or grafts which typically have a water permeability below 2,000 ml/min/cm$^2$ when measured at a pressure of 120 mmHg, the permeable shell 40 of some embodiments discussed herein may have a water permeability greater than about 2,000 ml/min/cm$^2$, in some cases greater than about 2,500 ml/min/cm$^2$. For some embodiments, water permeability of the permeable shell 40 or portions thereof may be between about 2,000 and 10,000 ml/min/cm$^2$, more specifically, about 2,000 ml/min/cm$^2$ to about 15,000 ml/min/cm$^2$, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g. polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable_(e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. Potentially suitable bioabsorbable materials include polylactic acid (PLA), poly (alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester, poly (amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

In any of the suitable device embodiments 10 discussed herein, the permeable shell structure 40, or any other suitable permeable shell structure discussed herein, may include one or more fixation elements or surfaces to facilitate fixation of the device within a blood vessel or other vascular site. The fixation elements may comprise hooks, barbs, protrusions, pores, micro-features, texturing, bioadhesives or combinations thereof. Embodiments of the support structure may be fabricated from a tube of metal where portions are removed. The removal of material may be done by laser, electrical discharge machining (EDM), photochemical etching and traditional machining techniques. In any of the described embodiments, the support structure may be constructed with a plurality of wires, cut or etched from a sheet of a material, cut or etched from a tube or a combination thereof as in the art of vascular stent fabrication.

Permeable shell embodiments 40 may be formed at least in part of wire, ribbon, or other filamentary elements 14. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
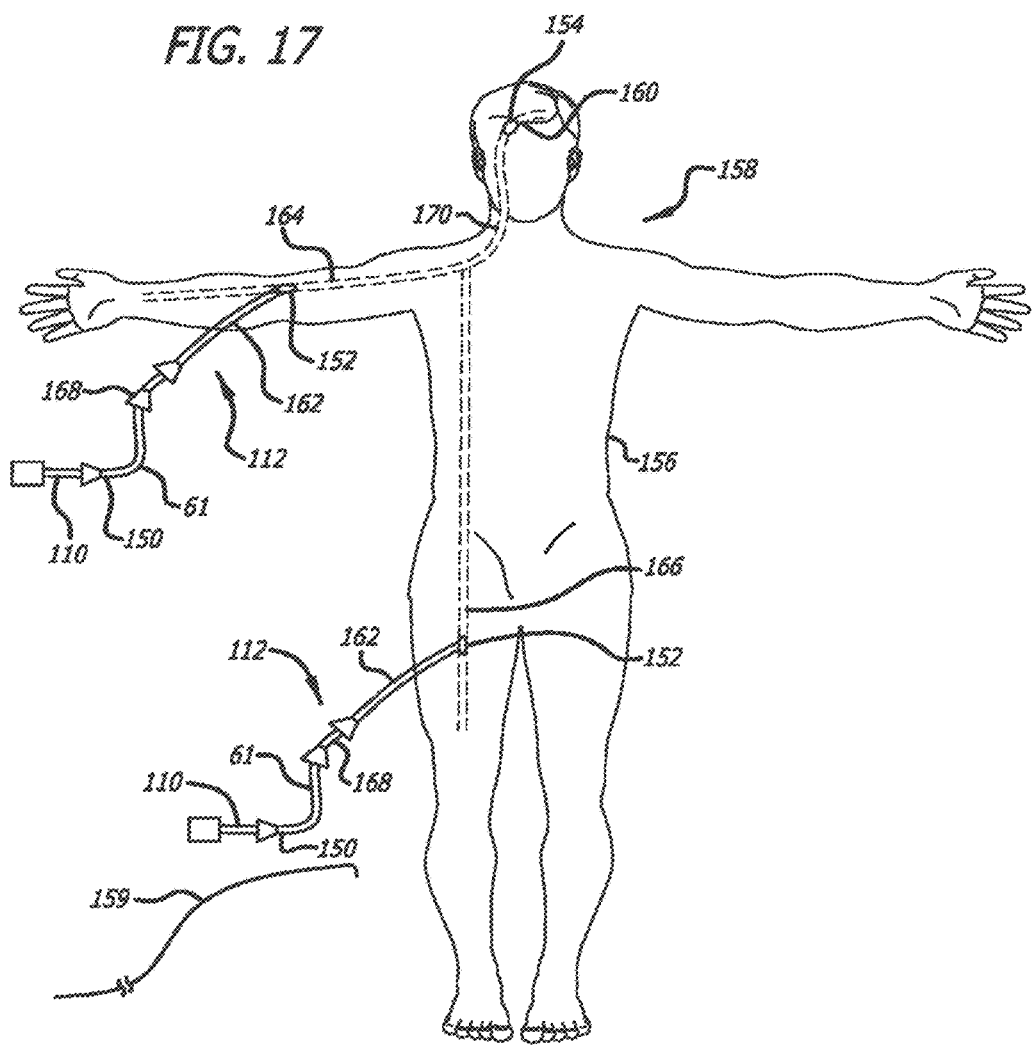
FIG. 17 is a schematic view of a patient being accessed by an introducer sheath, a microcatheter and a device for treatment of a patient's vasculature releasably secured to a distal end of a delivery device or actuator.
Figure 18:
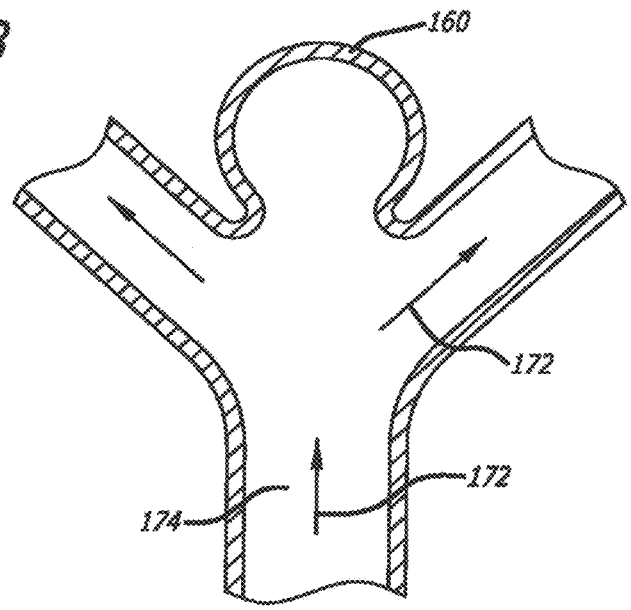
FIG. 18 is a sectional view of a terminal aneurysm.

Device embodiments 10 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10 secured to a delivery apparatus 110 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 110 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 110 is advanced through the microcatheter 61.

Delivery and deployment of device embodiments 10 discussed herein may be carried out by first compressing the device 10, or any other suitable device for treatment of a patient's vasculature discussed herein, to a radially constrained and longitudinally flexible state as shown in FIG. 11. The device 10 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10 secured to a suitable delivery apparatus 110 may then be radially constrained, inserted into a proximal portion of the inner lumen 120 of the microcatheter 61 and distally advanced to the vascular defect 160 through the inner lumen 120.

Once disposed within the vascular defect 160, the device 10 may then allowed to assume an expanded relaxed or partially relaxed state with the permeable shell 40 of the device spanning or partially spanning a portion of the vascular defect 160 or the entire vascular defect 160. The device 10 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
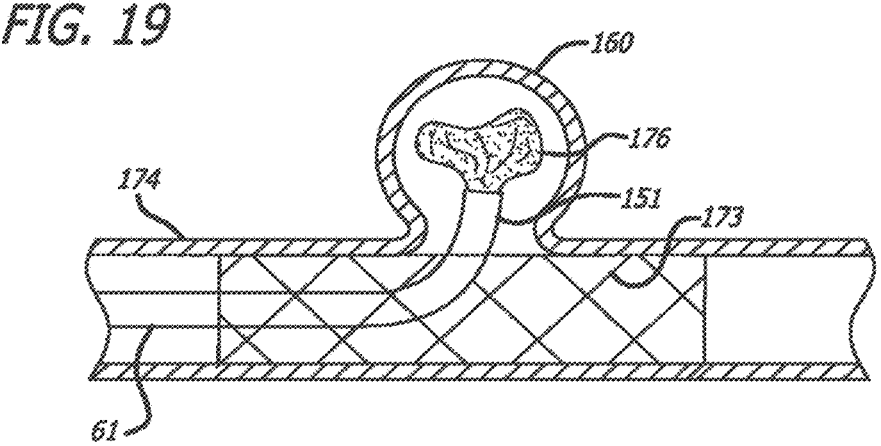
FIG. 19 is a sectional view of an aneurysm.

Some embodiments of devices for the treatment of a patient's vasculature 10 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Figure 28:
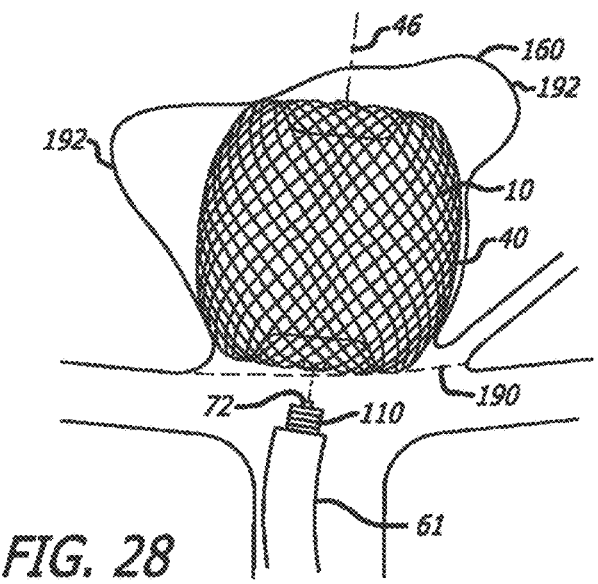
FIG. 28 is an elevation view in partial section of an embodiment of a device for treatment of a patient's vasculature deployed within an irregularly shaped aneurysm.

Prior to delivery and deployment of a device for treatment of a patient's vasculature 10, it may be desirable for the treating physician to choose an appropriately sized device 10 to optimize the treatment results. Some embodiments of treatment may include estimating a volume of a vascular site or defect 160 to be treated and selecting a device 10 with a volume that is substantially the same volume or slightly over-sized relative to the volume of the vascular site or defect 160. The volume of the vascular defect 160 to be occluded may be determined using three-dimensional angiography or other similar imaging techniques along with software which calculates the volume of a selected region. The amount of over-sizing may be between about 2% and 15% of the measured volume. In some embodiments, such as a very irregular shaped aneurysm, it may be desirable to under-size the volume of the device 10. Small lobes or "daughter aneurysms" may be excluded from the volume, defining a truncated volume which may be only partially filled by the device without affecting the outcome. A device 10 deployed within such an irregularly shaped aneurysm 160 is shown in FIG. 28 discussed below. Such a method embodiment may also include implanting or deploying the device 10 so that the vascular defect 160 is substantially filled volumetrically by a combination of device and blood contained therein. The device 10 may be configured to be sufficiently conformal to adapt to irregular shaped vascular defects 160 so that at least about 75%, in some cases about 80%, of the vascular defect volume is occluded by a combination of device 10 and blood contained therein.

Figure 20:
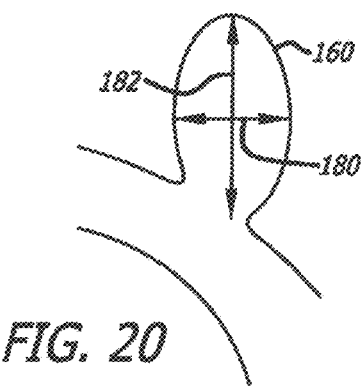
FIG. 20 is a schematic view in section of an aneurysm showing perpendicular arrows which indicate interior nominal longitudinal and transverse dimensions of the aneurysm.
Figure 21:
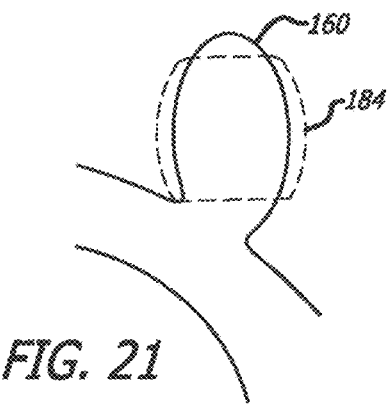
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
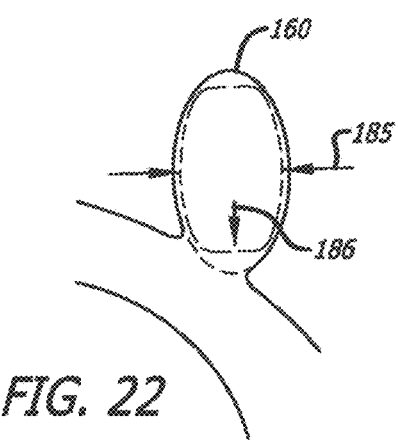
FIG. 22 is a schematic view in section of an outline of a device represented by the dashed line in FIG. 21 in a deployed and partially constrained state within the aneurysm.

In particular, for some treatment embodiments, it may be desirable to choose a device 10 that is properly oversized in a transverse dimension so as to achieve a desired conformance, radial force and fit after deployment of the device 10. FIGS. 20-22 illustrate a schematic representation of how a device 10 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10 may be oversized a small amount (e.g. less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect 10 is shown superimposed over the vascular defect 160 of FIG. 20 illustrating how a device 10 that has been chosen to be approximately 20% oversized in a transverse dimension would look in its unconstrained, relaxed state. FIG. 22 illustrates how the device 10 which is indicated by the dashed line 184 of FIG. 21 might conform to the interior surface of the vascular defect 160 after deployment whereby the nominal transverse dimension of the device 10 in a relaxed unconstrained state has now been slightly constrained by the inward radial force 185 exerted by the vascular defect 160 on the device 10. In response, as the filaments 14 of the device 10 and thus the permeable shell 40 made therefrom have a constant length, the device 10 has assumed a slightly elongated shape in the axial or longitudinal axis of the device 10 so as to elongate and better fill the interior volume of the defect 160 as indicated by the downward arrow 186 in FIG. 22.

Figure 23:
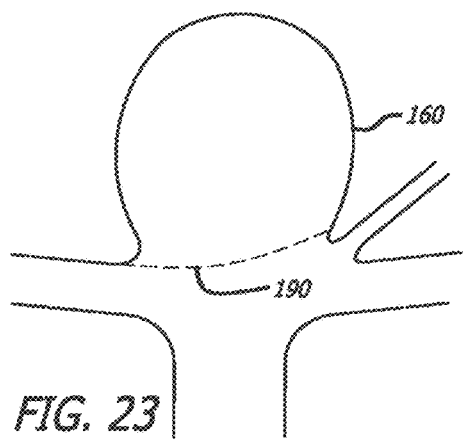
FIGS. 23-26 show a deployment sequence of a device for treatment of a patient's vasculature.
Figure 24:
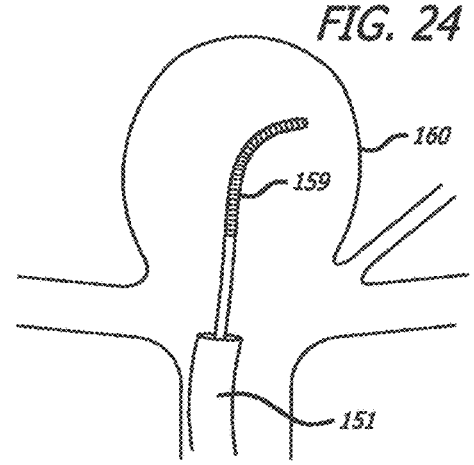

Once a properly sized device 10 has been selected, the delivery and deployment process may then proceed. It should also be noted also that the properties of the device embodiments 10 and delivery system embodiments 112 discussed herein generally allow for retraction of a device 10 after initial deployment into a defect 160, but before detachment of the device 10. Therefore, it may also be possible and desirable to withdraw or retrieve an initially deployed device 10 after the fit within the defect 160 has been evaluated in favor of a differently sized device 10. An example of a terminal aneurysm 160 is shown in FIG. 23 in section. The tip 151 of a catheter, such as a microcatheter 61 may be advanced into or adjacent the vascular site or defect 160 (e.g. aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Figure 25:
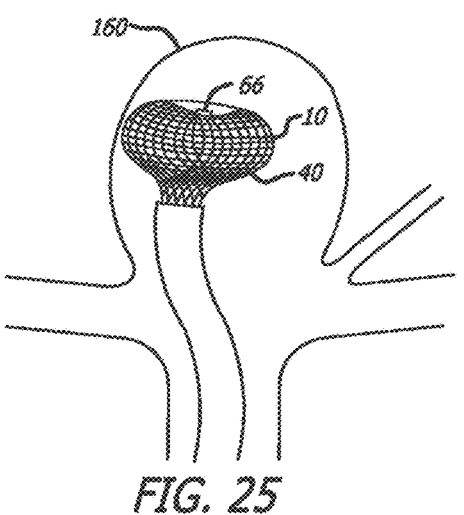

Detachment of the device 10 from the delivery apparatus 110 may be controlled by a control switch 188 disposed at a proximal end of the delivery system 112, which may also be coupled to an energy source 142, which severs the tether 72 that secures the proximal hub 68 of the device 10 to the delivery apparatus 110. While disposed within the microcatheter 61 or other suitable delivery system 112, as shown in FIG. 11, the filaments 14 of the permeable shell 40 may take on an elongated, non-everted configuration substantially parallel to each other and a longitudinal axis of the catheter 61. Once the device 10 is pushed out of the distal port of the microcatheter 61, or the radial constraint is otherwise removed, the distal ends 62 of the filaments 14 may then axially contract towards each other so as to assume the globular everted configuration within the vascular defect 160 as shown in FIG. 25.

The device 10 may be inserted through the microcatheter 61 such that the catheter lumen 120 restrains radial expansion of the device 10 during delivery. Once the distal tip or deployment port of the delivery system 112 is positioned in a desirable location adjacent or within a vascular defect 160, the device 10 may be deployed out the distal end of the catheter 61 thus allowing the device to begin to radially expand as shown in FIG. 25. As the device 10 emerges from the distal end of the delivery system 112, the device 10 expands to an expanded state within the vascular defect 160, but may be at least partially constrained by an interior surface of the vascular defect 160.

Figure 26:
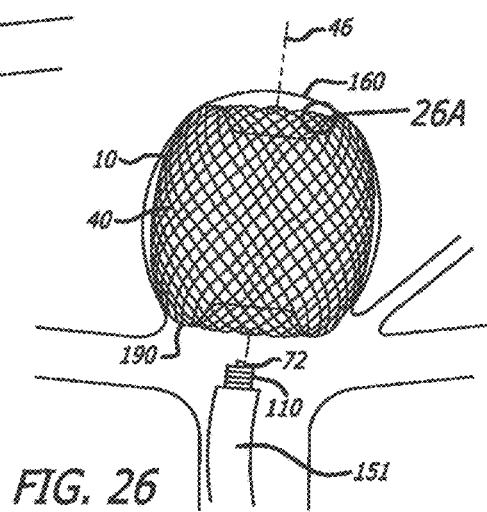

Upon full deployment, radial expansion of the device 10 may serve to secure the device 10 within the vascular defect 160 and also deploy the permeable shell 40 across at least a portion of an opening 190 (e.g. aneurysm neck) so as to at least partially isolate the vascular defect 160 from flow, pressure or both of the patient's vasculature adjacent the vascular defect 160 as shown in FIG. 26. The conformability of the device 10, particularly in the neck region 190 may provide for improved sealing. For some embodiments, once deployed, the permeable shell 40 may substantially slow flow of fluids and impede flow into the vascular site and thus reduce pressure within the vascular defect 160. For some embodiments, the device 10 may be implanted substantially within the vascular defect 160, however, in some embodiments, a portion of the device 10 may extend into the defect opening or neck 190 or into branch vessels.

Figure 26A:
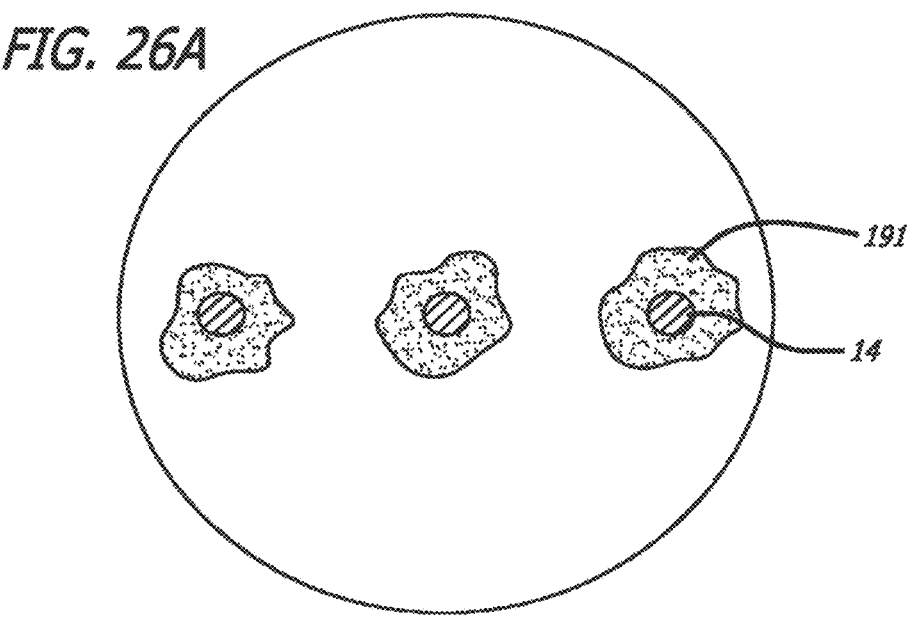
FIG. 26A is an enlarged view of the device of FIG. 26 in section indicated by the encircled portion 26A in FIG. 26 and showing thrombus formation on filaments of the device.
Figure 26B:
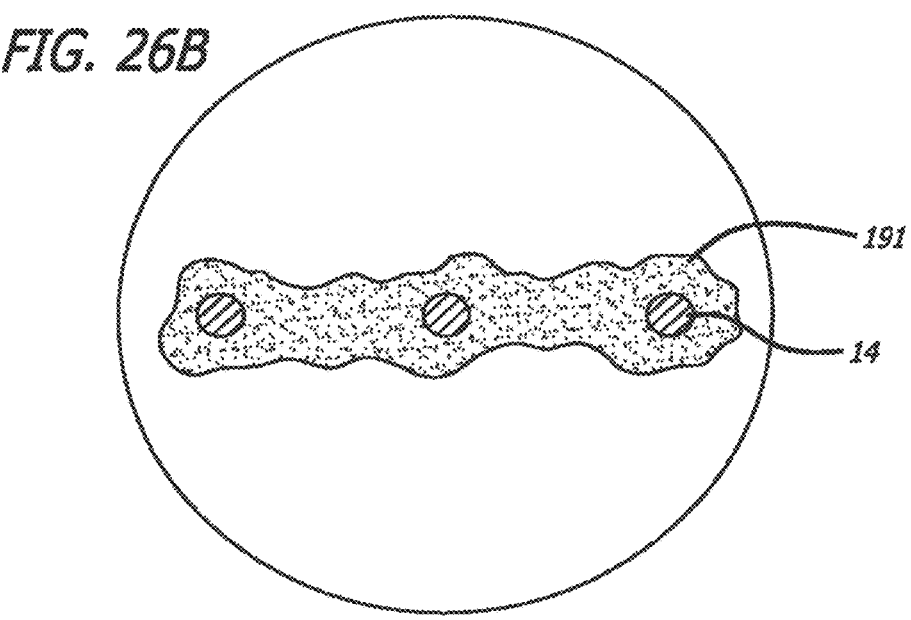
FIG. 26B illustrates further thrombus formation on the filaments of FIG. 26A.

Once the device 10 has been deployed in the vascular defect, the isolation of the defect, slowing of flow, reduce pressure or any combination of these effects may case thrombus formation within an interior volume of the device 10, outside the device 10 or on the device itself or some component thereof. FIG. 26A illustrates thrombus formation on filaments of the permeable shell 40 of the device 10 in section. As thrombus 191 forms on the filaments 14, portions of the thrombus material 191 are disposed within an interior volume of the permeable shell, external to an outer surface of the permeable shell and between adjacent filaments of the permeable shell. As the thrombus material 191 continues to form on the filaments 14, the size of the pores 64 between the filaments 14 will begin to decrease, further slowing a flow of blood therethrough. Thrombus 191 may also form within the interior volume of the permeable shell in free space not in contact with the actual structure of the permeable shell. As thrombus formation continues on the filaments 14 over time after deployment of the device 10, the pores 64 between the filaments will eventually be closed off, as shown in FIG. 26B. The effects of such a process are also shown in FIGS. 59A-59D which are discussed below. The thrombus or clot formation process illustrated in FIGS. 26A and 26B may occur in a similar manner on any of the device embodiments or portions thereof discussed herein. In particular, such thrombus formation 191 may occur on the filaments 14 of the shell, inner structures or any other suitable portion of device embodiments 251, 266, 280, 298, 310, 336, 360, 370, 376 or 390.

One exemplary case study that has been conducted includes a procedure performed on a female canine where an aneurysm was surgically created in the subject canine. The target aneurysm prior to treatment had a maximum transverse dimension of about 8 mm, a length of about 10 mm and a neck measurement of about 5.6 mm. The device 10 deployed included a permeable shell 40 formed of 144 resilient filaments having a transverse diameter of about 0.0015 inches braided into a globular structure having a transverse dimension of about 10 mm and a longitudinal length of about 7 mm in a relaxed expanded state. The maximum size 100 of the pores 64 of the expanded deployed permeable shell 40 was about 0.013 inches. The device was delivered to the target aneurysm using a 5 Fr. Guider Softip XF guide catheter made by Boston Scientific. The maximum size 100 of the pores 64 of the portion of the expanded deployed permeable shell 40 that spanned the neck of the aneurysm again was about 0.013 inches. Five minutes after detachment from the delivery system, the device 10 had produced acute occlusion of the aneurysm.

Another exemplary case study conducted involved treatment of a surgically created aneurysm in a New Zealand White Rabbit. The target aneurysm prior to treatment had a maximum transverse dimension of about 3.6 mm, length of about 5.8 mm and a neck measurement of about 3.4 mm. The device 10 deployed included a permeable shell formed of 144 resilient filaments having a transverse diameter of about 0.001 inches braided into a globular structure having a transverse dimension of about 4 mm and a length of about 5 mm in a relaxed expanded state. The pore size 100 of the portion of the braided mesh of the expanded deployed permeable shell 40 that was configured to span the neck of the vascular defect was about 0.005 inches. The device was delivered to the surgically created aneurysm with a 5 Fr. Envoy STR guide catheter manufactured by Cordis Neurovascular. A Renegade Hi-Flo microcatheter manufactured by Boston Scientific having an inner lumen diameter of about 0.027 inches was then inserted through the guide catheter and served as a conduit for delivery of the device 10 secured to a distal end of a delivery apparatus. Once the device 10 was deployed within the vascular defect 160, the vascular defect 160 achieved at least partial occlusion at 5 minutes from implantation. However, due to the sensitivity of the subject animal to angiographic injection and measurement, no further data was taken during the procedure. Complete occlusion was observed for the device when examined at 3 weeks from the procedure.

For some embodiments, as discussed above, the device 10 may be manipulated by the user to position the device 10 within the vascular site or defect 160 during or after deployment but prior to detachment. For some embodiments, the device 10 may be rotated in order to achieve a desired position of the device 10 and, more specifically, a desired position of the permeable shell 40, prior to or during deployment of the device 10. For some embodiments, the device 10 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10 from the delivery apparatus 110 of the delivery system 112. These delivery and deployment methods may be used for deployment within berry aneurysms, terminal aneurysms, or any other suitable vascular defect embodiments 160. Some method embodiments include deploying the device 10 at a confluence of three vessels of the patient's vasculature that form a bifurcation such that the permeable shell 40 of the device 10 substantially covers the neck of a terminal aneurysm. Once the physician is satisfied with the deployment, size and position of the device 10, the device 10 may then be detached by actuation of the control switch 188 by the methods described above and shown in FIG. 26. Thereafter, the device 10 is in an implanted state within the vascular defect 160 to effect treatment thereof.

Figure 27:
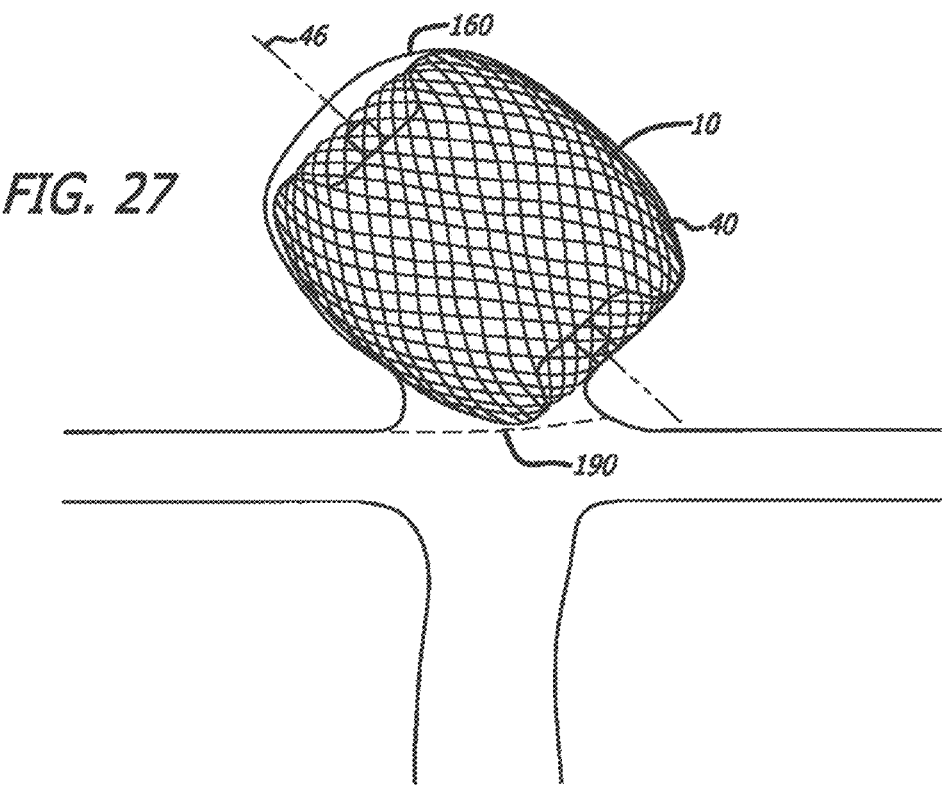
FIG. 27 is an elevation view in partial section of an embodiment of a device for treatment of a patient's vasculature deployed within an aneurysm at a tilted angle.

FIG. 27 illustrates another configuration of a deployed and implanted device in a patient's vascular defect 160. While the implantation configuration shown in FIG. 26 indicates a configuration whereby the longitudinal axis 46 of the device 10 is substantially aligned with a longitudinal axis of the defect 160, other suitable and clinically effective implantation embodiments may be used. For example, FIG. 27 shows an implantation embodiment whereby the longitudinal axis 46 of the implanted device 10 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10 implanted in an irregularly shaped vascular defect 160. The aneurysm 160 shown has at least two distinct lobes 192 extending from the main aneurysm cavity. The two lobes 192 shown are unfilled by the deployed vascular device 10, yet the lobes 192 are still isolated from the parent vessel of the patient's body due to the occlusion of the aneurysm neck portion 190.

Markers, such as radiopaque markers, on the device 10 or delivery system 112 may be used in conjunction with external imaging equipment (e.g. x-ray) to facilitate positioning of the device or delivery system during deployment. Once the device is properly positioned, the device 10 may be detached by the user. For some embodiments, the detachment of the device 10 from the delivery apparatus 110 of the delivery system 112 may be affected by the delivery of energy (e.g. heat, radiofrequency, ultrasound, vibrational, or laser) to a junction or release mechanism between the device 10 and the delivery apparatus 110. Once the device 10 has been detached, the delivery system 112 may be withdrawn from the patient's vasculature or patient's body 158. For some embodiments, a stent 173 may be place within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10. The agent release may be affected by one or more of the body's environmental parameters or energy may be delivered (from an internal or external source) to the device 10. Hemostasis may occur within the vascular defect 160 as a result of the isolation of the vascular defect 160, ultimately leading to clotting and substantial occlusion of the vascular defect 160 by a combination of thrombotic material and the device 10. For some embodiments, thrombosis within the vascular defect 160 may be facilitated by agents released from the device 10 and/or drugs or other therapeutic agents delivered to the patient.

For some embodiments, once the device 10 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10 for some embodiments, including an outer surface of the filaments 14 or the hubs 66 and 68. Such a coating or coatings may be applied to any suitable portion of the permeable shell 40. Energy forms may also be applied through the delivery apparatus 110 and/or a separate catheter to facilitate fixation and/or healing of the device 10 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10.

In any of the above embodiments, the device 10 may have sufficient radial compliance so as to be readily retrievable or retractable into a typical microcatheter 61. The proximal portion of the device 10, or the device as a whole for some embodiments, may be engineered or modified by the use of reduced diameter filaments, tapered filaments, or filaments oriented for radial flexure so that the device 10 is retractable into a tube that has an internal diameter that is less than about 0.7 mm, using a retraction force less than about 2.7 Newtons (0.6 lbf) force. The force for retrieving the device 10 into a microcatheter 61 may be between about 0.8 Newtons (0.18 lbf) and about 2.25 Newtons (0.5 lbf).

Figure 29:
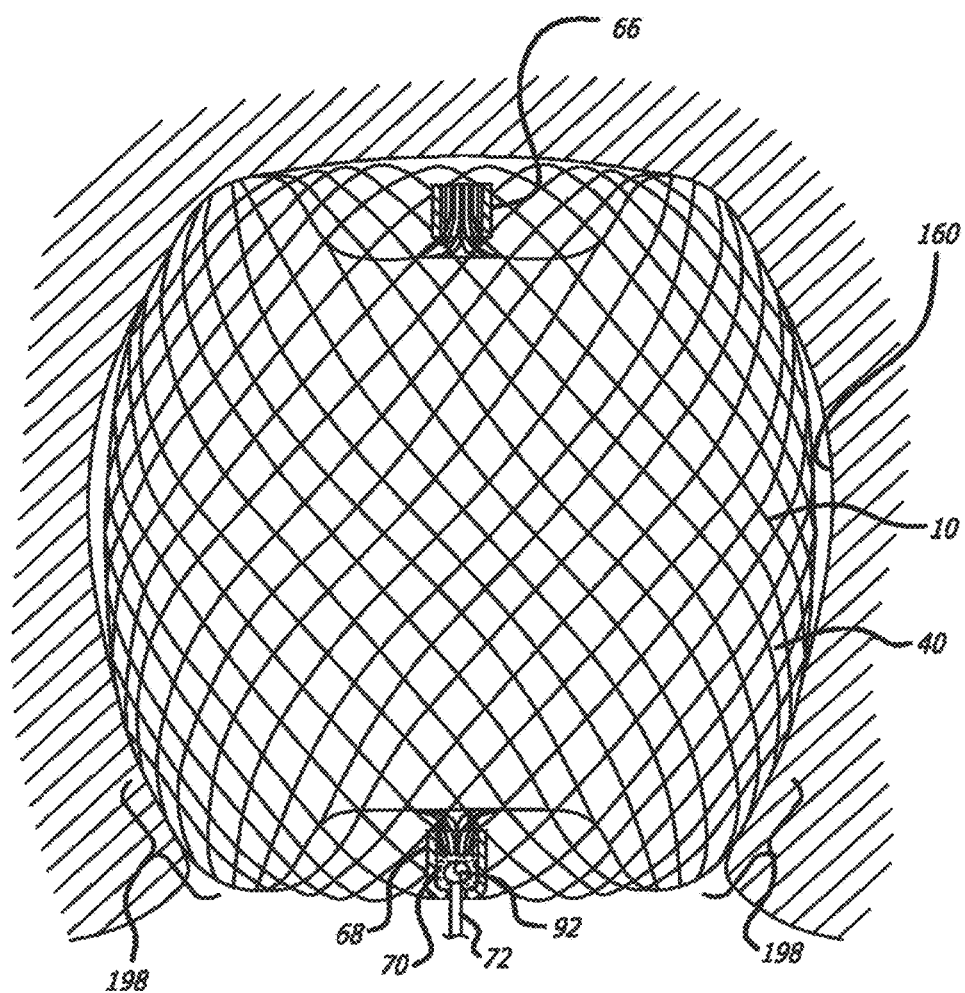
FIG. 29 shows an elevation view in section of a device for treatment of a patient's vasculature deployed within a vascular defect aneurysm.

Engagement of the permeable shell 40 with tissue of an inner surface of a vascular defect 160, when in an expanded relaxed state, may be achieved by the exertion of an outward radial force against tissue of the inside surface of the cavity of the patient's vascular defect 160 as shown in FIG. 29. A similar outward radial force may also be applied by a proximal end portion and permeable shell 40 of the device 10 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40 of the device 10 may be such that it will readily ovalize to adapt to the shape and size of an aneurysm neck 190, as shown in FIGS. 20-22, thus providing a good seal and barrier to flow around the device. Thus the device 10 may achieve a good seal, substantially preventing flow around the device without the need for fixation members that protrude into the parent vessel.

Figure 30:
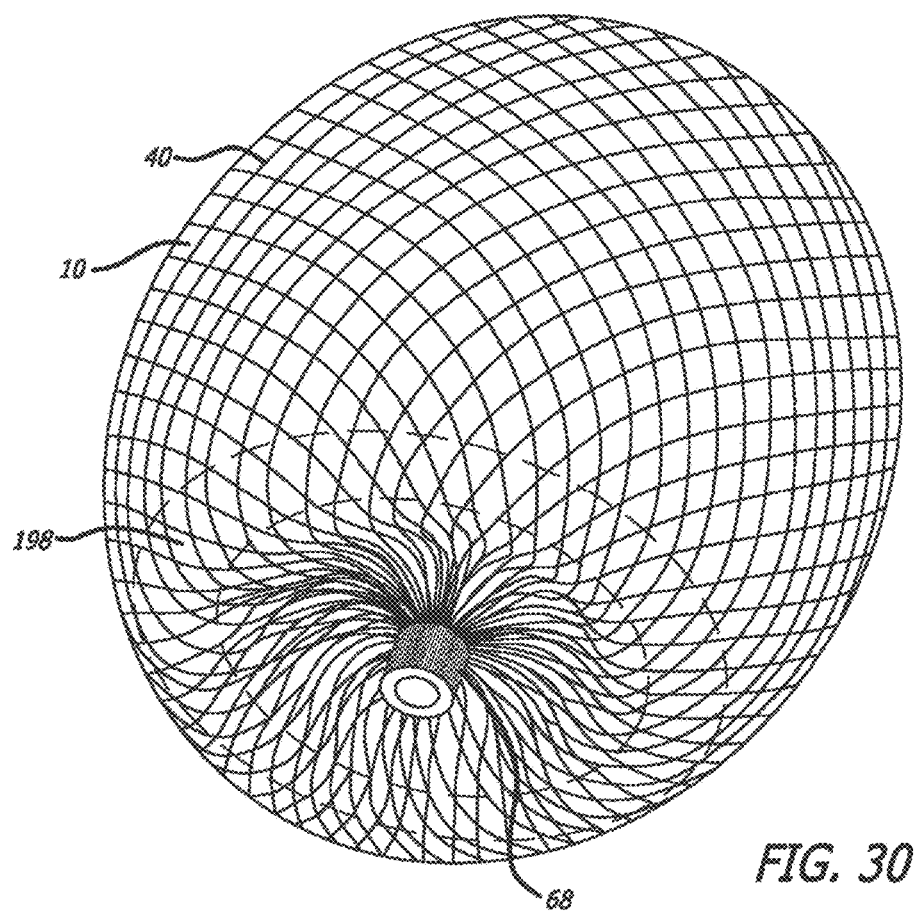
FIG. 30 shows a proximal perspective view of an embodiment of a device for treatment of a patient's vasculature with a sealing zone embodiment indicated by a set of dashed lines.

Some implanted device embodiments 10 have the ends of the filaments 14 of the permeable shell 40 disposed even with or just within a plane formed by the apices of the filaments disposed adjacent to the ends. Some embodiments of the device 10 may also include a sealing member disposed within or about a perimeter zone 198 or other suitable portion of the permeable shell 40 and be configured to facilitate the disruption of flow, a fibrotic tissue response, or physically form a seal between the permeable shell 40 and a surface of the patient's vasculature. The sealing member may comprise coatings, fibers or surface treatments as described herein. The sealing member may be in a part or all of an area of the periphery of the device adjacent where the device contacts the wall of the aneurysm near the aneurysm neck (sealing zone 198) as shown in FIGS. 29 and 30. The zone may extend from about the apex of the outer proximal end radius 88 for a distance up to about 20% of the height of the expanded device 10. The sealing zone 198 may include between about 5% and 30% of the device 10 surface area. Since the flow of blood into an aneurysm 160 generally favors one side of the opening, the sealing member may be incorporated in or attached to the permeable shell 40 structure throughout the peripheral area (sealing zone 198) shown in FIG. 30. Some embodiments of the sealing member may include a swellable polymer. In some embodiments, the sealing member may include or bioactive material or agent such as a biologic material or biodegradable, bioresorbable or other bioactive polymer or copolymers thereof Any embodiment of devices for treatment of a patient's vasculature 10, delivery system 112 for such devices 10 or both discussed herein may be adapted to deliver energy to the device for treatment of a patient's vasculature or to tissue surrounding the device 10 at the implant site for the purpose of facilitating fixation of a device 10, healing of tissue adjacent the device or both. In some embodiments, energy may be delivered through a delivery system 112 to the device 10 for treatment of a patient's vasculature such that the device 10 is heated. In some embodiments, energy may be delivered via a separate elongate instrument (e.g. catheter, not shown) to the device 10 for treatment of a patient's vasculature and/or surrounding tissue at the site of the implant 154. Examples of energy embodiments that may be delivered include but are not limited to light energy, thermal or vibration energy, electromagnetic energy, radio frequency energy and ultrasonic energy. For some embodiments, energy delivered to the device 10 may trigger the release of chemical or biologic agents to promote fixation of a device for treatment of a patient's vasculature 10 to a patient's tissue, healing of tissue disposed adjacent such a device 10 or both.

The permeable shell 40 of some device embodiments 10 may also be configured to react to the delivery of energy to effect a change in the mechanical or structural characteristics, deliver drugs or other bioactive agents or transfer heat to the surrounding tissue. For example, some device embodiments 10 may be made softer or more rigid from the use of materials that change properties when exposed to electromagnetic energy (e.g. heat, light, or radio frequency energy). In some cases, the permeable shell 40 may include a polymer that reacts in response to physiologic fluids by expanding. An exemplary material is described by Cox in U.S. patent application Ser. No. 2004/0186562, filed Jan. 22, 2004, titled "Aneurysm Treatment Device and Method of Use", which is incorporated by reference herein in its entirety.

Figure 31:
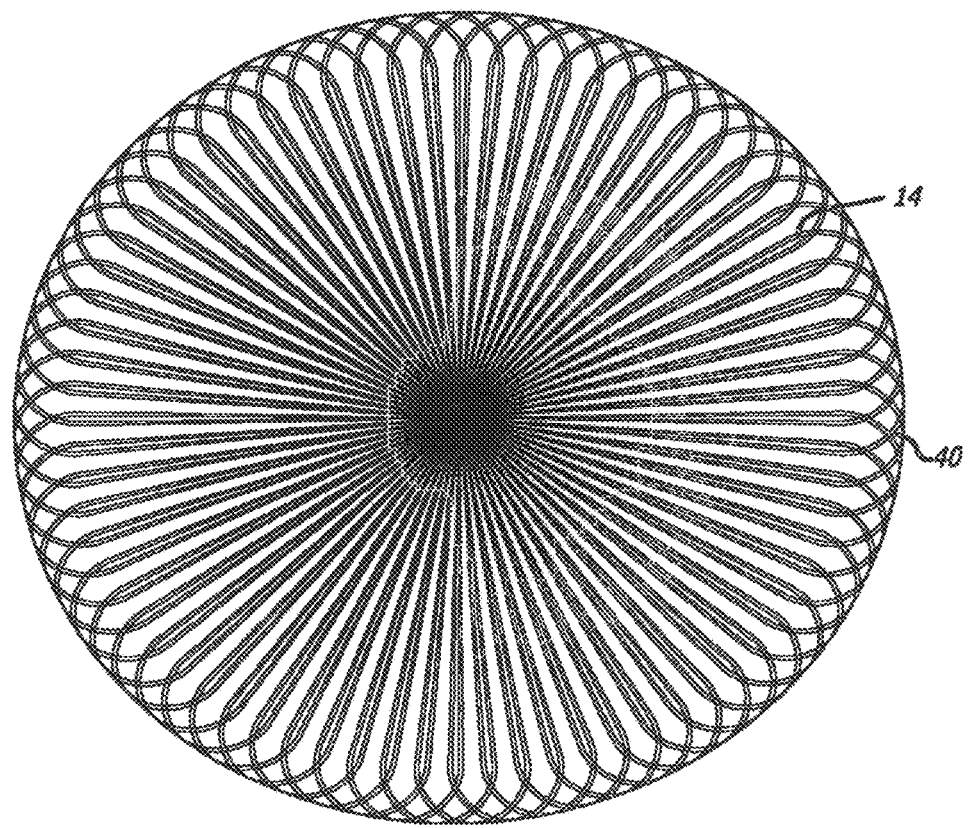
FIGS. 31-35 illustrate various different embodiments of braiding patterns that may be used for permeable shells of devices for treatment of a patient's vasculature.
Figure 32:
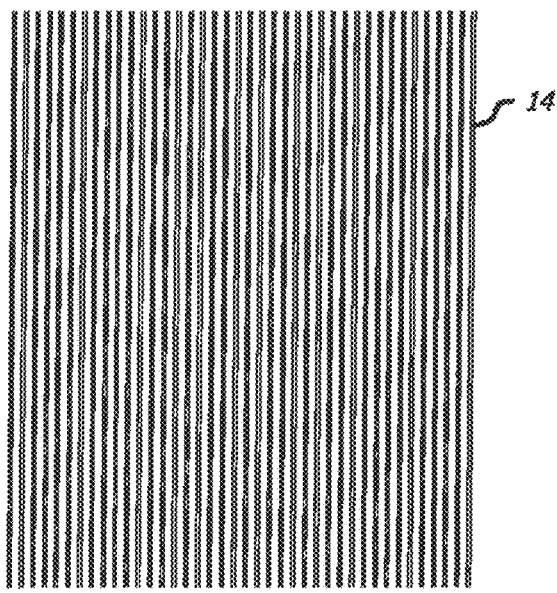
Figure 33:
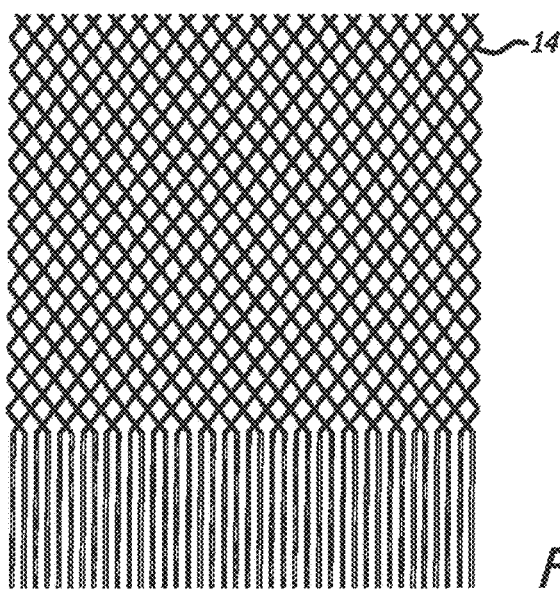
Figure 34:
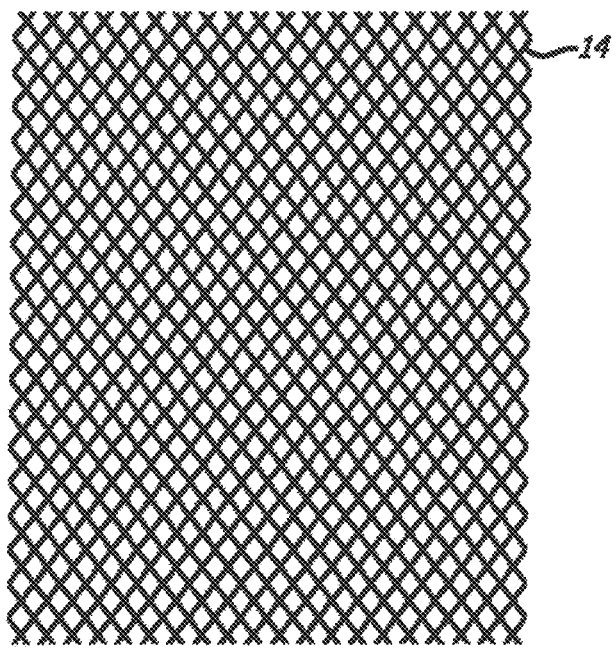

Device embodiments 10 and components thereof discussed herein may take on a large variety of configurations to achieve specific or generally desirable clinical results. In some device embodiments 10, the start of the braided structure of the permeable shell 40 may be delayed from the proximal hub 68 so that the filaments 1 emanate from the proximal hub 68 in a spoke-like radial fashion as shown in the proximal end view of a device in FIG. 31. A flattened analog version of the braid pattern of FIG. 31 is also shown in FIG. 33. This configuration may result in a smaller width gap between the filaments 14 at a given radial distance from the proximal hub 68 relative to a fully braided configuration, the flattened analog pattern of which is shown in FIG. 34. This may provide better flow disruption and promote hemostasis in the area of the device 10 that may be subjected to the highest flow rates. FIG. 32 illustrates a flattened analog representation of a non-braided filament structure for reference.

Figure 35:
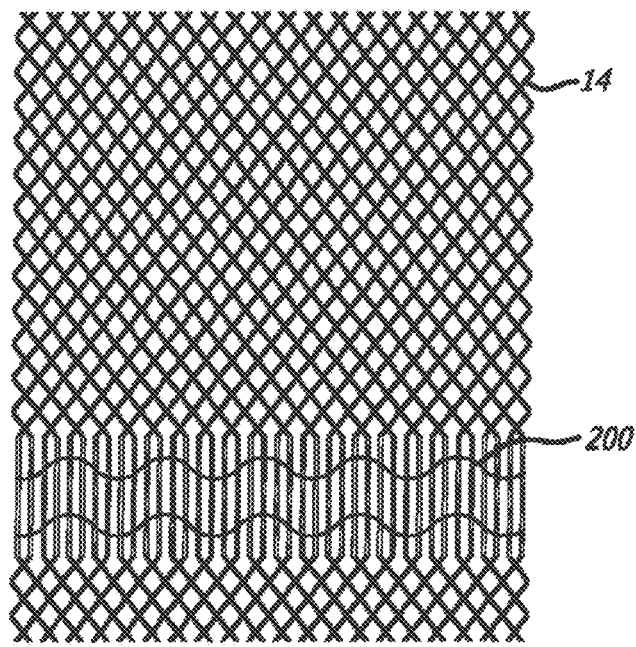

The woven structure may include a portion where the weave or braid of the filaments 14 is interrupted as shown in a flat pattern analog pattern in FIG. 35. In the interrupted region, the filaments 14 may be substantially parallel to each other. The interrupted area may provide a region with different mechanical characteristics such as radial stiffness and/or compliance. Further, the interrupted region may allow for the addition of non-structural fibers or sealing members 200 as described herein or other elements to facilitate fixation, healing, fibrosis or thrombosis. The interrupted region may be within, part of or adjacent to the sealing member zone 198 as shown in FIGS. 29 and 30. The interrupted region may be less than about 50% of the surface area and may be between about 5% and 25% of the surface area.

Figure 36:
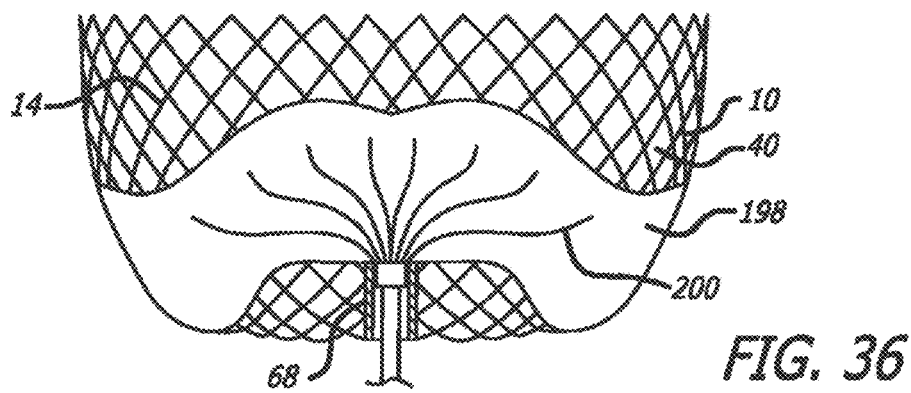
FIG. 36 illustrates a device for treatment of a patient's vasculature that includes non-structural fibers in the permeable shell structure of the device.
Figure 37:
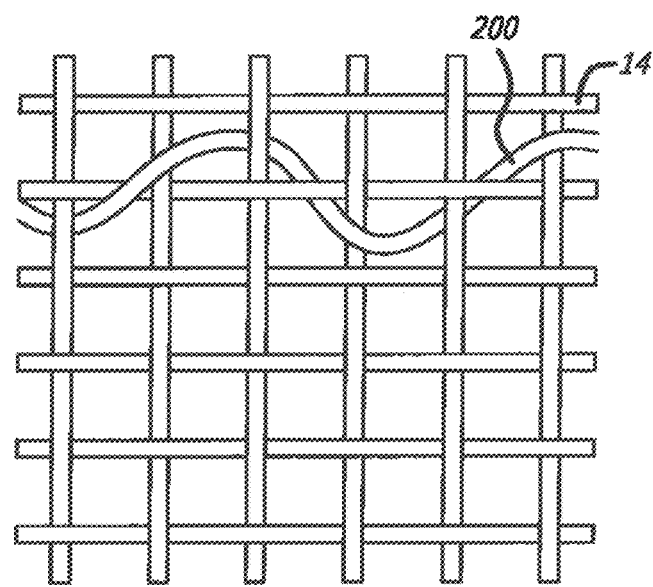
FIG. 37 is an enlarged view of non-structural fibers woven into filaments of a permeable shell structure.

In some embodiments, filamentary or fibrous members that may be substantially non-structural may be attached or interwoven into the structural filaments of a portion of the permeable shell to increase a resistance to the flow of blood through the permeable shell structure 40 or enhance the formation of thrombus and/or healing of the tissue around the device. In some embodiments, a plurality of fibers 200 may be attached on the inner surface of the permeable shell 40 near the proximal hub 68 as shown in FIG. 36. The fibrous members 200 may be the fibers that form the detachment system tether for some embodiments. In some embodiments, one or more fibers 200 may be interwoven into the permeable shell filaments 14 as shown in FIG. 37. The non-structural fibers 200, which may be microfibers or any other suitable fibers, may be polymeric. The non-structural fibers 200 may include, but not limited to, any of the fibers or microfibers discussed or incorporated herein.

In some cases, device embodiments for treatment of a patient's vasculature 10 may generally be fabricated by braiding a substantially tubular braided structure with filamentary elements 14, forming the braided tubular structure into a desired shape, and heat setting the braided formed filaments into the desired shape. Once so formed, the ends of the elongate resilient filaments 14 may then be secured together relative to each other by any of the methods discussed above and proximal and distal hubs 66 and 68 added.

Figure 38:
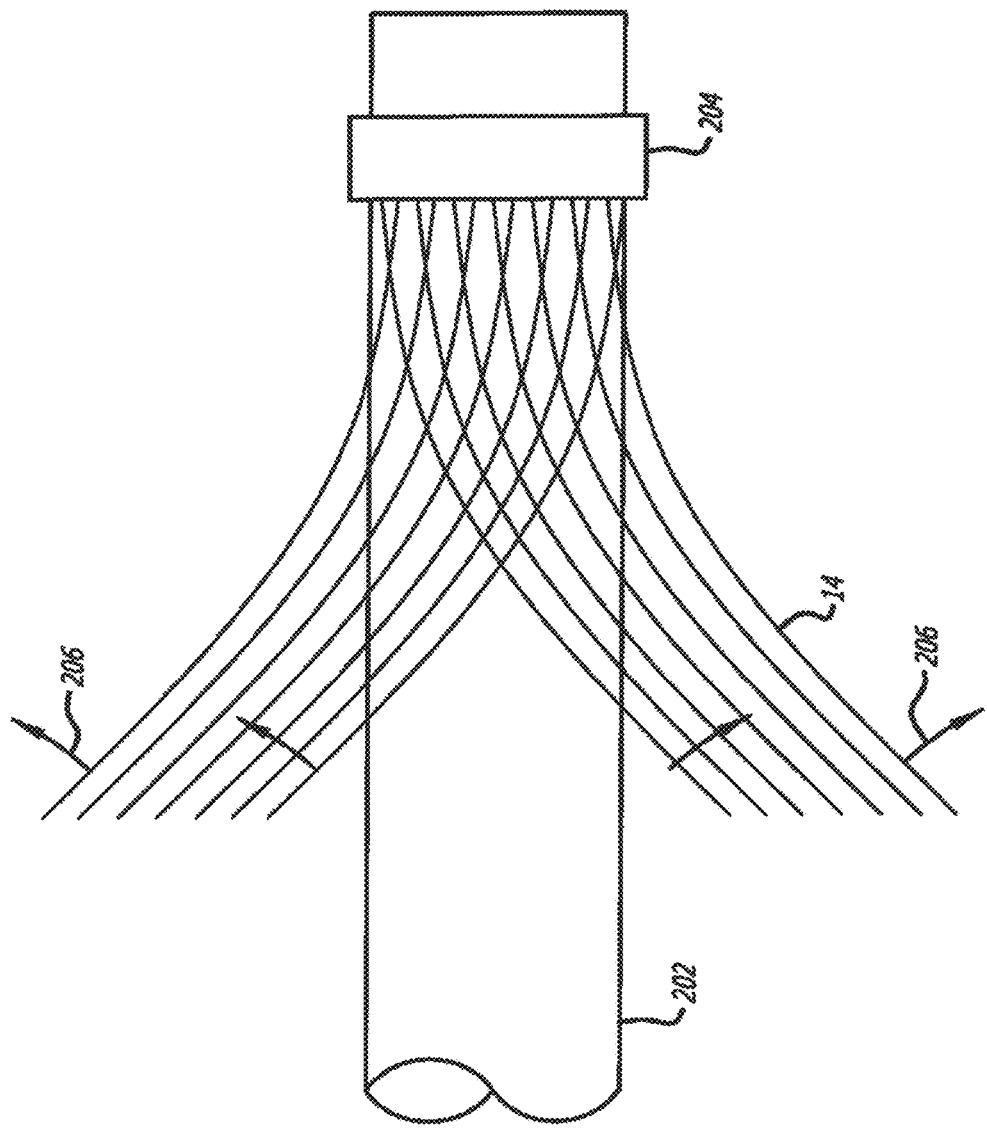
FIG. 38 is an elevation view of a mandrel used for manufacture of a braided tubular member for construction of an embodiment of a device for treatment of a patient's vasculature with the initiation of the braiding process shown.
Figure 39:
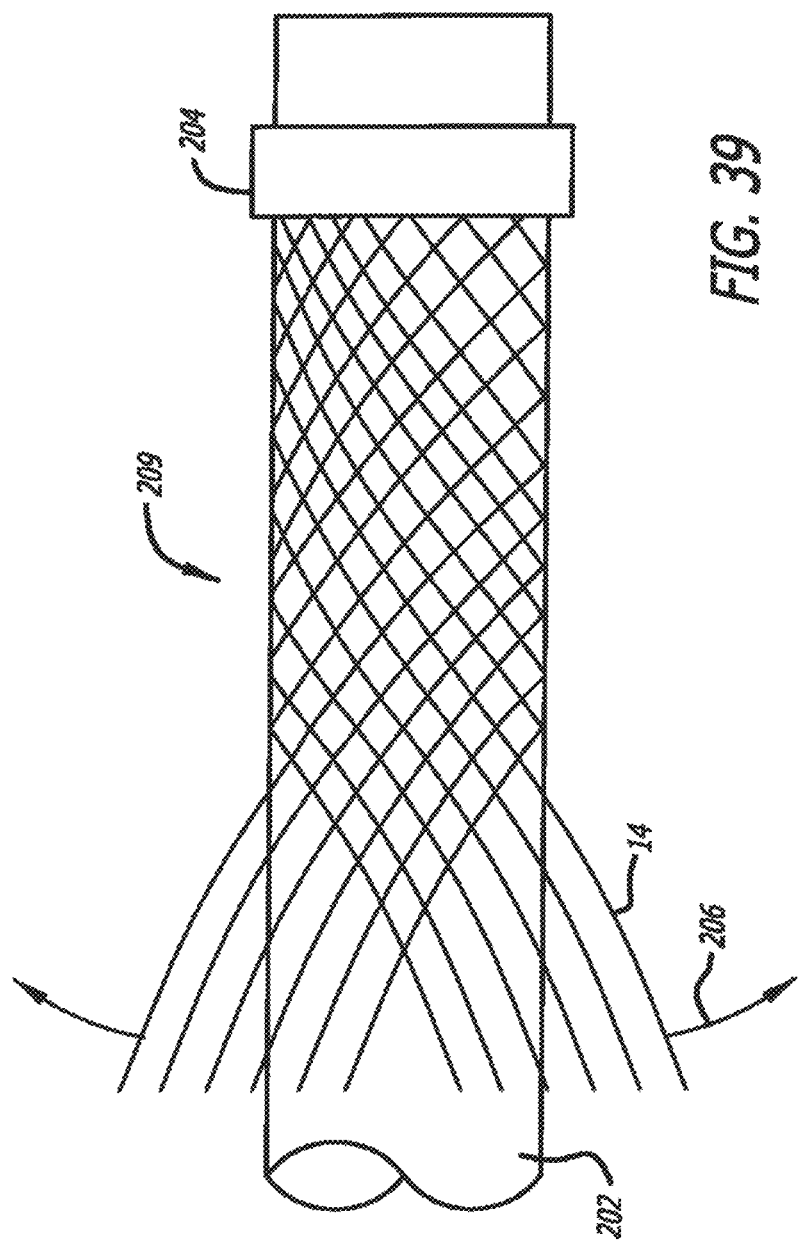
FIG. 39 is an elevation view of a braiding process for a braided tubular member used for manufacture of a device.

Such a braiding process may be carried out by automated machine fabrication or may also be performed by hand. An embodiment of a process for braiding a tubular braided structure by a manual process is shown in FIG. 38. A plurality of elongate resilient filaments 14 are secured at one end of an elongate cylindrical braiding mandrel 202 by a constraining band 204. The band 204 may include any suitable structure that secured the ends of the filaments 14 relative to the mandrel 202 such as a band of adhesive tape, an elastic band, an annular clamp or the like. The loose ends of the filaments 14 opposite the secured ends are being manipulated in a braided or woven pattern as indicated by the arrows 206 to achieve a one over-one under braid pattern for generation of a braided tubular member 208. As discussed above, although a one over-one under simple braid pattern is shown and discussed, other braid or weave patterns may also be used. One such example of another braid configuration may include a two over-one under pattern. FIG. 39 illustrates the braided tubular member 208 taking shape and lengthening as the braiding process continues as indicated by the arrows 206 in FIG. 39. Once the braided tubular member 208 achieves sufficient length, it may be removed from the braiding mandrel 202 and positioned within a shaping fixture such as the shaping fixture embodiments shown in FIGS. 40 and 41.

Figure 40:
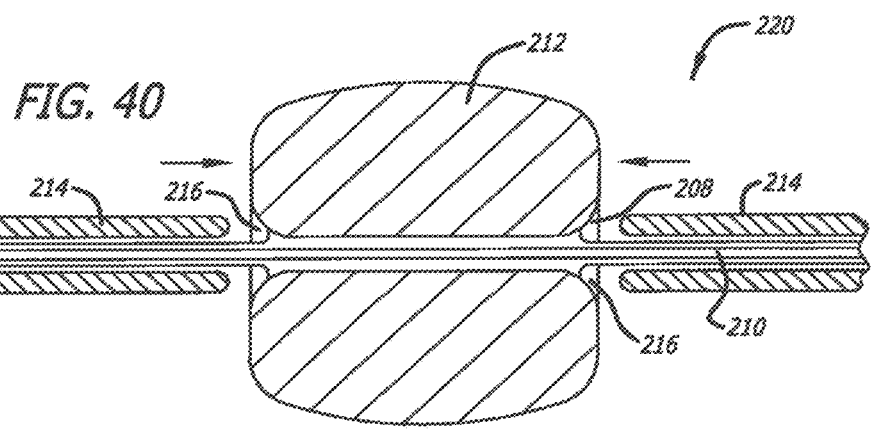
FIG. 40 is an elevation view in partial section of an embodiment of a fixture for heat setting a braided tubular member for manufacture of a device for treatment of a patient's vasculature.

FIG. 40 shows the tubular braided member 208 disposed over an internal rod mandrel 210 that extends through central lumens of an internal ball mandrel 212 and a pair of opposed recessed end forming mandrels 214. The tubular braided member 208 is also disposed over an outer surface of the internal ball mandrel 212 and within an inner lumen of each of the end forming mandrels 214. In order to hold the braided tubular member 208 onto an outer surface contour of the internal ball mandrel 212, including the recessed ends 216 thereof, the end forming mandrels 214 are configured to be pushed against and into the recessed ends 216 of the internal ball mandrel 212 such that the inside surface of the braided tubular member 208 is held against the outer contour of the internal ball mandrel 212 and fixed in place. This entire fixture 220 with the inside surface of the braided tubular structure 208 held against the outside surface of the internal ball mandrel 212 may then be subjected to an appropriate heat treatment such that the resilient filaments 14 of the braided tubular member 208 assume or are otherwise shape-set to the outer contour of the central ball mandrel 212. In some embodiments, the filamentary elements 14 of the permeable shell 40 may be held by a fixture configured to hold the permeable shell 40 in a desired shape and heated to about 475-525 degrees C. for about 5-10 minutes to shape-set the structure.

The central ball mandrel 212 may be configured to have any desired shape so as to produce a shape set tubular braided member 208 that forms a permeable shell 40 having a desired shape and size such as the globular configuration of the device 10 of FIG. 3-6 above, or any other suitable configuration. As such, the central ball mandrel 212 may also be a globular-shaped ball with recesses in opposing sides for the hubs 66 and 68 that is placed inside the tubular braid 208. A mold or molds that have one or more pieces that are assembled to form a cavity with the desired device shape may also be used in conjunction with or in place of the end forming mandrels 214. Once the heat set process in complete, fibers, coatings, surface treatments may be added to certain filaments, portions of filaments, or all of the permeable shell 40 structure that results. Further, for some embodiments of device processing, the permeable shell 40 may be formed as discussed above by securing proximal ends 60 and distal ends 62 of elongate filamentary elements 14, or to respective proximal and distal hubs 66 and 68.

Figure 41:
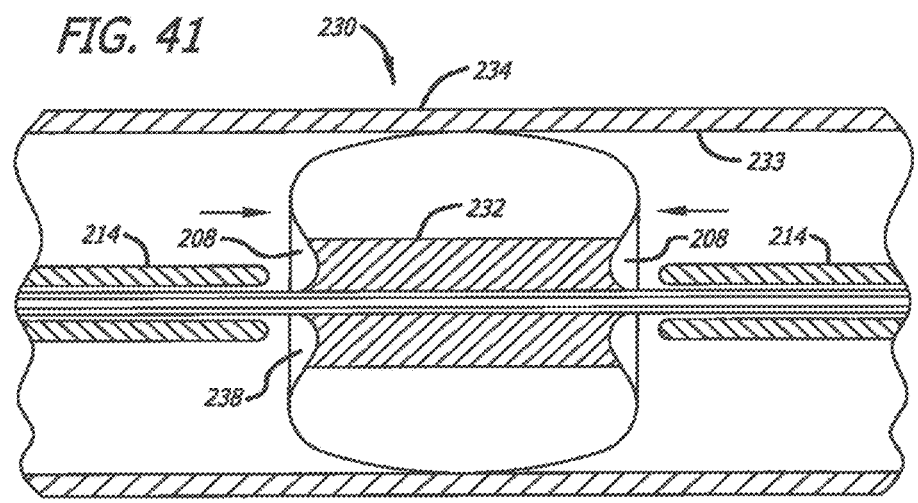
FIG. 41 is an elevation view in partial section of an embodiment of a fixture for heat setting a braided tubular member for manufacture of a device for treatment of a patient's vasculature.
Figure 42:
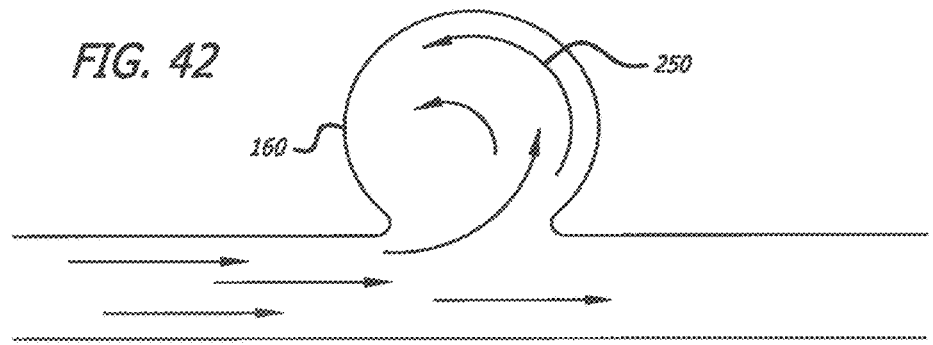
FIG. 42 is an elevation view in section that illustrates a flow of blood within an aneurysm of a patient's vasculature.
Figure 43A:
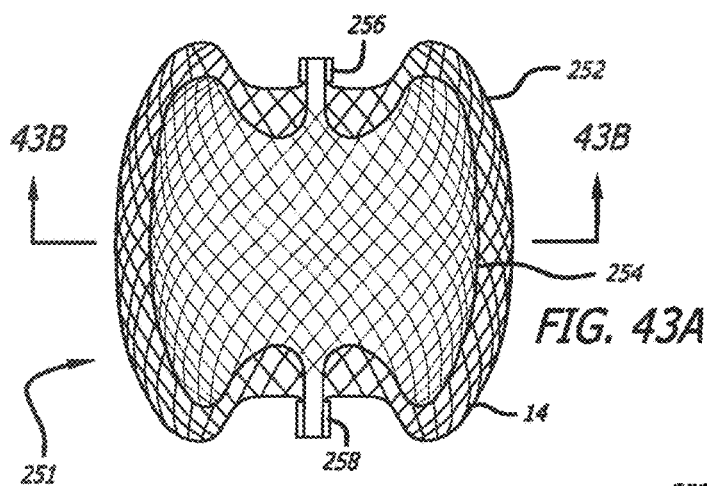
FIG. 43A is an elevation view in section that illustrates an embodiment of a device for treatment of a patient's vasculature.
Figure 43B:
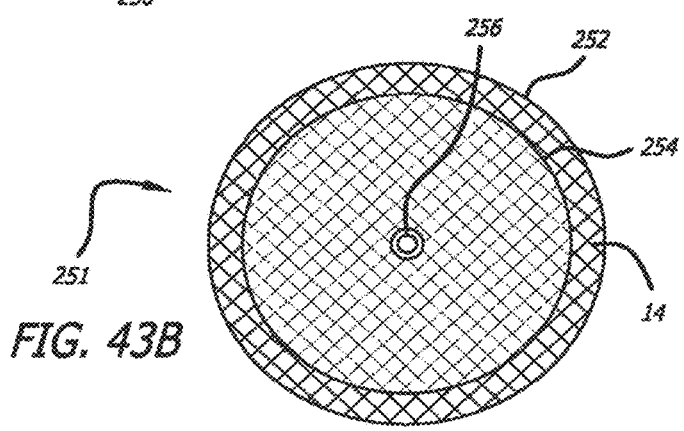
FIG. 43B is a sectional view of the device of FIG. 43A taken along lines 43B-43B of FIG. 43A.

FIG. 41 shows another embodiment of a fixture for shape setting the permeable shell 40 of a device for treatment of a patient's vasculature. The fixture embodiment 230 of FIG. 41 may be used in essentially the same manner as the fixture embodiment 220 of FIG. 40, except that instead of a central ball mandrel 212, an internal tube mandrel 232 is used in conjunction with an external tube restraint 234 in order to hold the shape of the braided tubular member 208 during the heat setting process. More specifically, the tubular braided member 208 is disposed over an internal rod mandrel 210 that extends through central lumens of the internal tube mandrel 232 and a pair of opposed recessed end forming mandrels 214. The tubular braided member 208 is also disposed over an outer surface of the internal tube mandrel 232 and within an inner lumen of each of the end forming mandrels 214.

In order to hold the braided tubular member 208 into a desired shape, including the recessed ends thereof, the end forming mandrels 214 are configured to be pushed against and into recessed ends 238 of the internal tube mandrel 232 such that the inside surface of the braided tubular member 208 is held against the outer contour of the internal tube mandrel 232 and fixed in place at the ends of the tube mandrel 232. Between the ends of the tube mandrel 232, the braided tubular member 208 radially expands outwardly until it touches and is radially constrained by an inside surface of an external tube mandrel 234. The combination of axial restraint and securement of the braided tubular member 208 at the ends of the internal tube mandrel 232 in conjunction with the inward radial restraint on an outside surface of the braided tubular member 208 disposed between the proximal and distal ends thereof, may be configured to produce a desired globular configuration suitable for the permeable shell 40 of the device 10.

Once again, this entire fixture 230 with the inside surface of the ends of the braided tubular structure 208 held against the outside surface of the ends of the internal tube mandrel 232 and an outside surface of the braided tubular member 208 radially constrained by an inside surface 233 of the external tube member 234, may then be subjected to an appropriate heat treatment. The heat treatment may be configured such that the resilient filaments 14 of the braided tubular member 208 assume or are otherwise shape-set to the globular contour of the filaments 14 generated by the fixture 230. In some embodiments, the filamentary elements 14 of the permeable shell 40 may be held by a fixture configured to hold the braided tubular member 208 in a desired shape and heated to about 475-525 degrees C. for about 5-10 minutes to shape-set the structure. The internal tube mandrel 232 and inside surface 233 of the external tube member 234 may be so configured to have any desired shape so as to produce a shape set tubular braided member 208 that forms a permeable shell 40 having a desired shape and size such as the globular configuration of the device of FIG. 3-6 above, or any other suitable configuration.

For some embodiments, material may be attached to filaments 14 of the permeable shell 40 of a device 10 such that it substantially reduces the size of the fenestrations, cells or pores 64 between filaments 14 and thus reduces the porosity in that area. For example, coating embodiments may be disposed on portions of the filaments 14 to create small fenestrations or cells and thus higher density of the permeable shell 40. Active materials such as a responsive hydrogel may be attached or otherwise incorporated into permeable shell 40 of some embodiments such that it swells upon contact with liquids over time to reduce the porosity of the permeable shell 40.

Device embodiment 10 and any other suitable device embodiment discussed herein may be coated with various polymers to enhance it performance, fixation and/or biocompatibility. In addition, device embodiments 10 may be made of various biomaterials known in the art of implant devices including but not limited to polymers, metals, biological materials and composites thereof. Device embodiments discussed herein may include cells and/or other biologic material to promote healing. Device embodiments discussed herein may also be constructed to provide the elution or delivery of one or more beneficial drugs, other bioactive substances or both into the blood or the surrounding tissue.

In some cases, permeable shell embodiments 40 of devices for treatment of a patient's vasculature 10 may include multiple layers. A first or outer layer may be constructed from a material with low bioactivity and hemocompatibility so as to minimize platelet aggregation or attachment and thus the propensity to form clot and thrombus. Optionally, an outer layer may be coated or incorporate an antithrombogenic agent such as heparin or other antithrombogenic agents described herein or known in the art. One or more inner layers disposed towards the vascular defect in a deployed state relative to the first layer may be constructed of materials that have greater bioactivity and/or promote clotting and thus enhance the formation of an occlusive mass of clot and device within the vascular defect. Some materials that have been shown to have bioactivity and/or promote clotting include silk, polylactic acid (PLA), polyglycolic acid (PGA), collagen, alginate, fibrin, fibrinogen, fibronectin, Methylcellulose, gelatin, Small Intestinal Submucosa (SIS), poly-N-acetylglucosamine and copolymers or composites thereof.

Bioactive agents suitable for use in the embodiments discussed herein may include those having a specific action within the body as well as those having nonspecific actions. Specific action agents are typically proteinaceous, including thrombogenic types and/or forms of collagen, thrombin and fibrogen (each of which may provide an optimal combination of activity and cost), as well as elastin and von Willebrand factor (which may tend to be less active and/or expensive agents), and active portions and domains of each of these agents. Thrombogenic proteins typically act by means of a specific interaction with either platelets or enzymes that participate in a cascade of events leading eventually to clot formation. Agents having nonspecific thrombogenic action are generally positively charged molecules, e.g., polymeric molecules such as chitosan, polylysine, poly(ethylenimine) or acrylics polymerized from acrylimide or methacrylamide which incorporate positively-charged groups in the form of primary, secondary, or tertiary amines or quarternary salts, or non-polymeric agents such as (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

Device embodiment 10 and any other suitable device embodiment discussed herein may include a surface treatment or coating on a portion, side or all surfaces that promotes or inhibits thrombosis, clotting, healing or other embolization performance measure. The surface treatment or coating may be a synthetic, biologic or combination thereof. For some embodiments, at least a portion of an inner surface of the permeable shell 40 may have a surface treatment or coating made of a biodegradable or bioresorbable material such as a polylactide, polyglycolide or a copolymer thereof. Another surface treatment or coating material which may enhance the embolization performance of a device includes a polysachharide such as an alginate based material. Some coating embodiments may include extracellular matrix proteins such as ECM proteins. One example of such a coating may be Finale Prohealing coating which is commercially available from Surmodics Inc., Eden Prairie, Minn. Another exemplary coating may be Polyzene-F which is commercially available from CeloNovo BioSciences, Inc., Newnan, Ga. In some embodiments, the coatings may be applied with a thickness that is less than about 25% of a transverse dimension of the filaments 14.

Antiplatelet agents may include aspirin, glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban), dipyridamole, apo-dipyridamole, persantine, prostacyclin, ticlopidine, clopidogrel, cromafiban, cilostazol, and nitric oxide. To deliver nitric oxide, device embodiments may include a polymer that releases nitric oxide. Device embodiments 10 may also deliver or include an anticoagulant such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors.

In some embodiments, the permeable shell 40 of a device 10 may be coated with a composition that may include nanoscale structured materials or precursors thereof (e.g., self-assembling peptides). The peptides may have with alternating hydrophilic and hydrophobic monomers that allow them to self-assemble under physiological conditions. The composition may comprise a sequence of amino acid residues. In some embodiments, the permeable shell may include a thin metallic film material. The thin film metal may be fabricated by sputter deposition and may be formed in multiple layers. The thin film may be a nickel-titanium alloy also known as nitinol.

FIGS. 42-49 illustrate device embodiments for treatment of a patient's vasculature that may be deployed by the same or similar methods and devices as those discussed above. The device embodiments illustrated in FIGS. 42-49 may have some or all of the suitable features, dimensions and materials as those of the device embodiments discussed above. In some instances, saccular aneurysms may have a generally circular flow dynamic of blood as indicated by arrows 250 shown in FIG. 42. While the shell of a single layer device, such as device 10, slows flow into the aneurysm, thrombosis and embolization may be further enhanced by an internal porous structure. In particular, a structure that is formed so that the circular flow 250, and in particular the highest velocity region is forced to pass through one or more porous layers may have a synergistic treatment effect and promote rapid thrombosis. In some embodiments, the device 251 may include a shell 252 of filamentary members 14 and an inner structure 254 of filamentary members 14 as shown in FIGS. 43A and 43B.

Both the shell 252 and inner structure 254 as well as other components of device 251 may have the same or similar features, dimensions or materials as those of device 10 or any other suitable device or component thereof discussed herein, including embodiments 266, 280, 290, 310, 336, 360, 370, 376 and 390. In particular, the mesh or woven structure of the shell 252 and inner structure 254 may have the same or similar filament configuration, pore size, radial stiffness, collapsed profile etc. as device 10 discussed above as well as the other embodiments. Device 251 may also be manufactured or deployed by the same or similar methods as those discussed above with respect to the manufacture and deployment of device 10 as well as the deployment methods discussed below.

Figure 44:
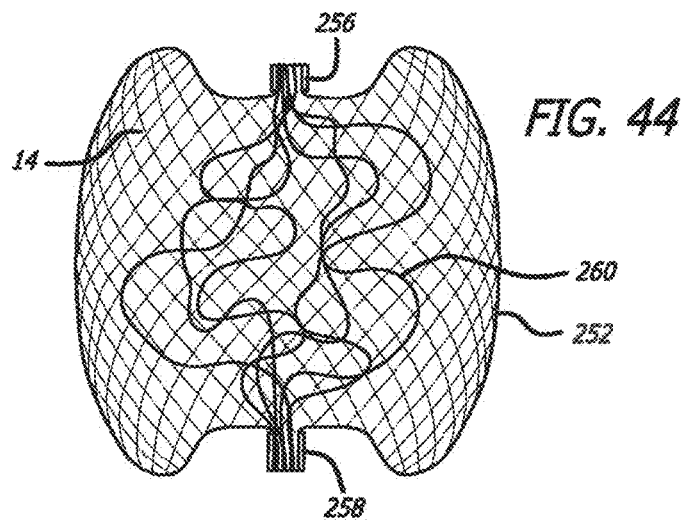
FIG. 44 is an elevation view in partial section that illustrates an embodiment of a device for treatment of a patient's vasculature.

In some embodiments, the inner structure 254 forms a shape that has at least a portion which parallels the shell 252. The distal ends of the inner structure members or filaments 14 may be connected to the shell members at a distal shell hub 256. Proximal ends of the filaments 14 may be similarly connected by a proximal shell hub 258. The inner structure 254 may have a collapsed length that is substantially the same as the collapsed length of the outer shell 252 as shown in FIGS. 43C and 43D. If the inner structure 254 has a substantially longer collapsed length than the shell 252, buckling may occur when the shell 252 and inner structure 254 are collapsed. If the inner structure 254 has a length substantially shorter collapsed length than the shell 252, it may restrict collapse of the shell 252 as it will be fully elongated before the shell. With a substantially similar length, collapse of the shell 252 will not be significantly restricted and buckling of the inner structure 254 will be minimized. Any buckling would result in an increase of the collapsed device volume and thus increase the diameter of the catheter required for delivery. The inner structure 254 may have an overall shape, including but not limited to a sphere, ovoid, conical, or barrel-like shape. Alternatively, an inner structure 260 disposed within shell 252 may have a random or irregular shape as shown in the embodiment of FIG. 44. The inner structure filaments 14 shown in inner structure 260 of the device embodiment of FIG. 44 may also have a number of undulations, convexities or concavities. These undulations may act as internal baffles to intra-device blood flow increasing the hemostatic performance of the device.

Figure 45A:
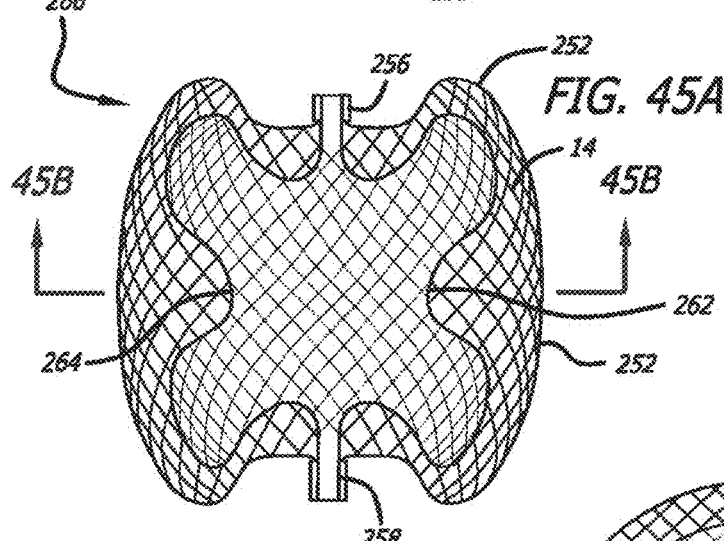
FIG. 45A is an elevation view in section that illustrates an embodiment of a device for treatment of a patient's vasculature.
Figure 45B:
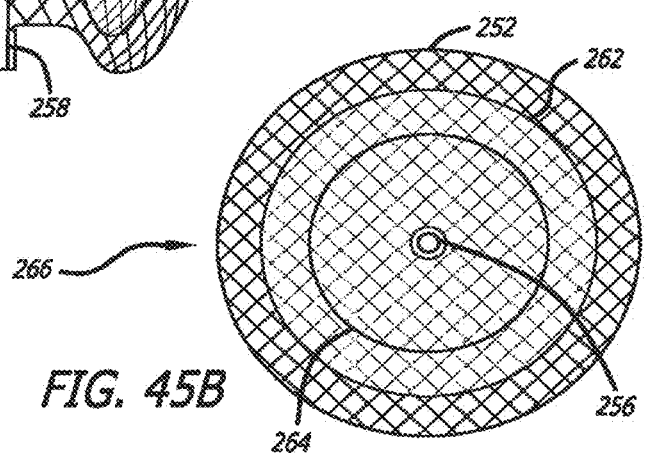
FIG. 45B is a transverse sectional view of the device of FIG. 45A taken along lines 45B-45B of FIG. 45A.

In some device embodiments, the undulations of the filamentary members 14 of a woven inner structure embodiment 262 disposed within the shell 252 may also form a radial groove or depression 264 around the circumference of the inner structure 262 as shown in the device embodiment 266 of FIGS. 45A and 45B. In some embodiments, the smallest transverse diameter or distance through the device center between two diametrically opposed concavities may be less than about 80% of the nominal device diameter. In many aneurysms, the highest flow velocities would typically be near the periphery of the aneurysm 160 a short distance from the aneurysm wall. Thus, the undulations would provide multiple porous layers through which the highest velocity blood must pass. Therefore, the inner structure 262 may provide baffling and flow disruption in the region of the aneurysm 160 most needed to achieve rapid embolization. In some embodiments, the inner structure 262 may touch or lay against one or more portions of the shell 252. As shown in FIG. 46, the inner structure 262 of device 266 may be in close proximity or even touching the shell 252 in the area 268 where the shell 252 engages an aneurysm neck. This close proximity would have the effect of decreasing the porosity in that region 268 which may be the in-flow zone or region of highest flow into the aneurysm 160. Thus the inner structure 262 may enhance the flow reduction into the aneurysm 160. A close proximity inner structure 262 may also provide increased stiffness in the area 268 where the device is adjacent to and seals the neck or opening of an aneurysm 160.

Figure 47:
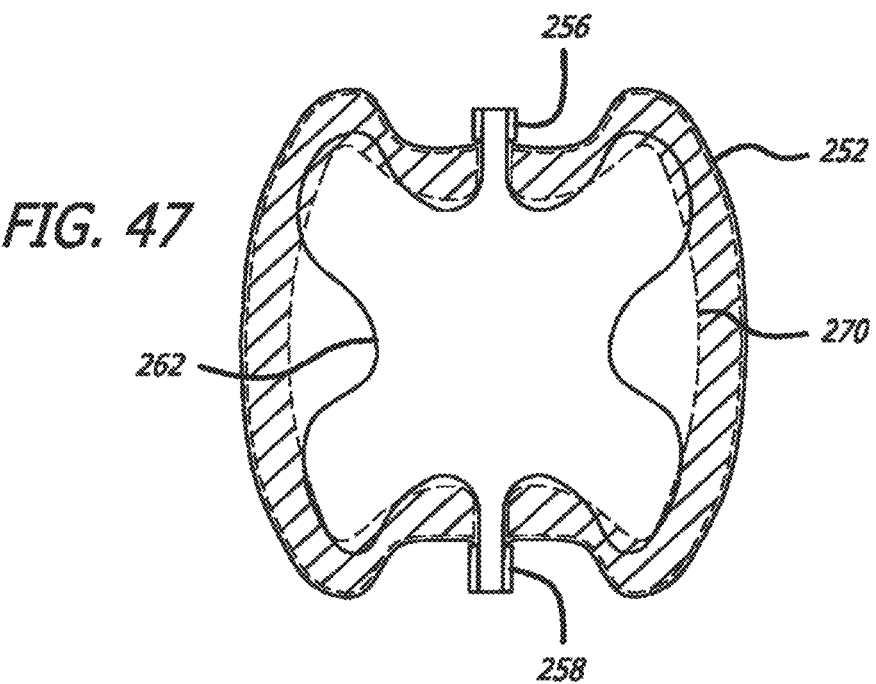
FIG. 47 is an elevation view in section that illustrates an embodiment of a device for treatment of a patient's vasculature.
Figure 48:
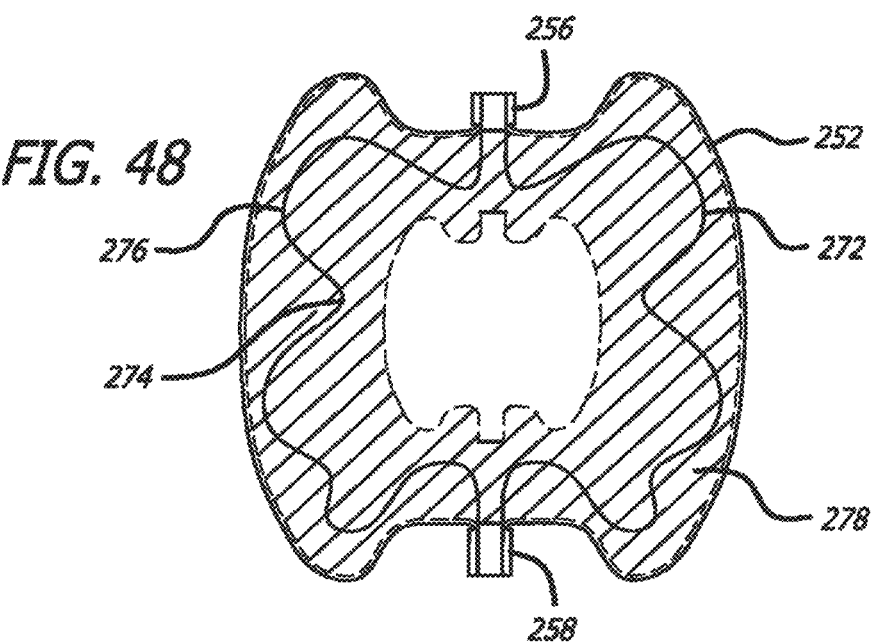
FIG. 48 is an elevation view in section that illustrates an embodiment of a device for treatment of a patient's vasculature.

In some embodiments of devices for treatment of a patient's vasculature, the inner structure 262 may be formed so that at least about 10% of its mass is contained within an "inner volume" 270 of the shell, defined as the volume created by the internal 80% of the shell volume as shown in FIG. 47. In some embodiments, the inner structure 272 forms an undulating shape that alternates between concave surfaces 274 and convex surfaces 276 substantially within a zone defined by the outermost 75% of the internal volume 278 of the shell 252 as shown in FIG. 48.

Both the shell and inner structure as well as other components of device 266 may have the same or similar features, dimensions or materials as those of device 10 or any other suitable device or component thereof discussed herein, including embodiments 251, 280, 290, 310, 336, 360, 370, 376 and 390. In particular, the mesh or woven structure of the shell 252 and inner structure 262 may have the same or similar filament configuration, pore size, radial stiffness, collapsed profile etc. as device 10 discussed above as well as the other embodiments. Device 266 may also be manufactured or deployed by the same or similar methods as those discussed above with respect to the manufacture and deployment of device 10 as well as the deployment methods discussed below.

Figure 49:
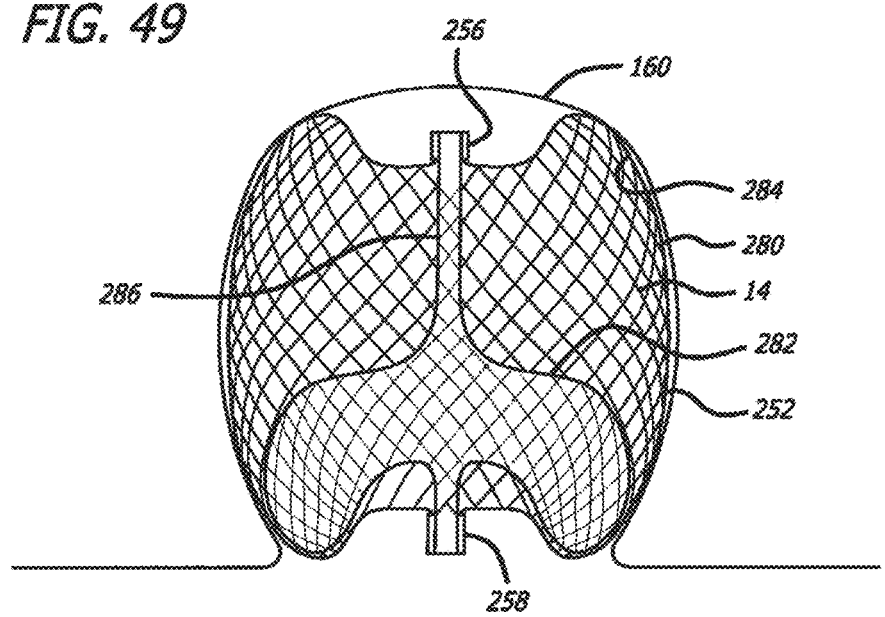
FIG. 49 is an elevation view of an embodiment of a device for treatment of a patient's vasculature.

FIG. 49 illustrates an embodiment of a device for treatment of a patient's vasculature 280 having an inner structure 282 that does not conform to all of the inner surface 284 of an outer structure or shell 252 of the device 280. In some embodiments, the inner structure 282 may have a disk-like shape. In some embodiments, the inner structure 282 may have a torus-like shape as shown in FIG. 49. In some embodiments, the inner structure 282 may include a column of wires 286 that form a cylindrical support substantially along a vertical axis of the device 280. This support member 286 may serve to facilitate the stability of the inner structure 282 within the lower half of the shell. Both the shell 252 and inner structure 282 as well as other components of device 280 may have the same or similar features, dimensions or materials as those of device 10 or any other suitable device or component thereof discussed herein, including embodiments 251, 266, 290, 310, 336, 360, 370, 376 and 390. In particular, the mesh or woven structure of the shell 252 and inner structure 282 may have the same or similar filament configuration, pore size, radial stiffness, collapsed profile etc. as device 10 discussed above as well as the other embodiments. Device 280 may also be manufactured or deployed by the same or similar methods as those discussed above with respect to the manufacture and deployment of device 10 as well as the deployment methods discussed below.

Now referring to FIGS. 50-54, other embodiments of a device for treatment of a patient's vasculature are illustrated. In some embodiments a device for treatment of a patient's vasculature 290 includes a self-expanding resilient permeable structure 292 having a proximal end 294, a distal end 296, and a longitudinal axis 298. The permeable structure 292 may have a radially constrained elongated state configured for delivery within a microcatheter 61. In an expanded relaxed state the permeable structure 292 may have a globular and longitudinally shortened configuration relative to the radially constrained state and extends along the longitudinal axis 298 between the proximal end 294 and distal end 296. The permeable structure 292 may further include a plurality of elongate resilient filaments 14 secured relative to each other at either or both the proximal ends and distal ends 294 and 296 of the structure. The filaments form a resilient permeable shell 292 having proximal and distal ends 294 and 296 and defining a cavity or interior volume 300 and at least one inner structure 302 disposable within the cavity 300 of the shell 292. The resilient filaments 14 forming the shell 292 and the at least one inner structure 302 may be contiguous with one another as shown in FIG. 50A.

Figure 50:
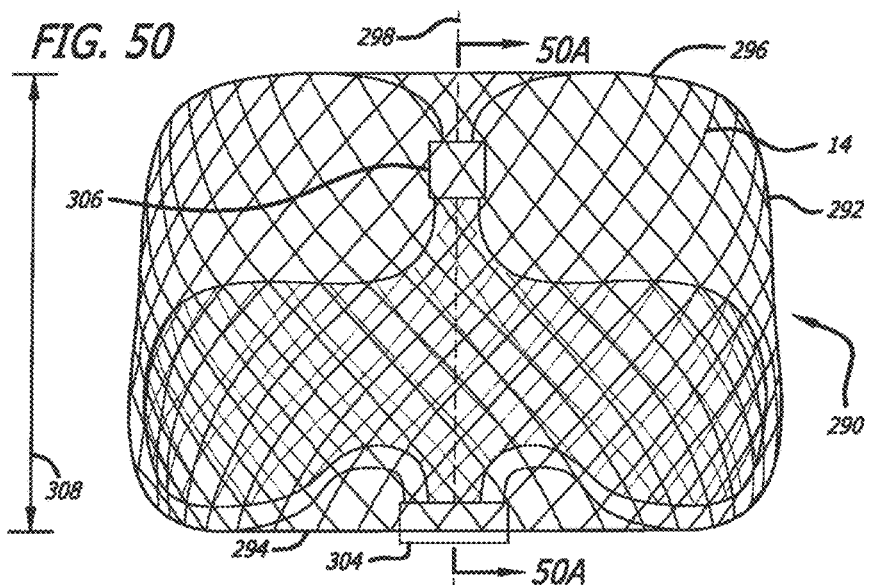
FIG. 50 is an elevation view of an embodiment of a device for treatment of a patient's vasculature.
Figure 50A:
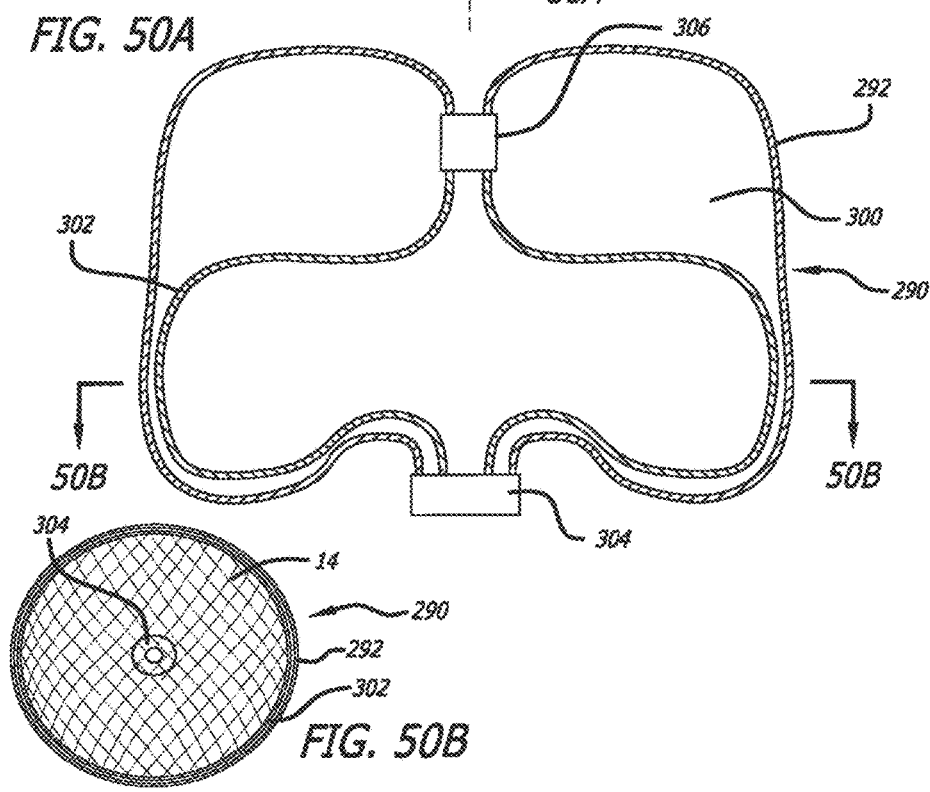
FIG. 50A is a cross-sectional view of the embodiment of FIG. 50 taken along lines 50A.

In some embodiments, the inner structure 302 passes through a cylindrical member or hub 304 that is attached to the proximal end 294 of the shell 292 as shown in FIGS. 50 and 50A. In this embodiment, the shell 292 and inner structure 302 are formed from a contiguous flexible elongate member, such as a tubular braid, that is inverted at one or more ends. A distal hub or marker 306 may be placed on the portion of the filaments where they come together just below the inverted portion of the shell within the shell cavity. Various methods of connecting the shell filaments 14 to the cylindrical member 304 may be employed including welding, soldering and the like as described herein. In the embodiment shown, the shell 292 and the inner filaments or structure 302 form different contours.

In some embodiments, the distal hub or marker 306 may be positioned below the top or distal surface 296 of the device 290 at a distance from the most distal surface which may be at least about 10% of the device height as indicated by arrow 308. In some embodiments, the distal hub or marker 306 may be positioned just below the top or distal surface 296 of the device at a distance which is less than about 10% of the device height. Both the shell 292 and inner structure 302 of device 290 may have the same or similar features, dimensions or materials as those of device 10 or any other suitable device or component thereof discussed herein, including embodiments 251, 266, 280, 310, 336, 360, 370, 376 and 390. In particular, the mesh or woven structure of the shell 292 and inner structure 302 may have the same or similar filament configuration, pore size, radial stiffness, collapsed profile etc. as device 10 discussed above as well as the other embodiments. Device 290 may also be manufactured or deployed by the same or similar methods as those discussed above with respect to the manufacture and deployment of device 10 as well as the deployment methods discussed below.

Figure 50B:
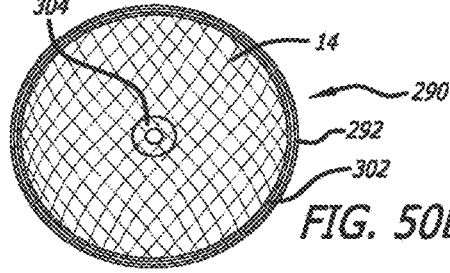
FIG. 50B is a cross-sectional view of the embodiment of FIG. 50A taken along lines 50B.
Figure 51:
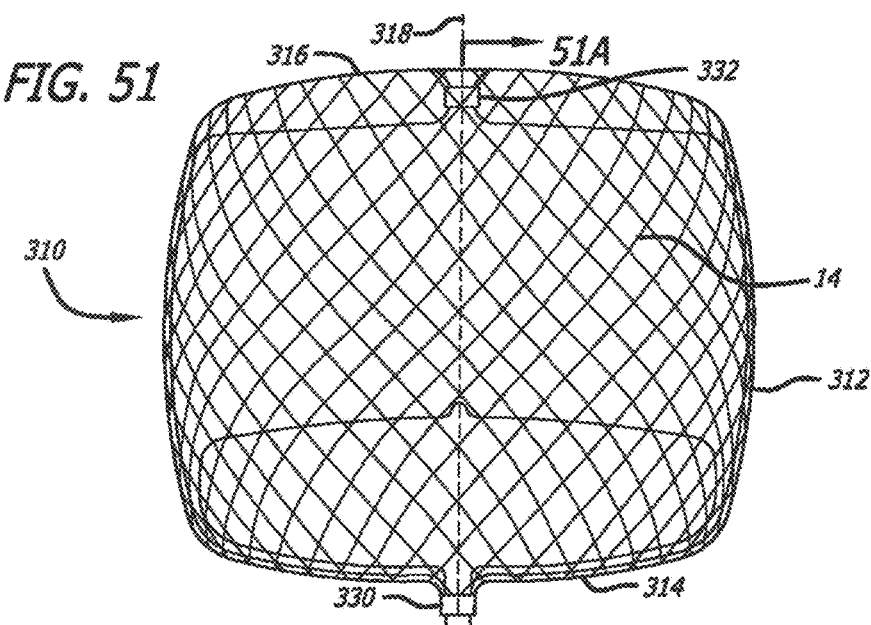
FIG. 51 is an elevation view of an embodiment of a device for treatment of a patient's vasculature.
Figure 51A:
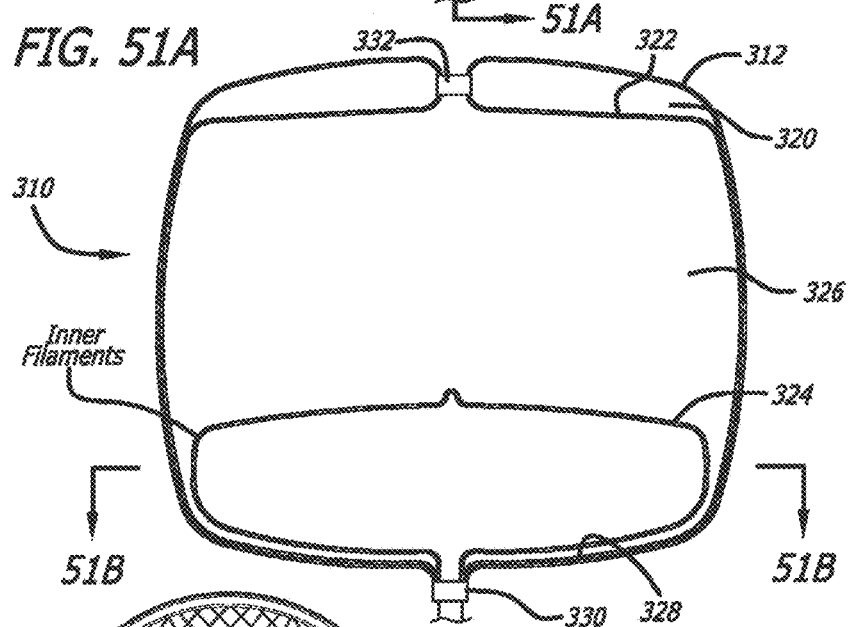
FIG. 51A shows the embodiment of FIG. 51 in partial section.
Figure 51B:
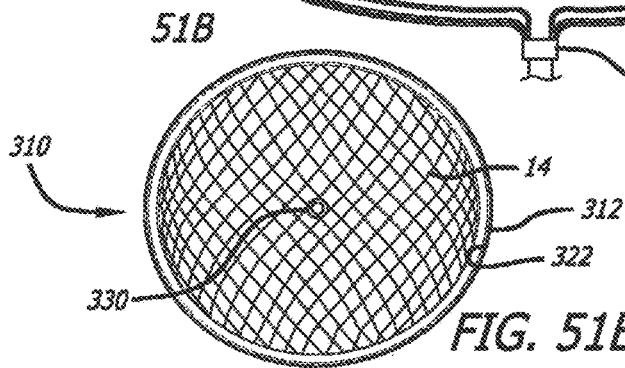
FIG. 51B is a cross-sectional view of the embodiment of FIG. 51A taken along lines 51B-51B of FIG. 51A.

FIGS. 51-51B show an embodiment of a device for treatment of a patient's vasculature 310 that has a structure similar to that of the device for treatment of a patient's vasculature 290 shown in FIGS. 50-50B. The device 310 of FIGS. 51-51B includes a self-expanding resilient permeable structure 312 having a proximal end 314, a distal end 316, and a longitudinal axis 318. The permeable structure 312 may have a radially constrained elongated state configured for delivery within a microcatheter. In an expanded relaxed state the permeable structure 312 may have a globular and longitudinally shortened configuration relative to the radially constrained state and extends along the longitudinal axis 318 between the proximal end 314 and distal end 316. The permeable structure 312 may further include a plurality of elongate resilient filaments 14 secured relative to each other at either or both the proximal end 314 and distal end 316 of the structure 312. The filaments 14 form the resilient permeable shell 312 defining a cavity or interior volume 320 and at least one first inner structure 322 disposable within the cavity of the shell.

The resilient filaments 14 forming the outer shell 312 and at least one first inner structure 322 may be contiguous with one another as shown in FIG. 51A. The first inner structure 322 is disposed within the interior volume 320 of the outer permeable shell 312 and conforms substantially to the contour of the outer permeable shell 312. The device for treatment of a patient's vasculature 310 also includes a second inner structure 324 disposed within an interior volume 326 of the first inner structure 322. The second inner structure 324 is disposed at or biased towards the proximal end 328 of the interior volume 326 of the first inner structure 322 so as to dispose the woven mesh structure of the second inner structure 324 towards the proximal end 314 of the device 310.

In some cases, the inner structure 322 passes through a cylindrical member or hub 330 that is attached to the proximal end 314 of the shell 312 as shown in FIGS. 51 and 51A. The shell 312 and inner structure 302 are formed from a contiguous flexible elongate member, such as a tubular braid, that is inverted at one or more ends. A distal hub or marker 332 may be placed on the portion of the filaments 14 where they come together just below the inverted portion of the shell 312 within the shell cavity 320. Both the shell 312 and inner structure 302 as well as other components of device 310 may have the same or similar features, dimensions or materials as those of device 10 or any other suitable device or component thereof discussed herein, including embodiments 251, 266, 280, 290, 336, 360, 370, 376 and 390. In particular, the mesh or woven structure of the shell 312 and inner structure 302 may have the same or similar filament configuration, pore size, radial stiffness, collapsed profile etc. as device 10 discussed above as well as the other embodiments. Device 310 may also be manufactured or deployed by the same or similar methods as those discussed above with respect to the manufacture and deployment of device 10 as well as the deployment methods discussed below.

Figure 52B:
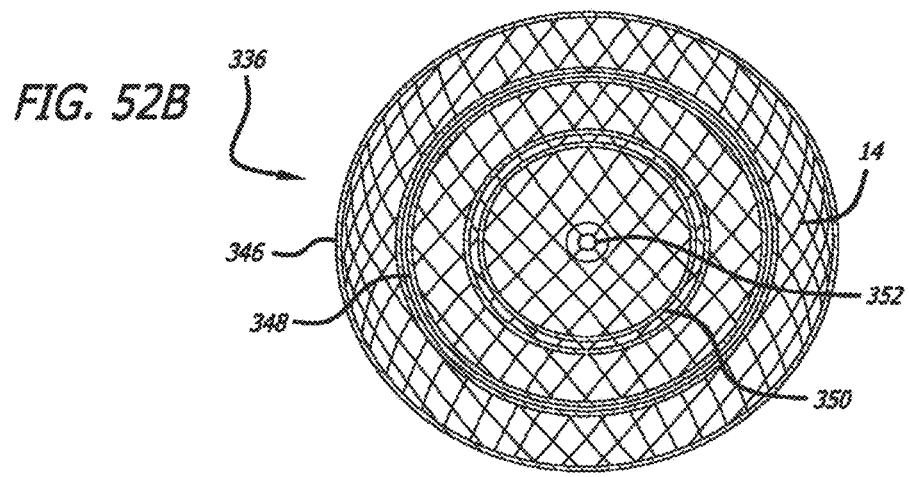
FIG. 52B is a cross-sectional view of the embodiment of FIG. 52A taken along lines 52B-52B of FIG. 52A.

Some embodiments of a device for treatment of a patient's vasculature 336 include one cylindrical mesh or braid 337 that is inverted at least once to form a plurality of concentric radial layers or lobes 338, as shown in FIG. 52. As shown, the inversion(s) and lobes 338 may be disposed at or biased towards a proximal end 340 of the device along a longitudinal axis 339 of the device 336. The device as a whole may have a generally globular "mushroom-shaped" configuration with a domed distal end and a substantially straight or flat proximal end surface formed by the proximal extremities of the lobes. For some embodiments, the axial or longitudinal length of the device 336 may be smaller than a transverse dimension of the device overall, but at least about one half the transverse dimension. Thus, multiple radial layers may be achieved with a single contiguous structure. In some embodiments, the inner structure may comprise a plurality of inner structures formed integrally with one another. In some embodiments, the number of inversions or lobes 338 may range from about 1 to about 5. One embodiment, as shown in FIGS. 52A and 52B, has three inversions with three distinct lobes 338. The lobes include an outer lobe 346, a middle lobe 348 and an inner lobe 350. The proximal ends of each of the lobes 346, 348 and 350 are substantially aligned with the proximal end 340 of the device 336. The lobes 338 formed by the inversions may be configured in a telescoping manner nested inside one another such that the lobe 338 with a smaller diameter is disposable within a cavity formed by the lobe 338 of the next highest diameter, as shown in FIG. 52A. The mesh 337 terminates at a distal end 342 of the device 336 at a distal hub 344 which constrains the filaments 14 of the mesh 337. The mesh 337 terminates at the proximal end 340 of the device at a proximal hub 352. For some embodiments, the outer lobe 346 may have an outer transverse dimension of about 5 mm to about 30 mm.

Figure 52C:
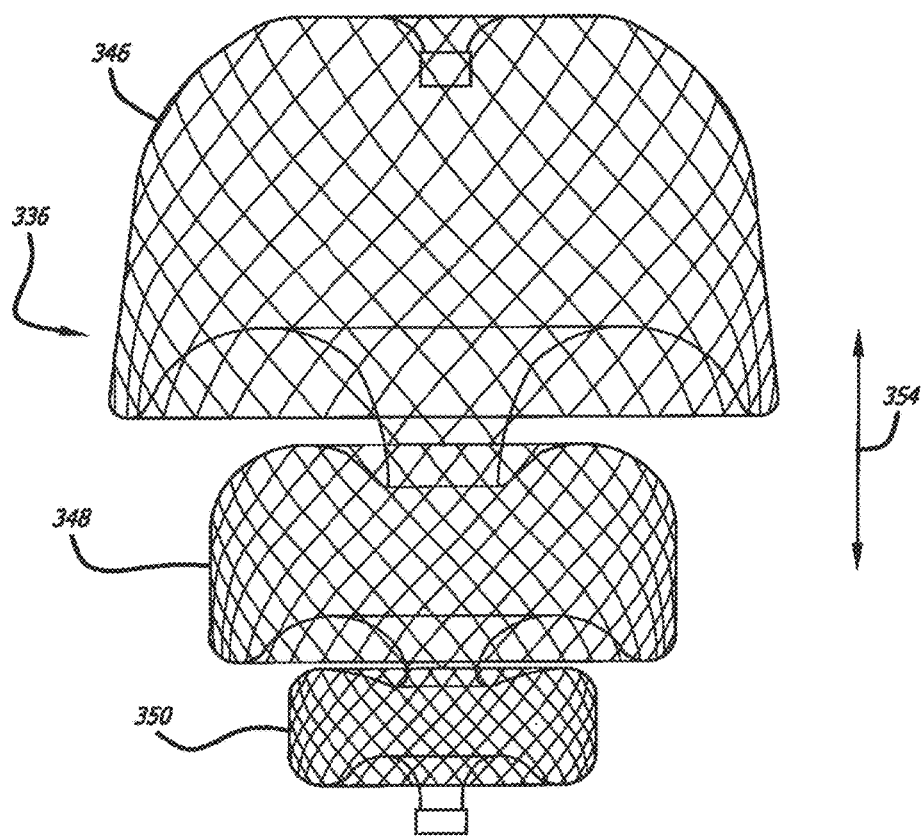
FIG. 52C is a cross-sectional view of the device of FIG. 52 slightly under axial tension.

Now referring to FIG. 52C the braid of the device 336 is partially elongated under low axial tension as indicated by arrow 354 to show a plurality of lobes 346, 348 and 350. As shown, three lobes 346, 348 and 350 nest within each other in order to form the multiple radial layers or lobes in the relaxed state as shown in FIG. 52. The multiple concentric radial layers may be particularly beneficial to slow blood flow in side-wall aneurysms. Blood that circulates in the aneurysm 160 must flow through multiple layers of mesh 337 to complete one circular flow path. Baffling of the circular flow provides flow disruption leading to rapid hemostasis and thrombosis. As shown, the telescoping configuration of device 336 of FIG. 52 includes outer (e.g., shell) lobe 346, inner or middle lobe 348, and most inner layers or lobes 350. The elongation or expansion may be contained until the device 336 is reduced sufficiently in transverse dimension so as to fit within an inner lumen of a microcatheter 61 as shown in FIG. 52D. Delivery from such a microcatheter 61 may be carried out as discussed above with respect to device 10.

The shell of device 336 as well as other components may have the same or similar features, dimensions or materials as those of device 10 or any other suitable device or component thereof discussed herein, including embodiments 251, 266, 280, 290, 310, 360, 370, 376 and 390. In particular, the mesh or woven structure of the shell 252 and inner structure 254 may have the same or similar filament configuration, pore size, radial stiffness, collapsed profile etc. as device 10 discussed above as well as the other embodiments. Device 336 may also be manufactured or deployed by the same or similar methods as those discussed above with respect to the manufacture and deployment of device 10 as well as the deployment methods discussed below.

In any of the embodiments described herein, the inner or inverted structure(s) may provide a high surface area internal flow baffle. In some embodiments, the total surface area of the inner or inverted structure(s) may be greater than about 100 mm². In some embodiments, the total surface area of the inner or inverted structure(s) may be between about 100 mm² and 500 mm² for each centimeter of the device's largest dimension. For example, with a 1.5 cm (diameter or length) device, the surface area of the inner or inverted structure(s) may be between about 150 mm² and 750 mm². Conversely, with a 0.5 cm (diameter or length) device, the surface area of the inner or inverted structure(s) may be between about 50 mm² and 250 mm².

In any of the embodiments described herein, the inner or inverted structure(s) or shells may be disposed substantially or completely within the lower or proximal portion of the shell of the device 360. In some embodiments, the height of the inner or inverted structure(s), as indicated by arrow 362 in FIG. 53, may be less than about 30% of the shell overall height of the device 360, as indicated by arrow 364. In some embodiments, an internal gap between a top or distal end of the inner structure and the inner surface at the distal end of the outer structure, as indicated by arrow 365 in FIG. 55, may be between about 0.2 mm and about 2.5 mm. The internal gap may be less than about 35% of the total height along a longitudinal axis of the device. In some cases, the internal gap may be between about 8% and about 35% of the total longitudinal height of the device measured along the longitudinal axis of the device. The structure, features, dimensions and materials of device 360 of FIG. 53 may otherwise be similar to or the same as those of device 290 of FIG. 50.

In any of the embodiments described herein, including embodiments 251, 266, 280, 290, 310, 336, 360, 370, 376 and 390, the proximal surface or end 294 of the device 370 may be concave, convex, or conical as shown in FIG. 54. Regarding the conical shape of proximal surface of the distal end 294 for the device 370 may provide a more natural diversion or branching of flow particularly for terminal aneurysms. In some embodiments, the inner structure 302, in an expanded state, may form a concave or convex outer surface relative to the shell 292. The conical structure in particular may act as a flow diverting structure extending away from an aneurysm 160 being treated and towards the native vessel adjacent the aneurysm 160. The structure, features, dimensions and materials of the device 370 of FIG. 54 may otherwise be the same as or similar to those of the device 290 of FIG. 50.

Figure 55:
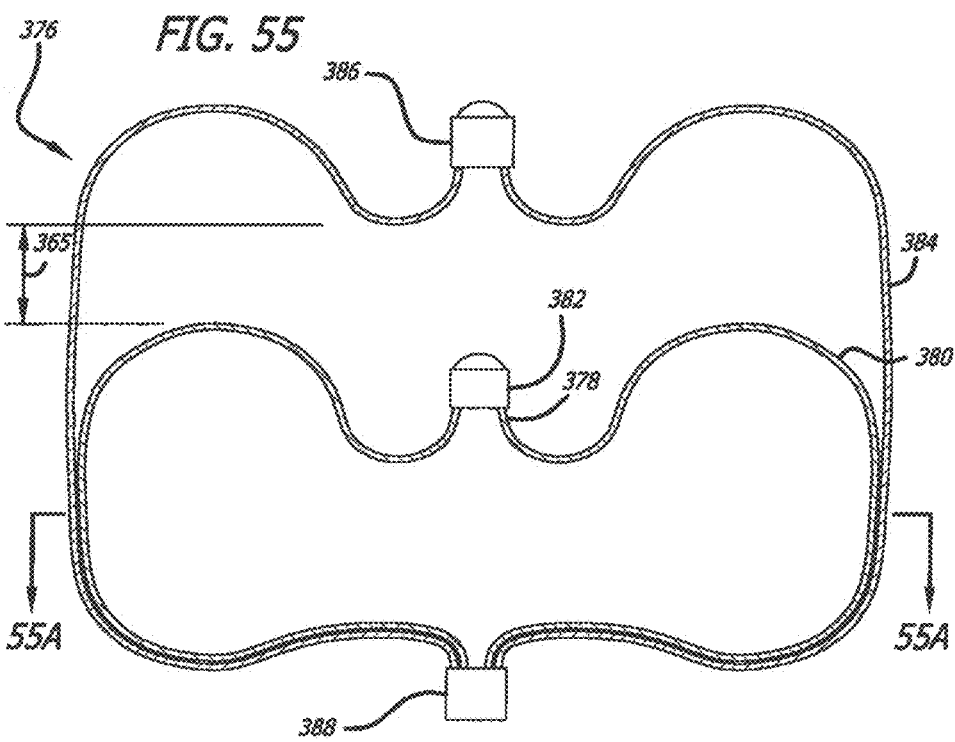
FIG. 55 is an elevation view in partial section of an embodiment of a device for treatment of a patient's vasculature.
Figure 55A:
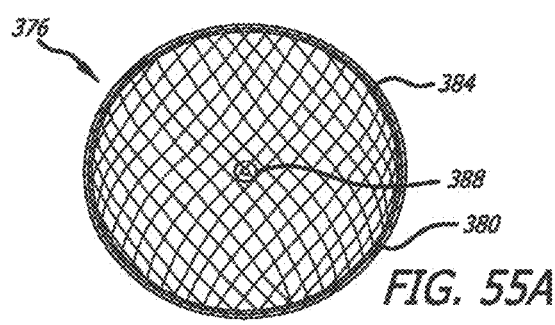
FIG. 55A is a transverse cross section of the device of FIG. 55 taken along lines 55A-55A of FIG. 55.
Figure 55B:
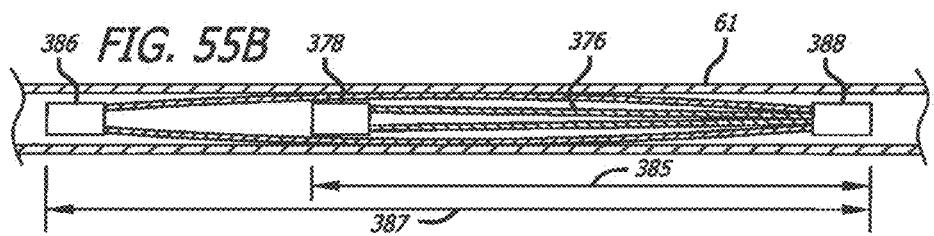
FIG. 55B shows the device of FIG. 55 in a collapsed elongated state.

Referring to FIG. 55, some embodiments of devices for treatment of a patient's vasculature 376 may include a distal end 378 of an inner structure 380 may terminate with a connection or hub 382 as shown in FIG. 55. Thus, the inner structure 380 may define a closed volume that is connected to the shell 384 near the proximal inner surface of the shell. With an internal termination of the inner structure 380, the potential problem of length matching and buckling between the outer shell 384 and the inner structure 380 may be minimized due to the ability of the inner layer or structure 380 to collapse without affecting, or minimally affecting, the collapse or radial compression of the outer layer or shell 384. The internal gap 365 between the inner structure and the outer shell along a longitudinal axis of the device may include the ratios and distances as discussed above. In particular, as discussed above, an internal gap between a top or distal end of the inner structure and the inner surface at the distal end of the outer structure, as indicated by arrow 365 in FIG. 55, may be between about 0.2 mm and about 2.5 mm. The internal gap may be less than about 35% of the total height along a longitudinal axis of the device for some embodiments. In some cases, the internal gap may be between about 8% and about 35% of the total longitudinal height of the device measured along the longitudinal axis of the device.

In some embodiments, the collapsed length of the inner structure 380 may be less than about 80% of the collapsed length of the outer structure 384. In some embodiments, the collapsed length of the inner structure 380 may be less than about 90% of the collapsed length of the outer structure 384. In some embodiments, the inner structure 380 forms a separate lobe from the shell 384. The device embodiment 376 also includes a distal hub 386 for the constraint of the distal ends of the filaments 14 of the shell 384 and a proximal hub 388 to secure or anchor the proximal ends of the filaments 14 of the outer shell 384 and the filaments 14 of the inner structure 380. The overall structure of the inner structure 380 and outer shell 384 of the device of FIG. 55 may generally include any suitable material, dimension or feature of any other embodiment of a device for treatment of a patient's vasculature discussed herein. This includes the sizes, spacing and materials of the filaments 14 of the inner structure and shell as well as the size and configuration of the shell 384 and inner structure 380.

Both the shell 384 and inner structure 380 as well as other components of device 376 may have the same or similar features, dimensions or materials as those of device 10 or any other suitable device or component thereof discussed herein, including embodiments 251, 266, 280, 290, 310, 336, 360, 370 and 390. In particular, the mesh or woven structure of the shell 384 and inner structure 380 may have the same or similar filament configuration, pore size, radial stiffness, collapsed profile etc. as device 10 discussed above as well as the other embodiments. Device 376 may also be manufactured or deployed by the same or similar methods as those discussed above with respect to the manufacture and deployment of device 10 as well as the deployment methods discussed below.

Figure 56:
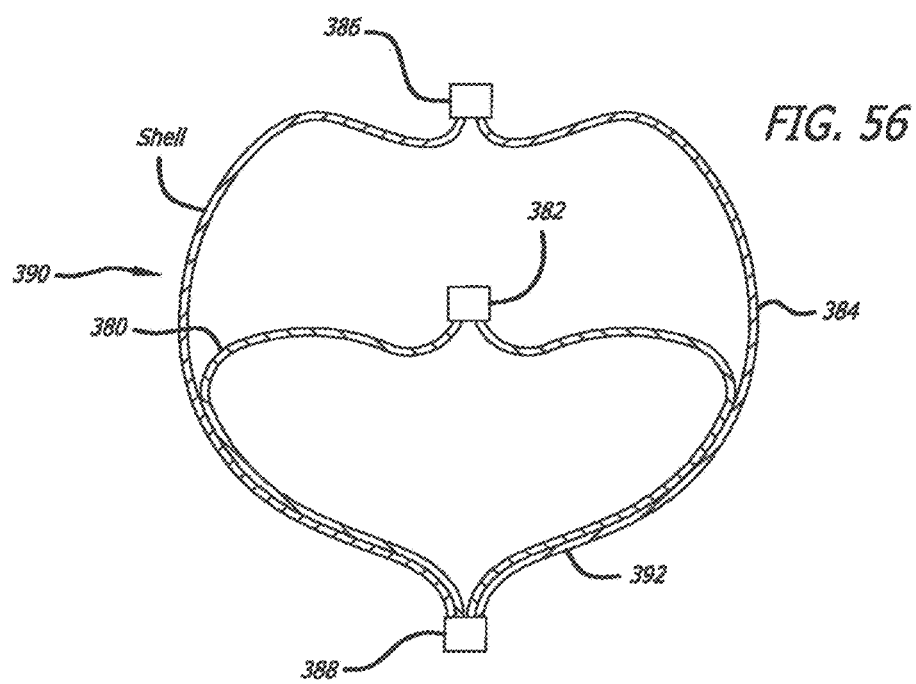
FIG. 56 is an elevation view in partial section of an embodiment of a device for treatment of a patient's vasculature.
Figure 57:
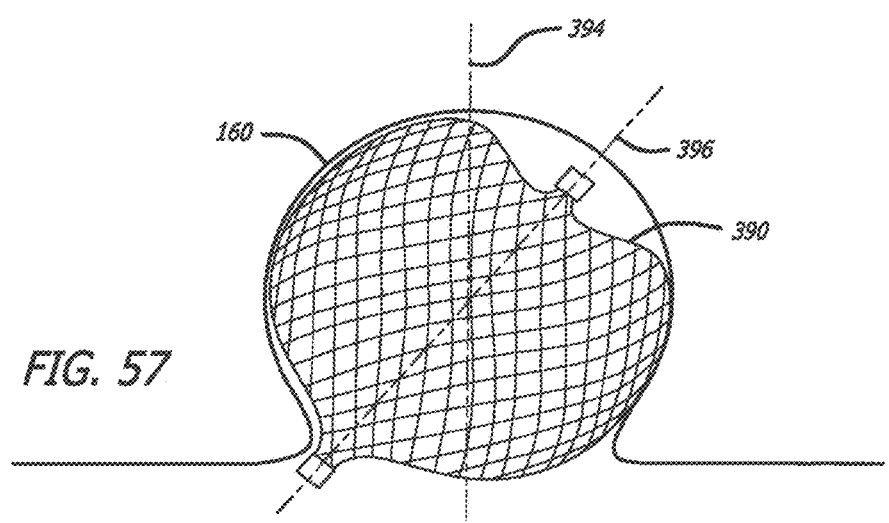
FIG. 57 illustrates the device embodiment of FIG. 56 disposed in an aneurysm.

The device for treatment of a patient's vasculature 390 shown in FIG. 56 may include the same or similar features, dimensions and materials as those of the device embodiment shown in FIG. 55. In the embodiment of FIG. 56, the outer structure 384 may have a truncated sphere or generally heart-like contour in cross-sectional shape. The proximal portion or end 392 of the device 390 may be generally convex or semi-circular. These features may allow the device 390 to be placed into a saccular vascular site such as a cerebral aneurysm 160 at an angled orientation relative to an axis 394 of the aneurysm 160 as shown in FIG. 57. The semi-circular proximal surface 392 presents a relatively constant shape to the parent vessel irrespective of the angulation of the device axis 396.

In some embodiments, the inner structure 380 may be formed such that at least about 80% of the volume of the inner structure 380 is contained within the lower or more proximal half of the outer structure 384 or shell volume. For some embodiments, the mesh density of the inner structure 380 may be higher than a density of the mesh structure of the outer shell or structure 384. In some embodiments, the inner structure 380 may be substantially or entirely within the proximal or lower 80% 398 of the outer shell volume as defined by the boundary shown by the dashed line 400 in FIG. 58.

Figures 59C, 59D:
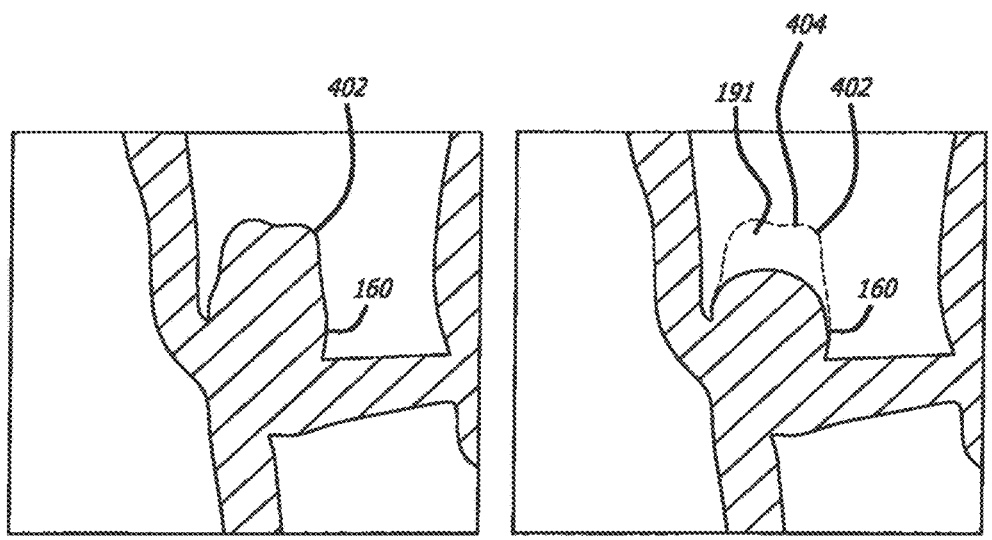
FIG. 59C is a representation of the boundary of the blood flow within the aneurysm and the patient's vasculature near the aneurysm shown in FIG. 59A.
FIG. 59D is a representation of the boundary of the blood flow within the aneurysm and the patient's vasculature near the aneurysm shown in FIG. 59B ten (10) minutes post-treatment with a dashed line indicating the boundary prior to treatment.

The inner structure 380 occupying the lower portion 398 of the outer shell 384 may provide rapid progression of thrombosis particularly in the distal portion 402 of an aneurysm 160. In some embodiments, this configuration may provide protection of the distal "dome" portion of an aneurysm 160 where it is generally thought to be the weakest and most prone to rupture. Thus, embodiments with proximal inner structures 380 may provide a method of rapidly occluding a distal portion 402 of an aneurysm 160 that is visible under angiography. An embodiment of this process is illustrated in the angiographic images, shown in FIGS. 59A and 59B of a model aneurysm 160 created in an animal for purpose of evaluating a device embodiment. FIG. 59A is the pre-treatment angiogram of an aneurysm 160 created in an animal model prior to treatment with an embodiment of a device for treatment of a patient's vasculature having some similarity in structure to the device embodiment shown in FIG. 55. FIG. 59B is representative of an angiogram ten (10) minutes post treatment with the device for treatment of a patient's vasculature showing rapid occlusion of the distal portion 402 of the aneurysm 160. FIG. 59C is a representation of the boundary of the blood flow within the aneurysm 160 and the patient's vasculature near the aneurysm 160 shown in FIG. 59A. FIG. 59D is a representation of the boundary of the blood flow within the aneurysm 160 and the patient's vasculature near the aneurysm 160 shown in FIG. 59B ten (10) minutes post-treatment with a dashed line 404 indicating the boundary of the aneurysm 160 prior to treatment. The space between the solid line of the boundary of the blood flow and the dashed line 404 indicating the boundary prior to treatment as shown in FIG. 59D represents a volume of thrombosis or other form of restricted blood flow in the volume that isolates the dome of the aneurysm 160.

For some embodiments, the inner structure of any suitable device embodiment discussed herein may be formed by braiding, weaving, or other filament interlacing techniques described herein similar to that used for formation of the shell or those techniques known in the art of medical textiles and intravascular implants. Alternatively, it may be merely twisted or allowed to form a random mesh of filaments. It may be heat set as described herein and similar to that used to form the shell or it may not be heat treated beyond any heat setting done when the filaments are formed. The inner structure filaments may be metals, polymers or composites thereof. In some embodiments, the filaments are formed of materials that can withstand heat treatment of at least about 450° C. In some embodiments, some of the filaments may be formed of an aramide fiber such as poly paraphenylene terephthalamide available under the trade name Kevlar. In some embodiments, the inner structure filamentary members may be wires with a diameter between about 10 microns (0.0004 inches) and about 30 microns (0.0012 inches). In some cases, the inner structure may comprise materials, coatings or be impregnated with particles or molecules that release elements or chemicals that promote thrombosis and thrombus formation.

As discussed above with regard to the deployment method embodiment shown in FIGS. 23-26, once a properly sized device for treatment of a patient's vasculature 10 has been selected, the delivery and deployment process may take place. During deployment, the tip of a microcatheter 61 may be advanced into or adjacent the vascular site or defect 160. The device for treatment of a patient's vasculature 10 may be inserted through the microcatheter 61 such that the catheter lumen restrains radial expansion of the device during delivery. Once the distal tip or deployment port of the delivery system is positioned in a desirable location adjacent or within a vascular defect 160, the device 10 may be deployed out the distal end of the catheter thus allowing the device to begin to radially expand as shown in FIG. 25. As the device emerges from the distal end of the delivery system, the device 10 expands radially outward to an expanded state within an interior volume the vascular defect. Upon deployment, the device 10 may also be at least partially constrained by an interior surface of the vascular defect 160 depending on the sizing of the device relative to the size of the interior surface of the vascular defect 160. Upon full deployment, radial expansion of the device 10 may serve to exert an outward radial force of the outside surface of the device against the inside surface of the vascular defect to mechanically secure the device within the vascular defect. Deployment of the device 10 may serve to partially isolate the vascular defect from flow, pressure or both coming from the patient's vasculature adjacent the vascular defect.

For some deployment method embodiments, a catheter deflecting device may be placed in the parent artery distal to the vascular site (e.g. aneurysm) 160 to be occluded prior to delivery of the occlusive implant or device for treatment of a patient's vasculature. Such method embodiments may be used for deployment of any of the suitable device embodiments for treatment of a patient's vasculature discussed above. The deflecting device may include an inflatable or expandable element. In some cases, the expandable element may include an inflatable balloon such as the type of inflatable balloon often used for percutaneous angioplasty procedures, but smaller in dimension for use in the cerebral vasculature. As shown in FIG. 60, the deflecting device 410 (e.g. balloon) may include a proximal end 420 and a distal end 422. In use, the balloon 410 may be positioned such that the proximal end 420 of the balloon 410 is disposed distal to an aneurysm neck 412 in the parent artery 414. In addition, the proximal end 416 of the deflecting device 410 is adjacent to the neck 412. The deflecting device 410 may be inserted prior to or after an implant delivery microcatheter 61 is advanced into the aneurysm 160. If placed prior to advancement of the microcatheter 61, the deflecting device 410 may serve as a deflecting member to redirect the microcatheter 61 from the trajectory of the parent artery 414 into the aneurysm 160. The deflecting member 410 may thus be used to facilitate access of the microcatheter 61 into an aneurysm 160.

Figure 62:
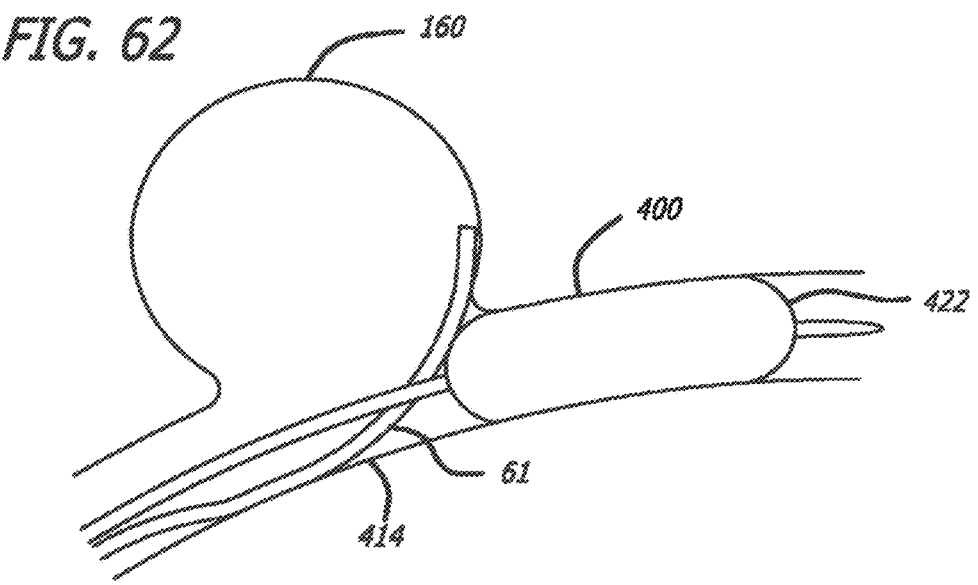
FIG. 62 shows the aneurysm of FIG. 60 with a distal tip of a microcatheter disposed in the aneurysm and a distal portion of the microcatheter disposed against an inflated deflection device.

After insertion of the microcatheter 61 into the target site or aneurysm 160, the deflecting device 410 may facilitate keeping the distal tip 418 of the microcatheter 61 in the desired vascular site location within the aneurysm 160. When any implant or device for treatment of a patient's vasculature is advanced through the microcatheter 61, it is not uncommon for the tip 418 of the microcatheter 61 to "kick back" as the implant enters the aneurysm 160. The kick back force is due to the generally equal and opposite reaction force that is translated into the system as an implant or device for treatment of a patient's vasculature as discussed herein encounters axial resistance due to contact with the vessel wall, clot 191 or previously implanted or deployed device. Such kick back is indicated by arrow 424 in FIG. 61. This response to implant insertion into a vascular site may also result in the catheter straightening out into the parent vessel as indicated by arrow 426 shown in FIG. 61 particularly when the catheter is bent to gain access into a vascular site such as a side-wall aneurysm. As a result of the kick back and catheter straightening, the operator may lose tip position of the microcatheter 61 or access to the aneurysm 160. When deploying a permeable shell implant, which may be stiffer in its collapsed state than other implants such as coils, the risk of kick back and/or microcatheter straightening may be higher. A deflecting device 410 may buttress the lateral deflection of the implant delivery microcatheter 61, as shown in FIG. 62, thus substantially preventing kick back and loss of access to the aneurysm interior volume.

Figure 63:
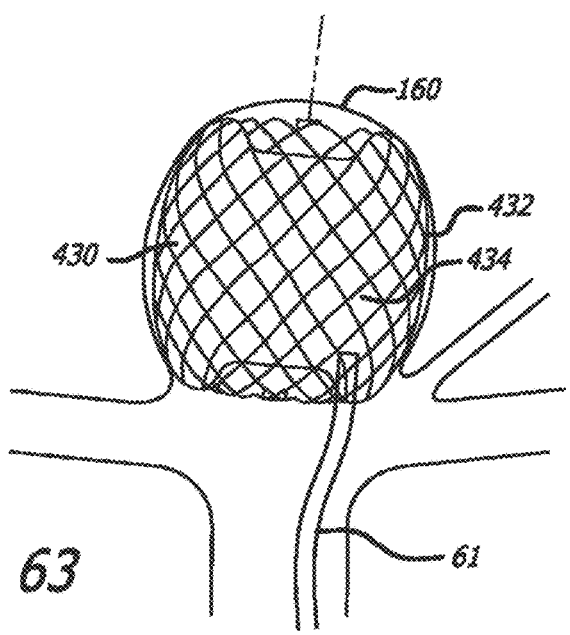
FIG. 63 illustrates an embodiment of a large pore device for treatment of a patient's vasculature disposed within an aneurysm shown in section and a distal end of a microcatheter disposed within an interior volume of the device.
Figure 64:
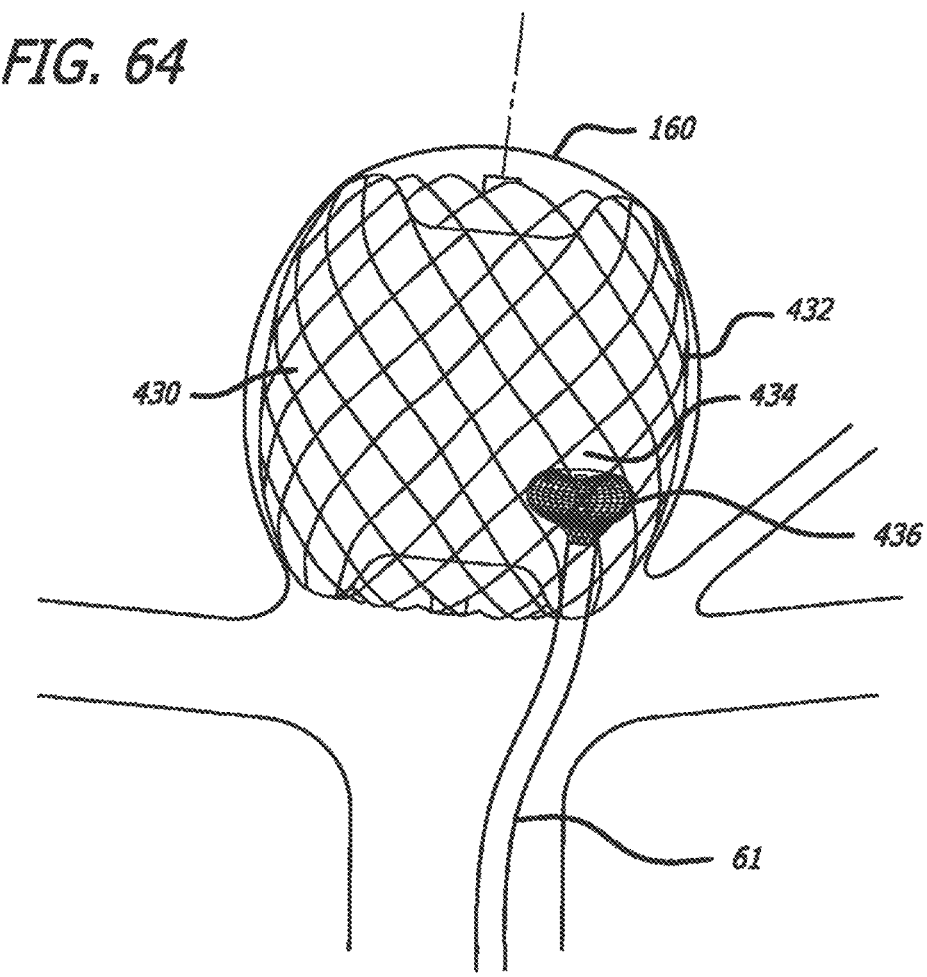
FIG. 64 illustrates a device for treatment of a patient's vasculature being deployed from the distal end of the microcatheter of FIG. 63.

In some embodiments, a permeable shell 430 of a device embodiment for treatment of a patient's vasculature 432 may be constructed with one or more large pores to accommodate insertion of a microcatheter 61 through the one or more large pores. Such a large pore permeable shell 430 may receive a microcatheter 61 for deployment of one or more devices including expandable permeable shells into an interior volume 434 of the large pore device 432. Accordingly, a method for utilizing such a large pore shell 430 may include inserting a microcatheter 61 through a pore of the permeable shell 430 of the device for treatment of a patient's vasculature as shown in FIG. 63. Once the microcatheter 61 is inserted into the interior volume 434 of the deployed device 432 within the aneurysm 160 being treated, a second permeable shell implant device 436 may be delivered through an interior lumen of the microcatheter 61 into the interior space 434 within the large pore shell 430 as shown in FIG. 64.

The large pore shell 430 may have between about 36 and 100 wires that have a diameter between about 0.0015 and 0.004 inches. By filling a vascular site 160 (e.g. aneurysm) sequentially with a plurality of secondary permeable shells 436 with at least one be substantially within an interior volume 434 of the outer large pore shell 430, larger aneurysms 160 may be treatable. Such large aneurysms may thus be treatable with any single woven wire device by deploying multiple units of the device 432 concentrically in series. A single woven wire device 432 may also inherently get larger in collapsed profile if the porosity and radial compliance are kept constant. Thus, to treat larger aneurysms 160 or other vascular sites with a single woven wire permeable shell 430, a large delivery catheter may be required. This may be a disadvantage in many cases as larger catheters are more difficult to navigate and can block too much flow in small blood vessels. Sequential treatment with a large pore shell 430 and then subsequent filling of a portion of the inner volume 434 of the large pore shell 430 with one or more permeable shells 436 may allow large aneurysms greater than about 15 mm in diameter to be treated with a microcatheter 61 that has a lumen that is less than about 0.040 inches in diameter. Coils or other embolic materials may optionally be used to replace or augment the filling of the large pore permeable shell 430.

Figure 65:
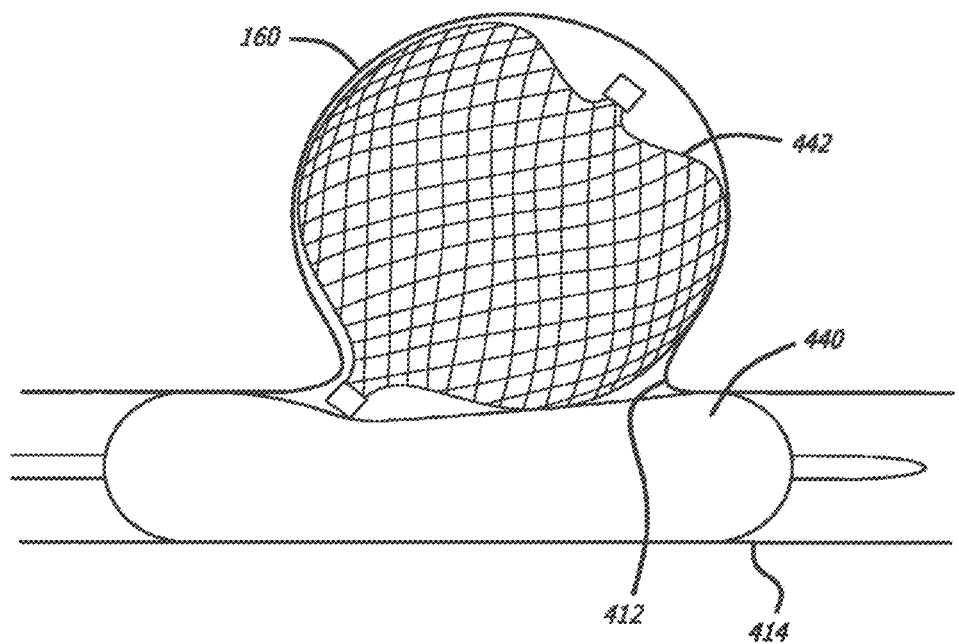
FIG. 65 illustrates an aneurysm in section with a device for treatment of a patient's vasculature deployed within an interior volume of the aneurysm and a flow blockage device disposed in the parent artery adjacent the aneurysm sealing the neck of the aneurysm.

In some method embodiments, a temporary flow blockage device 440 such as an inflatable balloon or other radially expandable intravascular device may be inserted after implantation of a permeable shell 442 to facilitate the occlusion of the vascular site 160 in which the shell 442 has been placed. For example, if a permeable shell 442 has been implanted into a vascular aneurysm 160, by placing a flow blockage device 440 over the aneurysm ostium 412 (i.e. neck) flow into the aneurysm 160 is substantially stopped temporarily. This process may allow the progression of thrombosis within an interior volume of the aneurysm 160 to a point where it continues even after removal of the flow blockage device 440. That is, the flow blockage device 440 may slow the flow within the vascular site 160 and permeable shell 442 to below the thrombotic threshold velocity. As shown in FIG. 65, a balloon 440 may be used to block flow into an aneurysm 160 where a permeable shell 442 has been placed. Balloons are routinely used in the vascular system to temporarily block blood flow. This may be advantageous in particularly high flow situations such as terminal bifurcation aneurysms 160 and in large aneurysms where only a lower density device can be placed due to limitations of the device that can be delivered through suitable microcatheters 61. The flow blockage device 440 may block substantially all or only a portion of blood flow into the vascular site 160 for a period between about 1 and 10 minutes. In some method embodiments, the flow blockage device 440 may be used for less than about 5 minutes. In an alternative embodiment, the flow blockage device 440 is a radially expandable device that temporarily blocks at least a portion of the flow into the aneurysm 160. An exemplary flow blockage device 440 is described by Guterman et al. in U.S. Patent Publication No. 2005/0119684, filed Jul. 14, 2003, titled "Aneurysm Buttress Arrangement", which is herein incorporated in its entirety by reference. With this method embodiment, the flow blockage device 440 may be positioned in the parent artery 414 prior to delivery of a permeable shell device 440.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments. Accordingly, it is not intended that the invention be limited by the forgoing detailed description.

What is claimed is:

1. A device for implantation within a vascular defect or aneurysm, comprising:
    a self-expanding resilient first layer including:
    a proximal end,
    a distal end,
    a longitudinal axis,
    a plurality of elongate filaments disposed in a woven structure between the proximal end and distal end,
    the first layer being movable to a collapsed state configured for delivery within a microcatheter with the elongate filaments extending longitudinally from the proximal end to the distal end, the first layer being movable to an expanded state with a longitudinally shortened configuration relative to the collapsed state, first layer being formed as a continuous closed volume in the expanded state, the continuous closed volume formed by the elongate filaments defining a surface having a number of undulations, wherein in the expanded state the first layer has a three-dimensional shape, an internal gap being established between a distal-most surface of the first layer and a distal-most surface of an inner layer in the expanded state, the internal gap being between 5% and 40% of a total longitudinal height of the device measured along a longitudinal axis of the device.

2. The device of claim 1, wherein the undulations of the elongate filaments form at least a first radial groove or depression adjacent a circumference of the first layer.

3. The device of claim 1, wherein the undulations provide multiple porous layers through which blood must pass.

4. The device of claim 1, wherein the undulations establish baffling in a region of an aneurysm when the device is disposed in the aneurysm to promote embolization.

5. The device of claim 1, wherein the first layer forms an undulating shape that alternates between surfaces defining the continuous closed volume in the expanded state.

6. An assembly comprising:
    a porous body including:

a proximal end,
a distal end,
a plurality of elongate filaments disposed between the proximal end and distal end,
the body being movable to a collapsed state configured for delivery within a microcatheter with the elongate filaments extending longitudinally from the proximal end to the distal end, the body being movable to an expanded state with a longitudinally shortened configuration relative to the collapsed state, the body being formed as a closed volume in the expanded state, wherein in the expanded state the body has a three-dimensional shape with a continuous outer surface defining at least first and second layers, the first portion being defined by plural filament segments and the second portion being defined by plural filament segments, an internal gap being established between a distal-most surface of the first layer and a distal-most surface of an inner layer in the expanded state, the internal gap being between 5% and 40% of a total longitudinal height of the body measured along a longitudinal axis of the body.

7. The assembly of claim 6, wherein the continuous outer surface is formed with undulations.

8. The assembly of claim 7, wherein the undulations form at least a first radial groove or depression adjacent a circumference of the body.

9. The assembly of claim 6, wherein the undulations provide multiple porous layers through which blood must pass.

10. The assembly of claim 6, wherein the undulations establish baffling in a region of an aneurysm when the body is disposed in the aneurysm to promote embolization.

11. The assembly of claim 6, wherein the body forms an undulating shape that alternates between surfaces defining the closed volume in the expanded state.

12. An apparatus comprising:
a body including:
a proximal end,
a distal end,
a plurality of elongate filaments disposed between the proximal end and distal end,
the body being movable to a collapsed state configured for delivery within a delivery device with the elongate filaments extending from the proximal end to the distal end, the body being movable to an expanded state with a longitudinally shortened configuration relative to the collapsed state, the body being formed as a closed volume in the expanded state, wherein in the expanded state the body has a three-dimensional shape with an outer surface, the outer surface having plural undulations in the expanded state, a gap being established between a distal-most surface of a first layer of the body and a distal-most surface of an inner layer of the body in the expanded state, the internal gap being between 5% and 40% of a total longitudinal height of the apparatus measured along a longitudinal axis of the apparatus.

13. The apparatus of claim 12, wherein the undulations form at least a first radial groove or depression adjacent a circumference of the body.

14. The apparatus of claim 12, wherein the undulations provide multiple porous layers through which blood must pass.

15. The apparatus of claim 12, wherein the undulations establish baffling in a region of an aneurysm when the body is disposed in the aneurysm to promote embolization.

16. The apparatus of claim 12, wherein the body forms an undulating shape that alternates between surfaces defining the continuous closed volume in the expanded state.

* * * * *